United States Patent
Fujisawa et al.

(10) Patent No.: US 9,500,790 B2
(45) Date of Patent: Nov. 22, 2016

(54) OPTICAL FILM, CIRCULARLY POLARIZING PLATE, AND IMAGE DISPLAY DEVICE

(71) Applicant: KONICA MINOLTA, INC., Chiyoda-ku, Tokyo (JP)

(72) Inventors: Rie Fujisawa, Kanagawa (JP); Midori Kogure, Hyogo (JP); Takatugu Suzuki, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 86 days.

(21) Appl. No.: 14/379,994

(22) PCT Filed: Feb. 19, 2013

(86) PCT No.: PCT/JP2013/000915
§ 371 (c)(1),
(2) Date: Aug. 20, 2014

(87) PCT Pub. No.: WO2013/125211
PCT Pub. Date: Aug. 29, 2013

(65) Prior Publication Data
US 2015/0247963 A1    Sep. 3, 2015

(30) Foreign Application Priority Data
Feb. 22, 2012  (JP) ................. 2012-036837

(51) Int. Cl.
*G02B 5/30* (2006.01)
*G02B 27/28* (2006.01)
(Continued)

(52) U.S. Cl.
CPC ......... *G02B 5/3083* (2013.01); *C07D 207/452* (2013.01); *C07D 209/86* (2013.01);
(Continued)

(58) Field of Classification Search
CPC ...... G02B 5/208; G02B 5/22; G02B 5/3083; G02B 5/3091; G02B 5/32; G02B 27/286

USPC .......... 359/352, 361, 489.07, 489.12, 489.13
See application file for complete search history.

(56) References Cited

U.S. PATENT DOCUMENTS

| 6,519,016 B1 | 2/2003 | Ichihashi et al. |
| 7,166,339 B1 | 1/2007 | Mori et al. |

(Continued)

FOREIGN PATENT DOCUMENTS

| JP | 10068816 A | 3/1998 |
| JP | 2001091741 A | 4/2001 |

(Continued)

OTHER PUBLICATIONS

Korean Office Action (and English translation thereof) dated Nov. 6, 2015, issued in counterpart Korean Application No. 10-2014-7022953.

(Continued)

*Primary Examiner* — Ricky D Shafer
(74) *Attorney, Agent, or Firm* — Holtz, Holtz & Volek PC

(57) ABSTRACT

A optical film includes a thermoplastic resin and a compound wherein: (1) the absorption spectrum of said compound in solution has at least two absorption maxima in the 200-350 nm wavelength range; (2) letting $\lambda max1$ represent the wavelength of a first absorption maximum (one of the aforementioned absorption maxima) and letting $\lambda max2$ represent the wavelength of a second absorption maximum (another of the aforementioned absorption maxima) at a shorter wavelength than the first absorption maximum, $(\lambda max1 - \lambda max2)$ is at least 20 nm; (3) the aspect ratio of the molecules of the compound is at least 1.70; (4) each molecule of the compound has a non-aromatic hydrocarbon ring, a non-aromatic heterocycle, or an aromatic heterocycle; (5) the in-plane-retardation increase sensitivity of the compound is at least 0.1; 110 $nm \leq R_0(550) \leq 170$ nm; $0.72 \leq R_0(450)/R_0(550) \leq 0.96$; and $0.83 \leq R_0(550)/R_0(650) \leq 0.97$.

14 Claims, 5 Drawing Sheets

(51) Int. Cl.
*G02B 5/22* (2006.01)
*G02B 5/20* (2006.01)
*G02B 5/32* (2006.01)
*C07D 265/22* (2006.01)
*C07D 207/452* (2006.01)
*C07D 277/66* (2006.01)
*C07D 209/86* (2006.01)
*C07D 295/18* (2006.01)
*C07D 213/64* (2006.01)
*C07D 307/60* (2006.01)
*G02F 1/13363* (2006.01)
*G02B 27/26* (2006.01)
*G02B 1/111* (2015.01)
*H01L 51/52* (2006.01)
*G02F 1/1335* (2006.01)

(52) U.S. Cl.
CPC ........... *C07D213/64* (2013.01); *C07D 265/22* (2013.01); *C07D 277/66* (2013.01); *C07D 295/18* (2013.01); *C07D 307/60* (2013.01); *G02B 1/111* (2013.01); *G02B 5/208* (2013.01); *G02B 5/22* (2013.01); *G02B 5/305* (2013.01); *G02B 5/3091* (2013.01); *G02B 5/32* (2013.01); *G02B 27/26* (2013.01); *G02B 27/286* (2013.01); *G02F 1/13363* (2013.01); *H01L 51/5281* (2013.01); *G02F 2001/133541* (2013.01)

(56) References Cited

U.S. PATENT DOCUMENTS

| | | | |
|---|---|---|---|
| 2010/0003426 | A1 | 1/2010 | Suzuki |
| 2014/0319508 | A1* | 10/2014 | Tanihara ............... G02B 5/3025 257/40 |

FOREIGN PATENT DOCUMENTS

| | | |
|---|---|---|
| JP | 3459779 B2 | 10/2003 |
| JP | 2004050516 A | 2/2004 |
| JP | 2007030466 A | 2/2007 |
| JP | 2007249180 A | 9/2007 |
| JP | 2009064007 A | 3/2009 |
| JP | 2010235879 A | 10/2010 |
| JP | 4583648 B2 | 11/2010 |
| JP | 4605908 B2 | 1/2011 |
| WO | 2008015879 A1 | 2/2008 |

OTHER PUBLICATIONS

Chinese Office Action (and English translation thereof) dated Nov. 19, 2015, issued in Chinese Application No. 201380010572.1.
International Search Report (ISR) dated May 28, 2013 issued in International Application No. PCT/JP2013/000915.

* cited by examiner

| | COMPOUND | | SOLUTION ABSORPTION SPECTRUM |
|---|---|---|---|
| COMPOUNDS USED IN PRESENT INVENTION | ① COMPOUND A-41 | | $\lambda\max①\text{-}1 = 301\,nm$ |
| | | | $\lambda\max①\text{-}2 = 230\,nm$ |
| | | | $((\lambda\max①\text{-}1) - (\lambda\max①\text{-}2)) = 71\,nm$ |
| | | | $(Abs①\text{-}1)/(Abs①\text{-}2) = 0.74$ |
| | ② COMPOUND A-62 | | $\lambda\max②\text{-}1 = 270.0\,nm$ |
| | | | $\lambda\max②\text{-}2 = 220.0\,nm$ |
| | | | $(\lambda\max②\text{-}1) - (\lambda\max②\text{-}2) = 50\,nm$ |
| | | | $(Abs②\text{-}1)/(Abs②\text{-}2) = 0.29$ |
| COMPOUNDS CONVENTIONALLY USED | ③ COMPARATIVE COMPOUND b | | $\lambda\max③\text{-}1 = 282.0\,nm$ |
| | | | $\lambda\max③\text{-}2 = 240.0\,nm$ |
| | | | $(\lambda\max③\text{-}1) - (\lambda\max③\text{-}2) = 42\,nm$ |
| | | | $(Abs③\text{-}1)/(Abs③\text{-}2) = 0.06$ |
| | ④ COMPARATIVE COMPOUND a | | $\lambda④\text{-}1 = 240.0\,nm$ |
| | | | $\lambda④\text{-}2 = 233.5\,nm$ |
| | | | $(\lambda④\text{-}1) - (\lambda④\text{-}2) = 6.5\,nm$ |

FIG. 1C

OPTICAL FILM, CIRCULARLY POLARIZING PLATE, AND IMAGE DISPLAY DEVICE

TECHNICAL FIELD

The present invention relates to an optical film, a circularly polarizing plate, and an image display device.

BACKGROUND ART

A λ/4 retardation film enables conversion of linearly polarized light to circularly polarized light or elliptically polarized light, or conversion of circularly polarized light or elliptically polarized light to linearly polarized light. Such a λ/4 retardation film is used in a wide variety of optical applications including image display devices, optical pickup apparatuses and the like.

A λ/4 retardation film used in an optical device which utilizes a laser light source having a particular wavelength, such as an optical pickup apparatus, will be acceptable if the λ/4 retardation film is capable of providing a phase difference (hereinafter, referred to as "retardation") of ¼ wavelength only to light having a particular wavelength. However, a λ/4 retardation film that is used in a color image display device, an antireflective film for visible light and the like is required to be able to provide a retardation of ¼ wavelength to light over the entire visible light region.

Therefore, a λ/4 retardation film used in a color image display device is required to have negative wavelength dispersibility (reverse wavelength dispersibility), in which the retardation given to light having longer wavelengths is larger than the retardation given to light having shorter wavelengths. However, it has been difficult to obtain a film which gives a retardation of ¼ wavelength and exhibits sufficient negative wavelength dispersibility (reverse wavelength dispersibility); and particularly, a film which is single-layered and is capable of providing a retardation of λ/4 to light over a wide wavelength region.

A conventional λ/4 retardation film that exhibits negative wavelength dispersibility (reverse wavelength dispersibility) is obtained by bonding retardation films having different wavelength dispersing characteristics such that the optical axes thereof intersect each other (see, for example, PTL 1).

However, it has been difficult to produce such a film because it is necessary to adjust the retardation of each of the laminated retardation films to ¼ wavelength or ½ wavelength. Furthermore, since the ranges of retardation of the laminated retardation films are limited, the extent to which the wavelength dispersibility can be adjusted is limited, and thus a retardation of ¼ wavelength cannot be provided to light having a sufficiently wide wavelength region. Furthermore, in order to develop a retardation of ¼ wavelength or ½ wavelength in each film, it is necessary to increase the thickness of each film, resulting in the image display device having increased thickness.

As a method of reducing film thickness, a method is available wherein a material having high retardation development properties is added in the film. However, although a film containing a material having high retardation development properties can reduce the film thickness, the retardation in the in-plane direction or retardation in the thickness direction is prone to vary greatly as a result of slight variation in the thickness of the film. Therefore, there has been a problem that not only it is difficult to adjust the retardation, but also color unevenness or a decrease in contrast may occur.

PTL 2 proposes a retardation plate having optically anisotropic layer A having a retardation of λ/2 wavelength and optically anisotropic layer B having a retardation of λ/4 wavelength, wherein any one of the optically anisotropic layers A and B is a layer formed from liquid crystalline molecules. However, even for this retardation plate, since the retardations of the respective optically anisotropic layers are limited to ¼ wavelength or ½ wavelength as described above, it has been difficult to sufficiently control the wavelength dispersibility of the retardation plate.

In this regard, an investigation has been conducted on a retardation film which, even with a single layer, can achieve a good balance between the retardation and the wavelength dispersibility by the selection of a resin or a retardation controlling agent. For example, PTL 3 proposes a stretched film formed of a cellulose acetate having a particular degree of acetylation. PTL 4 proposes an optical film containing a compound having a coordinatability-imparting group and a birefringence-imparting group as a retardation controlling agent; PTL 5 proposes a retardation plate containing a cellulose ester and a retardation enhancer having two or more aromatic rings; and PTL 6 proposes an optical film containing, as a retardation controlling agent, a low molecular weight compound in which the magnitude of the dipole moment in a direction perpendicular to the major axis direction of the molecule is larger than the magnitude of the dipole moment in a direction parallel to the major axis direction of the molecule.

CITATION LIST

Patent Literature

PTL 1
Japanese Patent Application Laid-Open No. 10-68816
PTL 2
Japanese Patent Application Laid-Open No. 2001-91741
PTL 3
Japanese Patent No. 3459779
PTL 4
Japanese Patent No. 4583648
PTL 5
Japanese Patent No. 4605908
PTL 6
Japanese Patent Application Laid-Open No. 2007-249180

SUMMARY OF INVENTION

Technical Problem

However, as for the stretched film of PTL 3, the cellulose ester film alone could not sufficiently control both the retardation and the wavelength dispersibility. The retardation controlling agent described in PTL 4 has low retardation development properties (particularly, the retardation development properties in the in-plane direction), and in order to obtain a desired retardation, it was necessary to increase the film thickness. Furthermore, the retardation controlling agent described in PTL 6 has noticeably poor light resistance. The retardation increasing agent described in PTL 5 has inferior reverse wavelength dispersibility, and has problems such as film coloration and light resistance.

As such, the retardation development properties and the reverse wavelength dispersibility are in a trade-off relationship, and thus, there is a demand for an optical film which has high retardation development properties over a wide wavelength region while exhibiting sufficient reverse wavelength dispersibility.

The present invention was achieved under such circumstances, and it is an object of the invention to provide an optical film which exhibits, even if the film thickness is small, high development properties for the retardation in the in-plane direction and sufficient reverse wavelength dispersibility.

Solution to Problem

In order to solve the problems described above, the inventors of the present invention employed a cyclic group-based mother nucleus wherein the positions of substituents could be relatively freely disposed, for the purpose of having a retardation increasing function; however, although the retardation increasing effect was excellent in a particular range of the aspect ratio, the wavelength dispersibility was still insufficient. Therefore, the inventors conducted various investigations by varying the kind and combination of the substituents, and as a result, the inventors found that the wavelength dispersibility is excellent when adjacent atoms to which the substituents are attached are different from each other, and that such a compound has unique absorption peaks. Furthermore, it was made clear that although not necessarily included in the scope of the structure of compound initially investigated, a compound having such absorption peaks provides the effects of the present invention. The inventors also found that when the relevant optical film is used, an image display device having excellent light resistance with less color change is obtained, and thus the inventors completed the present invention. That is, the problems to be solved in relation to the present invention are solved by the following means.

[1] An optical film including a thermoplastic resin and at least one kind of compound that satisfies all of the following conditions (1) to (5):

(1) the compound has at least two absorption maxima in a wavelength region of from 200 nm to 350 nm in a solution absorption spectrum;

(2) when a wavelength of a first absorption maximum of the two absorption maxima in the wavelength region of from 200 nm to 350 nm is designated as λmax1, and a wavelength of a second absorption maximum of the two absorption maxima at shorter wavelengths than the first absorption maximum is designated as λmax2, (λmax1−λmax2) is 20 nm or more;

(3) an aspect ratio of a molecule of the compound is 1.70 or more;

(4) the compound has a non-aromatic hydrocarbon ring, an aromatic heterocyclic ring, or a non-aromatic heterocyclic ring in the molecule; and (5) for a sample film having a thickness of 60 μm and containing the thermoplastic resin and the compound at a proportion of 1% by mass with respect to the thermoplastic resin, when a retardation in an in-plane direction at a wavelength of 550 nm before stretching of the sample film is designated as $R_0A0(550)$, and a retardation in the in-plane direction at a wavelength of 550 nm after stretching at a temperature higher by 25° C. than a glass transition temperature of the sample film is designated as $R_0A1(550)$, so that a in-plane retardation sensitivity obtained by dividing $(R_0A1(550)-R_0A0(550))$ by the stretch ratio is designated as A; and for a blank film having a thickness of 60 μm and formed from the thermoplastic resin, when the retardation in the in-plane direction at a wavelength of 550 nm before stretching of the blank film is designated as $R_0B0(550)$, and the retardation in the in-plane direction at a wavelength of 550 nm after stretching at a temperature higher by 25° C. than the glass transition temperature of the blank film is designated as $R_0B1(550)$, so that an in-plane retardation sensitivity obtained by dividing $(R_0B1(550)-R_0B0(550))$ by the stretch ratio is designated as B, an in-plane retardation increase sensitivity defined by (A−B) is 0.1 or more, wherein when the retardations in the in-plane direction measured at the wavelengths of 450 nm, 550 nm and 650 nm are designated as $R_0(450)$, $R_0(550)$ and $R_0(650)$, respectively, Formulas (a) to (c) are all satisfied:

$$110 \text{ nm} \leq R_0(550) \leq 170 \text{ nm}; \tag{a}$$

$$0.72 \leq R_0(450)/R_0(550) \leq 0.96; \text{ and} \tag{b}$$

$$0.83 \leq R_0(550)/R_0(650) \leq 0.97. \tag{c}$$

[2] The optical film according to [1], wherein the thermoplastic resin includes a cellulose derivative.

[3] The optical film according to [1] or [2], wherein the compound has at least one non-aromatic ring in the molecule.

[4] The optical film according to any one of [1] to [3], wherein a value of (λmax1−λmax2) of the compound is 50 nm or more.

[5] The optical film according to any one of [1] to [4], wherein when a refractive index in the in-plane slow axis direction of the optical film is designated as nx, a refractive index in a direction perpendicular to the slow axis within the plane of the optical film is designated as ny, and a refractive index in the thickness direction of the optical film is designated as nz, the relationship of Formula (d) is further satisfied:

$$0 \leq Nz = Rth(550)/R_0(550) + 0.5 \leq 1 \tag{d}$$

[6] The optical film according to any one of [1] to [5], wherein the compound is represented by the following General Formula (A):

[Chemical Formula 1]

General Formula (A)

$$R_1-L_1-\underset{(R_3)_m}{\underset{|}{(Q}}\overset{W_a\ W_b}{\overset{\diagdown\ \diagup}{)}}-L_2)_n-R_2$$

wherein in General Formula (A),

Q represents an aromatic hydrocarbon ring, a non-aromatic hydrocarbon ring, an aromatic heterocyclic ring, or a non-aromatic heterocyclic ring;

$W_a$ and $W_b$ each represent a hydrogen atom or a substituent, each being bonded to an atom that constitutes the ring of Q, the atom to which $W_a$ is bonded being adjacent to the atom to which $W_b$ is bonded, $W_a$ and $W_b$ being different from each other, and $W_a$ and $W_b$ may be bonded to each other to form a ring;

$R_3$ represents a substituent;

m is an integer from 0 to 2;

when m is 2, $R_3$'s may be identical or different;

$L_1$ and $L_2$ each independently represent a single bond, or a divalent linking group selected from the group consisting of an alkylene group, an alkenylene group, an alkynylene group, —O—, —(C=O)—, —(C=O)—O—, —NR$_L$—, —S—, —(O=S=O)—, and —(C=O)—NR$_L$—, or a combination thereof;

R$_L$ represents a hydrogen atom or a substituent; and

R$_1$ and R$_2$ each independently represent a substituent.

[7] The optical film according to any one of [1] to [6], wherein the compound represented by General Formula (A) is a compound represented by the following General Formula (B):

[Chemical Formula 2]

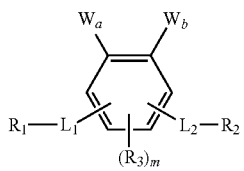

General Formula (B)

wherein in General Formula (B),

W$_a$ and W$_b$ each represent a hydrogen atom or a substituent, each being bonded to an atom that constitutes the ring of Q, while the atom to which W$_a$ is bonded is adjacent to the atom to which W$_b$ is bonded, with W$_a$ and W$_b$ being different from each other, and W$_a$ and W$_b$ may be bonded to each other and form a ring;

R$_3$ represents a substituent;

m represents from 0 to 2;

when m is 2, R$_3$'s may be identical or different;

L$_1$ and L$_2$ each independently represent a single bond, or a divalent linking group selected from the group consisting of an alkylene group, an alkenylene group, an alkynylene group, —O—, —(C=O)—, —(C=O)—O—, —NR$_L$—, —S—, —(O=S=O)—, and —(C=O)—NR$_L$—, or a combination thereof;

R$_L$ represents a hydrogen atom or a substituent; and

R$_1$ and R$_2$ each independently represent a substituent.

[8] The optical film according to any one of [1] to [7], wherein the compound represented by General Formula (B) is a compound represented by the following General Formula (1B):

[Chemical Formula 3]

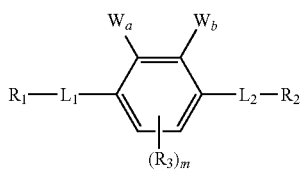

General Formula (1B)

wherein in General Formula (1B),

W$_1$ represents a cyclic group, and among the ring-constituting atoms of W$_1$, the atom that is bonded to the benzene ring is a carbon atom or a nitrogen atom;

R$_3$ represents a substituent;

m is an integer from 0 to 2;

when m is 2, R$_3$'s may be identical or different;

L$_1$ and L$_2$ each independently represent a single bond, or a divalent linking group selected from the group consisting of an alkylene group, an alkenylene group, an alkynylene group, —O—, —(C=O)—, —(C=O)—O—, —NR$_L$—, —S—, —(O=S=O)—, and —(C=O)—NR$_L$—, or a combination thereof;

R$_L$ represents a hydrogen atom or a substituent; and

R$_1$ and R$_2$ each independently represent a substituent.

[9] The optical film according to any one of [1] to [7], wherein the compound represented by General Formula (B) is represented by the following General Formula (2B):

[Chemical Formula 4]

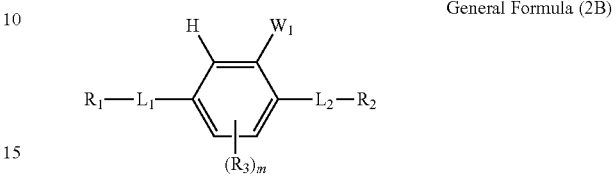

General Formula (2B)

wherein in General Formula (2B),

W$_1$ represents a cyclic group, and among the ring-constituting atoms of W$_1$, the atom that is bonded to the benzene ring is a carbon atom or a nitrogen atom;

R$_3$ represents a substituent;

m represents from 0 to 2;

when m is 2, R$_3$'s may be identical or different;

L$_1$ and L$_2$ each independently represent a single bond, or a divalent linking group selected from the group consisting of an alkylene group, an alkenylene group, an alkynylene group, —O—, —(C=O)—, —(C=O)—O—, —NR$_L$—, —S—, —(O=S=O)—, and —(C=O)—NR$_L$—, or a combination thereof;

R$_L$ represents a hydrogen atom or a substituent; and

R$_1$ and R$_2$ each independently represent a substituent.

[10] The optical film according to any one of [1] to [9], wherein a thickness of the optical film is 10 μm to 100 μm.

[11] The optical film according to any one of [1] to [10], wherein a content of the compound is 1% to 15% by mass with respect to the thermoplastic resin.

[12] The optical film according to any one of [1] to [11], wherein an angle formed by the in-plane slow axis of the optical film and a width direction of the optical film is from 40° to 50°.

[13] A circularly polarizing plate including the optical film according to any one of [1] to [12].

[14] An image display device including the optical film according to any one of [1] to [12].

Advantageous Effects of Invention

According to the present invention, there can be provided an optical film which exhibits, even though the film thickness is small, high retardation development properties in the in-plane direction and sufficient reverse wavelength dispersibility. Furthermore, an image display device including the optical film has excellent black color reproducibility under natural light and excellent visibility from an oblique direction.

BRIEF DESCRIPTION OF DRAWINGS

FIGS. 1A to 1C show graphs illustrating exemplary solution absorption spectra of compounds;

DESCRIPTION OF EMBODIMENTS

1. Optical Film

Figure 1A:
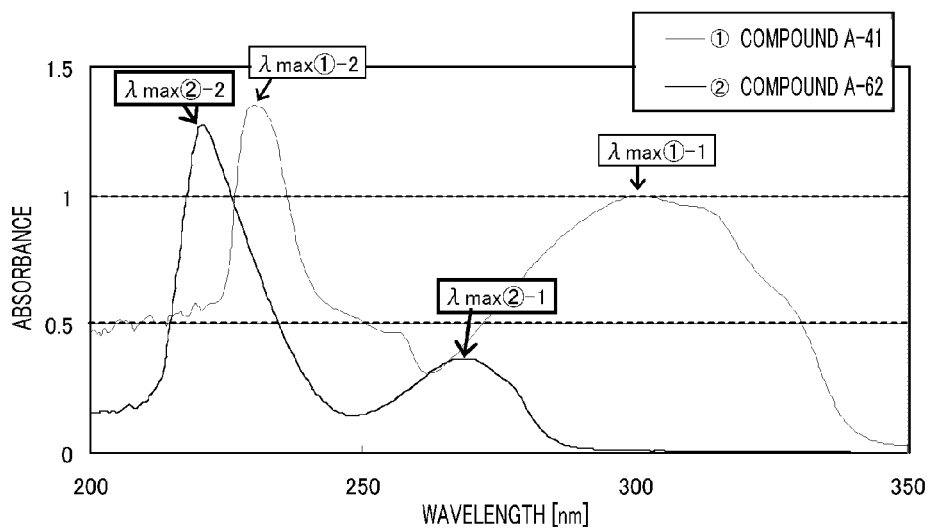

The optical film of the present invention contains a thermoplastic resin and a compound used in the present invention.

Thermoplastic Resin

Examples of the thermoplastic resin include a cellulose derivative (for example, a cellulose ester-based resin or a cellulose ether-based resin), a polycarbonate-based resin, a polystyrene-based resin, a polysulfone-based resin, a polyester-based resin, a polyallylate-based resin, a (meth)acrylic resin, and an olefin-based resin (for example, a norbornene-based resin, a cyclic olefin-based resin, a cyclic conjugated diene-based resin, or a vinyl alicyclic hydrocarbon-based resin). Among them, a cellulose derivative, a (meth)acrylic resin, a polycarbonate-based resin, or a cyclic olefin-based resin is preferred; a cellulose derivative is more preferred; and a cellulose ester-based resin is most preferred.

Cellulose Derivative

A cellulose derivative is a compound based on cellulose as a raw material (a compound having a cellulose skeleton). Examples of the cellulose derivative include a cellulose ether (for example, methyl cellulose, ethyl cellulose, hydroxyethyl cellulose, hydroxypropyl cellulose, or cyanoethyl cellulose), a cellulose ester (the details will be described below), a cellulose ether ester (for example, acetylmethyl cellulose, acetylethyl cellulose, acetylhydroxyethyl cellulose, or benzoylhydroxypropyl cellulose), a cellulose carbonate (for example, cellulose ethyl carbonate), and a cellulose carbamate (for example, may be cellulose phenyl carbamate), and a preferred cellulose derivative is a cellulose ester. The cellulose derivatives may be used singly or as a mixture thereof.

The cellulose ester is a compound obtained by subjecting cellulose and at least one of an aliphatic carboxylic acid and an aromatic carboxylic acid, both having about 2 to 22 carbon atoms, to an esterification reaction. Preferably, the cellulose ester is a compound obtained by subjecting cellulose and a lower fatty acid having 6 or fewer carbon atoms to an esterification reaction.

The acyl group contained in a cellulose ester may be linear or branched, or may form a ring, and may have another substituent. When the total degree of substitution of the acyl group is constant, an acyl group having a larger number of carbon atoms is likely to cause a decrease in birefringence. Therefore, the number of carbon atoms of the acyl group is preferably 2 to 6, more preferably 2 to 4, and even more preferably 2 to 3.

Specific examples of the cellulose ester that can be used include cellulose acetate, as well as mixed fatty acid esters such as cellulose acetate propionate, cellulose acetate butyrate, cellulose acetate propionate butyrate, and cellulose acetate phthalate. Preferred examples include cellulose acetate, cellulose acetate butyrate, and cellulose acetate propionate. The butyryl group that can be contained in the cellulose ester may be linear or may be branched.

The total degree of substitution of acyl groups of the cellulose ester can be adjusted to about 2.0 to 3.0. The total degree of substitution of acyl groups is preferably 2.0 to 2.5 from the viewpoint of increasing the retardation development properties, and the total degree of substitution is preferably 2.5 to 3.0 from the viewpoint of increasing moisture resistance or the like.

In particular, the degree of substitution of an acyl group having 3 or more carbon atoms is preferably 2.0 or less. If the degree of substitution of an acyl group having 3 or more carbon atoms is more than 2.0, the retardation development properties are prone to decrease.

The degree of substitution of acyl groups of the cellulose ester can be measured by the method stipulated in ASTM-D817-96.

In order to increase the mechanical strength of the resultant film, the number average molecular weight of the cellulose derivative is preferably in the range of $6 \times 10^4$ to $3 \times 10^5$, and more preferably in the range of $7 \times 10^4$ to $2 \times 10^5$.

The weight average molecular weight (Mw) and the number average molecular weight (Mn) of the cellulose derivative are measured using gel permeation chromatography (GPC). The measurement conditions are as follows.

Solvent: methylene chloride;
Column: Three columns of SHODEX K806, K805, K803G (manufactured by Showa Denko K.K.) are connected and used;
Column temperature: 25° C.;
Sample concentration: 0.1% by mass
Detector: RI Model 504 (manufactured by GL Sciences, Inc.);
Pump: L6000 (manufactured by Hitachi, Ltd.);
Flow rate: 1.0 ml/min
Calibration curve: A calibration curve based on 13 samples of Mw=1,000,000 to 500 STK standard polystyrene (manufactured by Tosoh Corporation). It is preferred that the molecular weights of the 13 samples are approximately equally spaced.

The content of residual sulfuric acid in the cellulose derivative is preferably in the range of 0.1 ppm to 45 ppm by mass, and more preferably in the range of 1 ppm to 30 ppm by mass, in terms of elemental sulfur. Sulfuric acid may be considered to be remaining in the film in form of salt. If the content of residual sulfuric acid is more than 45 ppm by mass, fracture is prone to occur when the film is subjected to hot drawing, or to slitting after hot drawing. The content of the residual sulfuric acid can be measured by the method stipulated in ASTM D817-96.

The content of a free acid in the cellulose derivative is preferably 1 ppm to 500 ppm by mass, more preferably 1 ppm to 100 ppm by mass, and even more preferably 1 ppm to 70 ppm by mass. When the content of the free acid is in the range described above, fracture does not easily occur when the film is subjected to hot drawing, or to slitting after hot drawing, as described previously. The content of the free acid can be measured by the method stipulated in ASTM D817-96.

Cellulose derivatives occasionally contain trace amounts of metal components. It is contemplated that the trace amounts of metal components originate from the water used in the synthesis processes for the cellulose derivatives. It is preferable that the content of components that may become insoluble cores, such as these metal components, be smaller. Particularly, there are occasions in which metal ions such as iron, calcium and magnesium ions form salts with resin decomposition products or the like that may possibly contain organic acidic groups, and form insolubles. Furthermore, there is a risk that calcium (Ca) components are likely to form coordinate compounds (that is, complexes) with acidic components such as carboxylic acids and sulfonic acids and with many ligands, and may form many insoluble residues (insoluble precipitates and turbidity) originating from calcium.

Specifically, the content of iron (Fe) components in the cellulose derivative is preferably 1 ppm by mass or less. Furthermore, the content of calcium (Ca) components in the cellulose derivative is preferably 60 ppm by mass or less, and more preferably 0 ppm to 30 ppm by mass. The content of magnesium (Mg) components in the cellulose derivative is preferably 0 ppm to 70 ppm by mass, and particularly preferably 0 ppm to 20 ppm by mass.

The contents of metal components such as iron (Fe) components, calcium (Ca) components and magnesium (Mg) components can be determined by subjecting a bone-dried cellulose derivative to pretreatments using a microdigest wet decomposition apparatus (sulfuric acid and nitric acid decomposition) and alkali dissolution, and then measuring the content using an ICP-AES (inductively coupled plasma emission spectroscopic analyzer).

The contents of residual alkaline earth metals, residual sulfuric acid and residual acids can be adjusted by sufficiently washing the cellulose derivative obtained by synthesis.

The cellulose derivative can be produced by a known method. Specifically, for example, the cellulose derivative can be synthesized by referring to the method described in Japanese Patent Application Laid-Open No. HEI10-45804A. There are no particular limitations on the cellulose as a raw material of the cellulose derivative, and examples include cotton linter, wood pulp, and kenaf. Cellulose derivatives produced from different raw materials may also be used in mixture.

(Meth)Acrylic Resin

A (meth)acrylic resin may be a homopolymer of a (meth) acrylic acid ester, or a copolymer of a (meth)acrylic acid ester and another copolymerizable monomer. The (meth) acrylic acid ester is preferably methyl methacrylate. The proportion of a constituent unit derived from methyl methacrylate in the copolymer is preferably 50% by mass or more, and more preferably 70% by mass or more.

Examples of the copolymerizable monomer in a copolymer of methyl methacrylate and another copolymerizable monomer include an alkyl methacrylate having an alkyl moiety with 2 to 18 carbon atoms; an alkyl acrylate having an alkyl moiety with 1 to 18 carbon atoms; an alkyl(meth) acrylate having an alkyl moiety having a hydroxyl group and 1 to 18 carbon atoms, which can form a lactone ring structure that will be described below; an α,β-unsaturated acid such as acrylic acid or methacrylic acid; an unsaturated group-containing divalent carboxylic acid such as maleic acid, fumaric acid or itaconic acid; an aromatic vinyl compound such as styrene or α-methylstyrene; an α,β-unsaturated nitrile such as acrylonitrile or methacrylonitrile; an acrylamide derivative such as maleic anhydride, maleimide, N-substituted maleimide, glutaric anhydride, or acryloylmorpholine (ACMO); and N-vinylpyrrolidone (VP). These monomers may be used singly or in combination.

Among them, in order to increase the heat-resistant decomposability or fluidity of the copolymer, an alkyl acrylate such as methyl acrylate, ethyl acrylate, n-propyl acrylate, n-butyl acrylate, s-butyl acrylate, or 2-ethylhexyl acrylate; or an alkyl(meth)acrylate having a hydroxyl group, such as methyl 2-(hydroxymethyl)acrylate or ethyl 2-(hydroxymethyl)acrylate is preferred. In order to increase compatibility with cellulose esters, acryloylmorpholine and the like are preferred.

From the viewpoint of increasing heat resistance of the resultant optical film or adjusting the photoelastic coefficient, the (meth)acrylic resin preferably contains a lactone ring structure. The lactone ring structure contained in the (meth)acrylic resin is preferably represented by the following General Formula (1):

[Chemical Formula 5]

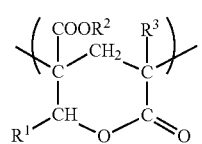

(1)

In Formula (1), $R^1$ to $R^3$ each independently represent a hydrogen atom or an organic residue having 1 to 20 carbon atoms. The organic residue may contain an oxygen atom. Examples of the organic residue include a linear or branched alkyl group, a linear or branched alkylene group, an aryl group, a —OAc group (wherein Ac represents an acetyl group), and a —CN group. The lactone ring structure represented by Formula (1) is a structure derived from an alkyl(meth)acrylate having a hydroxyl group, as will be described below.

The (meth)acrylic resin containing a lactone ring structure further contains a constituent unit derived from an alkyl (meth)acrylate having an alkyl moiety with 1 to 18 carbon atoms, and may optionally further contain a constituent unit derived from a monomer containing a hydroxyl group, an unsaturated carboxylic acid, a monomer represented by General Formula (2), or the like. $R^4$ in General Formula (2) represents a hydrogen atom or a methyl group. X represents a hydrogen atom, an alkyl group having 1 to 20 carbon atoms, an aryl group, an —OAc group (Ac: acetyl group), a —CN group, an acyl group, or a —C—OR group (wherein R represents a hydrogen atom, or an organic residue having 1 to 20 carbon atoms).

[Chemical Formula 6]

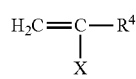

(2)

The proportion of the lactone ring structure represented by Formula (1) in the (meth)acrylic resin containing a lactone ring structure is preferably 5% to 90% by mass, more preferably 10% to 80% by mass, and even more preferably 15% to 70% by mass. If the proportion of the lactone ring structure is more than 90% by mass, molding processability is poor, and flexibility of the resultant film is also likely to be low. If the proportion of the lactone ring structure is less than 5% by mass, it is difficult to obtain a film having the required retardation, and the film may not have sufficient heat resistance, solvent resistance, and surface hardness.

The proportion of the constituent unit derived from an alkyl(meth)acrylate in the (meth)acrylic resin containing a lactone ring structure is preferably 10% to 95% by mass, more preferably 20% to 90% by mass, and even more preferably 30% to 85% by mass.

The proportions of the constituent unit derived from a hydroxyl group-containing monomer, an unsaturated carboxylic acid, and a monomer represented by General Formula (2) in the (meth)acrylic resin containing a lactone ring structure are each independently preferably 0% to 30% by mass, more preferably 0% to 20% by mass, and even more preferably 0% to 10% by mass.

The (meth)acrylic resin containing a lactone ring structure can be produced by subjecting monomers components including at least an alkyl(meth)acrylate having a hydroxyl group and other alkyl(meth)acrylate(s) to a polymerization reaction to obtain a polymer having hydroxyl groups and ester groups in the molecular chain; and heat treating the polymer thus obtained and thereby introducing a lactone ring structure thereto.

The weight average molecular weight Mw of the (meth) acrylic resin is preferably in the range of $8.0 \times 10^4$ to $5.0 \times 10^5$, more preferably in the range of $9.0 \times 10^4$ to $4.5 \times 10^5$, and even more preferably in the range of $1.0 \times 10^5$ to $4.0 \times 10^5$. If the weight average molecular weight Mw of the (meth)acrylic resin is less than $8.0 \times 10^4$, brittleness of the resultant film is prone to increase, and if the weight average molecular weight is more than $5.0 \times 10^5$, the haze value of the resultant film is prone to increase.

The weight average molecular weight Mw of the (meth) acrylic resin can be measured by gel permeation chromatography. Measurement conditions are as follows:
Solvent: Methylene chloride
Column: Shodex K806, K805, K803G (manufactured by Showa Denko KK. Three columns are used in connection.)
Column temperature: 25° C.
Sample concentration: 0.1% by weight
Detector: RI Model 504 (manufactured by GL Sciences Inc.)
Pump: L6000 (manufactured by Hitachi Ltd.)
Flow rate: 1.0 ml/min
Calibration curve: A calibration curve based on 13 samples of Mw=2,800,000 to 500 STK standard polystyrene (manufactured by Tosoh Corporation). It is preferred that the molecular weights of the 13 samples are approximately equally spaced.

The (meth)acrylic resin may be of a single kind, or may be a mixture of two or more kinds.

The thermoplastic resin may be of a single kind, or may be a mixture of two or more kinds. Examples of the mixture of two or more kinds include a mixture of a cellulose derivative and another resin; and examples of the other resin include vinyl-based resins (also including a polyvinyl acetate-based resin, a polyvinyl alcohol-based resin, and the like), cyclic olefin resins, polyester-based resins (aromatic polyesters, aliphatic polyesters, or copolymers containing those), and (meth)acrylic resins (also including copolymers).

The content of the other resin in the mixture of a cellulose derivative and another resin is preferably about 5% to about 70% by mass relative to the total amount of the mixture.

Regarding Compound Used in Present Invention

The inventors of the present invention found that a compound having an aspect ratio in a particular range and exhibiting a particular absorption maximum in a solution absorption spectrum, exhibits high retardation development properties and sufficient reverse wavelength dispersion characteristics.

That is, the compound used in the present invention is characterized by satisfying all of the following requirements (1) to (5):

(1) the compound has at least two absorption maxima in the wavelength region of from 200 nm to 350 nm in a solution absorption spectrum;

(2) when the wavelength of a first absorption maximum between the two absorption maxima in the wavelength region of from 200 nm to 350 nm is designated as $\lambda$max1, and the wavelength of a second absorption maximum at shorter wavelengths than the first absorption maximum is designated as $\lambda$max2, ($\lambda$max1−$\lambda$max2) is 20 nm or more;

(3) the aspect ratio of the molecule is 1.70 or more;

(4) the compound has at least one non-aromatic hydrocarbon ring, aromatic heterocyclic ring or non-aromatic heterocyclic ring in the molecule; and (5) the in-plane retardation increase sensitivity of a film having the compound added in an amount of 1% by mass with respect to the thermoplastic resin is 0.1 or more.

Requirements (1) and (2):

In order to develop high retardation even if the film thickness is small, and to obtain favorable wavelength dispersibility, the compound used in the present invention has at least two absorption maxima in the wavelength region of from 200 nm to 350 nm in a solution absorption spectrum. Further, the compound is characterized in that the two absorption maxima are separated apart over a certain distance in the wavelength region of from 200 nm to 350 nm; and specifically, when the wavelength of the first absorption maximum at longer wavelengths is designated as $\lambda$max1, and the wavelength of the second absorption maximum at shorter wavelengths is designated as $\lambda$max2, ($\lambda$max1−$\lambda$max2) is 20 nm or more, and more preferably 50 nm or more.

In the present invention, when three or more absorption maxima are identified in the wavelength region of from 200 nm to 350 nm, two absorption maxima having the longest wavelengths among them are selected; of them, the absorption maximum at longer wavelengths is designated as "first absorption maximum" and the absorption maximum at shorter wavelengths is designated as "second absorption maximum". Furthermore, even if a plurality of absorption maxima are present, if the difference between their wavelengths is less than 20 nm, the wavelength of an absorption having the highest absorbance among them is regarded as the absorption maximum, and other absorptions are not regarded as absorption maxima.

Figure 1B:
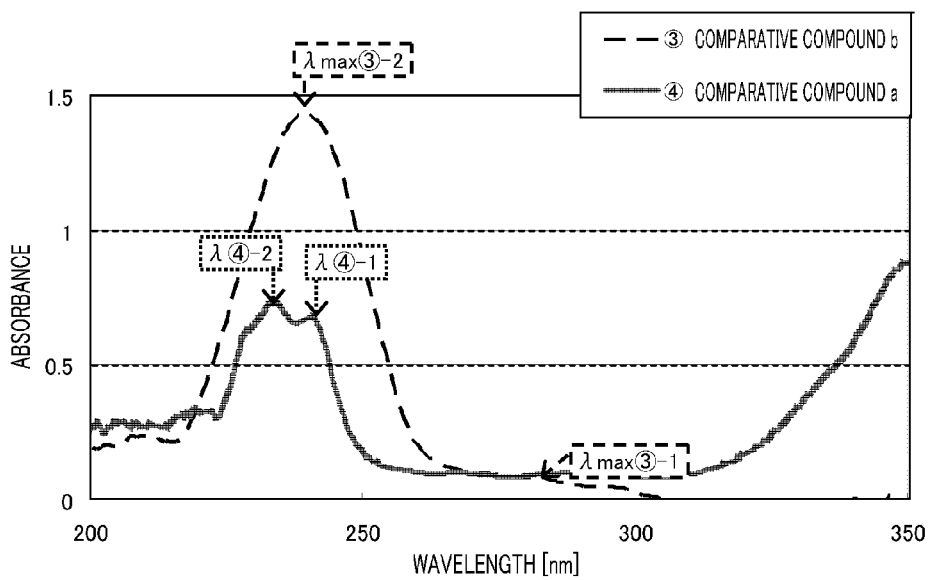

FIGS. 1A and 1B show graphs illustrating examples of solution absorption spectra of the compounds used in the present invention and compounds that are conventionally used. In these drawings, FIG. 1A is a graph showing solution absorption spectra of Compounds A-41 and A-62 (both compounds described in the specific examples described below) used in the present invention; and FIG. 1B is a graph showing solution absorption spectra of Comparative Compound b and Comparative Compound a (both compounds used in Comparative Examples described below) that are conventionally used.

As shown in FIG. 1B, the conventionally used Comparative Compound b and Comparative Compound a each have only one absorption maximum wavelength in the wavelength region of from 200 nm to 350 nm. Therefore, it is speculated that a balance between the retardation development properties and the wavelength dispersion characteristics cannot be achieved.

By contrast, as shown in FIG. 1A, the Compounds A-41 and A-62 used in the present invention have, in the wavelength region of from 200 nm to 350 nm, a first absorption maximum at longer wavelengths and a second absorption maximum at shorter wavelengths; and the first absorption maximum and the second absorption maximum are separated apart over a certain distance. Therefore, it is speculated that a balance can be achieved between the retardation development properties and the wavelength dispersion characteristics without cancelling each other (without trading-off).

When the absorbance of the first absorption maximum at the wavelength of λmax1 is designated as Abs1, and the absorbance of the second absorption maximum at the wavelength of λmax2 is designated as Abs2, the ratio of the absorbances, Abs1/Abs2, is preferably 0.08 to 20. If the ratio Abs1/Abs2 is less than 0.08, the resulting film may not exhibit sufficient reverse wavelength dispersibility. On the other hand, if the ratio Abs1/Abs2 is more than 20, the retardation development properties of the compound may not be sufficient. The ratio of absorbances, Abs1/Abs2, is more preferably 0.10 to 10.

The compound used in the present invention may have an absorption maximum in the region of 351 nm or longer. However, from the viewpoint of maintaining the light resistance of the film, it is preferable that the absorbance Abs3 at the wavelength of λmax3 of the absorption maximum at 351 nm or longer be smaller than Abs1 and Abs2, and it is more preferable that the compound do not have an absorption maximum in the region of 351 nm or longer.

A solution absorption spectrum may be obtained using a spectrophotometer for a solution obtained by dissolving the compound used in the present invention in solvent.

The solvent may be any solvent capable of dissolving the compound used in the present invention, and specific examples thereof include acetone, acetonitrile, tetrahydrofuran, ethyl acetate, methylene chloride, methanol, ethanol, and propanol. The concentration of the compound used in the present invention in the solution is not particularly limited, but the concentration can be preferably adjusted to about $10^{-8}$ to $10^{-3}$ mol/L. For the spectrophotometer, a commercially available spectrometer can be used.

Requirement (3):

The compound used in the present invention is characterized in that the aspect ratio of the molecule is 1.70 or more. When a compound having an aspect ratio of 1.70 or more is used, the compound is anisotropic with respect to the resin, so that the effect of increasing the reverse wavelength dispersibility may be easily obtained, and sufficiently high retardation development properties can be achieved even if the film thickness of the film is small. If the aspect ratio of the molecule is less than 1.70, retardation may be developed; however, the effect of increasing the reverse wavelength dispersibility may not be easily obtained. This is speculated to be because, since the molecular shape is close to a disc shape, the compound is isotropic with respect to the resin, and the effect of increasing the reverse wavelength dispersibility may not be easily obtained. Furthermore, for the compound of the present invention, the aspect ratio is preferably 10 or less. If the aspect ratio is too high, the compound's solubility in solvent becomes poor, and there may be a problem with handleability during production. The aspect ratio is more preferably 5 or less.

The aspect ratio of the compound can be determined by calculation using Winmostar MOPAC AM1 (MOP6W70) (Senda, "Bunshi Keisan Shien Shistemu Winmostar no Kaihatsu (Development of Molecular Computation Support System Winmostar", Idemitsu Giho, 49, 1, 106-111 (2006)).

Requirement (5):

The compound used in the present invention is characterized in that the in-plane retardation increase sensitivity is 0.1 or more, and the value is more preferably 0.12 or more. As used herein "in-plane retardation increase sensitivity" represents, when a film having the compound used in the present invention added in an amount of 1% by mass with respect to the thermoplastic resin is stretched under predetermined conditions, the proportion of the increment of the retardation in the in-plane direction with respect to the stretch ratio.

If the in-plane retardation increase sensitivity of the compound is less than 0.10, it is necessary to increase the content of the compound in the film, or to increase the thickness of the film, in order to develop a predetermined retardation. If the content of the compound in the film is too large, the film is prone to cause bleed-out, or the haze is prone to increase; and if the thickness of the film is too large, since the film is likely to be affected by the retardation in the thickness direction, color changes occur in an oblique direction of the display device, and visibility in the oblique direction is prone to decrease.

Measurement of the in-plane retardation increase sensitivity can be carried out by the following procedure.

1) A film having a thickness of 60 μm, which contains a thermoplastic resin and the compound used in the present invention in an amount of 1% by mass with respect to the thermoplastic resin, is produced, the film thus obtained is cut to a size of 50 mm×50 mm, and this is used as a sample film. Four points in total, that is, two points in the longitudinal direction each 15 mm away from the center of the sample film, and two points in the transverse direction each 15 mm away from the center, are used as the measurement points. Then, the distance between measurement points in the longitudinal direction (X0) and the distance between the measurement point in the transverse direction (Y0) before stretching, and the retardation in the in-plane direction at the wavelength of 550 nm at the central area surrounded by the measurement points, $R_0A0(550)$, are measured.

2) Subsequently, the sample film is subjected to uniaxial stretching in the transverse direction at a set ratio of 100% (stretch ratio: 2.0 times) at a temperature of (glass transition temperature (Tg) of the film+25° C.). For the sample film obtained after stretching, the distance between the measurement points in the longitudinal direction (X1) and the distance between the measurement points in the transverse direction (Y1) after stretching, and the retardation in the in-plane direction at the central area surrounded by the measurement points, $R_0A1(550)$, are measured.

3) The ratio at which the film has been actually stretched (actual stretch ratio) is calculated from the distance between the measurement points in the longitudinal direction (X1) and the distance between the measurement points in the transverse direction (Y1) after stretching, and the distance between the measurement points in the longitudinal direction (X0) and the distance between the measurement points in the transverse direction (Y0) before stretching.

$$\text{Actual stretch ratio } (\%) = [(Y1-Y0)/Y0 + (X0-X1)/X0] \times 100$$

Furthermore, the amount of retardation changed by stretching ($\Delta R_0A = R_0A1(550) - R_0A0(550)$) is calculated from the retardation in the in-plane direction after stretching $R_0A1(550)$ and the retardation in the in-plane direction before stretching $R_0A0(550)$. Then, the $\Delta R_0A$ thus obtained is divided by the actual stretch ratio, and thus the in-plane retardation sensitivity A of the film is calculated.

$$A = \Delta R_0 A / \text{actual stretch ratio } (\%)$$

4) On the other hand, a film having a thickness of 60 μm and formed from a thermoplastic resin is produced in the same manner as in the above section 1), except that the compound used in the present invention is not incorporated; the film thus obtained is cut to a size of 50 mm×50 mm to prepare a blank film. The in-plane retardation sensitivity B of this blank film is measured in the same manner as described above.

Then, the in-plane retardation sensitivity A obtained in the above section 3) and the in-plane retardation sensitivity B obtained in the above section 4) are applied to the following formula, and thereby, the in-plane retardation increase sensitivity is determined In-plane retardation increase sensitivity=(in-plane retardation sensitivity A of sample film)−(in-plane retardation sensitivity B of blank film)

The glass transition temperature (Tg) of the film can be measured by a differential scanning calorimetric method using, for example, a commercially available apparatus such as a DSC-7 differential scanning calorimeter (manufactured by PerkinElmer, Inc.) or a TAC 7/DX thermal analysis controller (manufactured by PerkinElmer, Inc.).

1) 4.5 mg to 5.0 mg of the resin is weighed precisely to the order of 0.01 mg, the resin is sealed in an aluminum pan, and the pan is mounted on a sample holder of DSC-7 differential scanning calorimeter (manufactured by PerkinElmer, Inc.). An empty aluminum pan is used as a reference.

2) The analysis is carried out by temperature control of Heat-Cool-Heat under the conditions of a measurement temperature of 0° C. to 200° C., a temperature increase rate of 10° C./min, and a temperature decrease rate of 10° C./min. Then, the glass transition temperature is determined based on the data for the $2^{nd}$ Heat stage. Specifically, an intersection of an extended line of the base line before the rise of a first endothermic peak, and a tangent line representing the maximum gradient drawn between the rise portion of the first endothermic peak and the peak apex, is designated as the glass transition temperature (Tg).

Requirement (4):

The compound used in the present invention is characterized by having at least one non-aromatic hydrocarbon ring, aromatic heterocyclic ring or non-aromatic heterocyclic ring in the molecule.

Examples of the non-aromatic hydrocarbon ring include cyclopropane ring, cyclobutane ring, cyclopentane ring, cyclohexane ring, cycloheptane ring, cyclooctane ring, cyclobutene ring, cyclopentene ring, cyclohexene ring, cycloheptene ring, cyclooctene ring, adamantane ring, bicyclononane ring, norbornane ring, norbornene ring, dicyclopentadiene ring, hydrogenated naphthalene ring, and hydrogenated biphenyl ring. Among them, cyclopentane ring, cyclohexane ring, cycloheptane ring, cyclonorbornene ring and the like are preferred.

Examples of the aromatic heterocyclic ring include furan ring, benzofuran ring, thiophene ring, benzothiophene ring, pyrrole ring, pyrazole ring, imidazole ring, oxadiazole ring, indole ring, carbazole ring, azacarbazole ring (azacarbazole ring group represents a group in which one or more of the carbon atoms that constitute a carbazole ring group have been substituted by nitrogen atoms), triazole ring, pyrroloimidazole ring, pyrrolopyrazole ring, pyrrolopyrrole ring, thienopyrrole ring, thienothiophene ring, furopyrrole ring, furofuran ring, thienofuran ring, benzisoxazole ring, benzisothiazole ring, benzimidazole ring, pyridine ring, pyrazine ring, pyridazine ring, pyrimidine ring, triazine ring, quinoline ring, isoquinoline ring, cinnoline ring, quinoxaline ring, phenanthridine ring, benzimidazole ring, perimidine ring, quinazoline ring, quinazolinone ring, azulene ring, silole ring, dibenzofuran ring, dibenzothiophene ring, dibenzocarbazole ring, benzodifuran ring, benzodithiophene ring, phenanthroline ring, acridine ring, benzoquinoline ring, phenazine ring, phenanthridine ring, phenanthroline ring, cyclazine ring, quindoline ring, tepenidine ring, quinindoline ring, triphenodithiazine ring, triphenodioxazine ring group, phenanthrazine ring group, anthrazine ring group, perimidine ring group, naphthofuran ring, naphthothiophene ring, naphthodifuran ring, naphthodithiophene ring, anthrafuran ring, anthradifuran ring, and anthrathiophene ring. Among them, pyridine ring, benzothiazole ring, benzoxazole ring and the like are preferred.

Examples of the non-aromatic heterocyclic ring include tetrahydrofuran ring, tetrahydropyrane ring, dioxolane ring, dioxane ring, pyrrolidine ring, pyridone ring, pyridazinone ring, imide ring, piperidine ring, dihydropyrrole ring, dihydropyridine ring, tetrahydropyridine ring, piperazine ring, morpholine ring, dihydrooxazole ring, dihydrothiazole ring, piperidine ring, aziridine ring, azetidine ring, azepine ring, azepane ring, imidazolidine ring, diazepine ring, and tetrahydrothiophene ring. Among them, pyridone ring, imide ring, and pyrrolidine ring are preferred.

Since a compound having an aromatic heterocyclic ring or a non-aromatic heterocyclic ring in the molecule contains the heteroatoms of the heterocyclic ring, the compound's compatibility with thermoplastic resins can be enhanced. Thereby, the compound can easily interact with a thermoplastic resin, and can easily develop higher retardation. Particularly, since a non-aromatic heterocyclic ring has a molecular structure having higher flexibility than an aromatic heterocyclic ring, a non-aromatic heterocyclic ring can interact more easily with a thermoplastic resin than an aromatic heterocyclic ring, and can easily develop a higher retardation. On the other hand, since a compound having only a chain-like structure containing a heteroatom has excessively high molecular flexibility, molecular movement becomes active at the time of heating and stretching of the optical film, and the molecules are immobilized without being oriented (being random) at the time of cooling. Therefore, it is difficult for the compound to interact with a thermoplastic resin, and may not easily develop retardation.

Furthermore, since a non-aromatic hydrocarbon ring does not have a fixed ring structure, the non-aromatic hydrocarbon ring can change the structure flexibly according to the molecular structure of the thermoplastic resin. Furthermore, since the non-aromatic hydrocarbon ring does not have flexibility to the extent of that of a chain-like structure, the non-aromatic ring hydrocarbon ring may interact easily with a thermoplastic resin and can easily develop high retardation.

On the other hand, a compound which does not contain an aromatic heterocyclic ring, a non-aromatic heterocyclic ring and or a non-aromatic hydrocarbon ring but has an aromatic hydrocarbon ring only as the cyclic structure, cannot easily interact with a resin, and neither retardation nor wavelength dispersibility can be easily improved. Also, a compound having an aromatic hydrocarbon ring only has poor compatibility with a resin.

It is preferable that the compound used in the present invention contain one or more non-aromatic rings (non-aromatic hydrocarbon rings or non-aromatic heterocyclic rings) in the molecule.

The inventors of the present invention paid attention to a compound having absorption maxima that at least satisfy (1) and (2) in a solution absorption spectrum, and having a cyclic group around which substituents can be relatively freely disposed (Q that will be described below) as a mother nucleus. Then, the inventors conducted various investigations by varying the kind and combination of substituents, and as a result, the inventors found that when two substituents that are bonded to adjacent atoms among the atoms that constitute the cyclic group (Q that will be described below), are different from each other, the compound has absorption maxima that satisfy the requirements (1) and (2) described above, and exhibits high retardation development properties and wavelength dispersibility.

The compound used in the present invention is preferably a compound represented by the following General Formula (A):

[Chemical Formula 7]

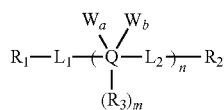

General Formula (A)

Q in General Formula (A) represents an aromatic hydrocarbon ring, a non-aromatic hydrocarbon ring, an aromatic heterocyclic ring, or a non-aromatic heterocyclic ring.

The aromatic hydrocarbon ring may be monocyclic or may be a condensed ring, but is preferably monocyclic. Preferred examples of the aromatic hydrocarbon ring include benzene ring, naphthalene ring, anthracene ring, phenanthrene ring, perylene ring, tetracene ring, pyrene ring, benzopyrene ring, chrysene ring, triphenylene ring, acenaphthene ring, fluoranthene ring, and fluorene ring. The aromatic hydrocarbon ring is more preferably benzene ring.

The non-aromatic hydrocarbon ring has the same definition as described above, but preferred examples include cyclopropane ring, cyclobutane ring, cyclopentane ring, cyclohexane ring, cycloheptane ring, cyclooctane ring, and norbornene ring. More preferred examples include cyclohexane ring and cyclopentane ring.

The aromatic heterocyclic ring has the same definition as described above, and may be monocyclic or may be a condensed ring. The aromatic heterocyclic ring is preferably monocyclic. Preferred examples of the aromatic heterocyclic ring include furan ring, benzofuran ring, thiophene ring, benzothiophene ring, pyrrole ring, pyrazole ring, imidazole ring, oxadiazole ring, indole ring, carbazole ring, triazole ring, benzimidazole ring, pyridine ring, pyrazine ring, pyridazine ring, pyrimidine ring, triazine ring, quinoline ring, benzimidazole ring, perimidine ring, quinazoline ring, azulene ring, dibenzofuran ring, dibenzothiophene ring, dibenzocarbazole ring, benzodifuran ring, benzodithiophene ring, and phenanthroline ring. More preferred examples thereof include pyridine ring, a benzothiazole ring, and benzoxazole ring.

The non-aromatic heterocyclic ring has the same definition as described above, but preferred examples thereof include tetrahydrofuran ring, tetrahydropyrane ring, dioxolane ring, dioxane ring, pyrrolidine ring, pyridone ring, pyridazinone ring, imide ring, piperidine ring, dihydropyrrole ring, dihydropyridine ring, tetrahydropyridine ring, piperazine ring, morpholine ring, and piperidine ring. More preferred examples include pyridone ring, imide ring, and pyrrolidine ring.

$W_a$ and $W_b$ in General Formula (A) each represent a hydrogen atom or a substituent, each being bonded to an atom that constitutes the ring of Q (ring-constituting atom); and the ring-constituting atom to which $W_a$ is bonded, and the ring-constituting atom to which $W_b$ is bonded are adjacent to each other. $W_a$ and $W_b$ are different from each other.

The substituents represented by $W_a$ and $W_b$ have a function of mainly imparting reverse wavelength dispersibility to the compound, and specifically, it is preferable that the substituents have a structure which causes an absorption maximum at longer wavelengths.

It is preferable that $W_a$ and $W_b$ be bonded to each other and form a ring; or at least one of $W_a$ and $W_b$ have a cyclic structure.

Examples of the substituent represented by $W_a$ or $W_b$ include:

halogen atoms (fluorine atom, chlorine atom, bromine atom, iodine atom, or the like), an alkyl group (methyl group, ethyl group, n-propyl group, isopropyl group, tert-butyl group, n-octyl group, 2-ethylhexyl group, or the like), a cycloalkyl group (cyclohexyl group, cyclopentyl group, 4-n-dodecylcyclohexyl group, or the like), an alkenyl group (vinyl group, allyl group, or the like), a cycloalkenyl group (2-cyclopenten-1-yl group, 2-cyclohexen-1-yl group, or the like), an alkynyl group (ethynyl group, propargyl group, or the like), an aryl group (phenyl group, p-tolyl group, naphthyl group, or the like), a heteroaryl group (2-pyrrole group, 2-furyl group, 2-thienyl group, pyrrole group, imidazolyl group, oxazolyl group, thiazolyl group, benzimidazolyl group, benzoxazolyl group, 2-benzothiazolyl group, pyrazolinone group, pyridyl group, pyridinone group, 2-pyrimidinyl group, or the like), cyano group, hydroxyl group, nitro group, carboxyl group, an alkoxy group (methoxy group, ethoxy group, isopropoxy group, tert-butoxy group, an n-octyloxy group, 2-methoxyethoxy group, or the like), an aryloxy group (phenoxy group, 2-methylphenoxy group, 4-tert-butylphenoxy group, 3-nitrophenoxy group, 2-tetradecanoylaminophenoxy group, or the like), an acyl group (acetyl group, pivaloylbenzoyl group, or the like), an acyloxy group (formyloxy group, acetyloxy group, pivaloyloxy group, stearoyloxy group, benzoyloxy group, p-methoxyphenylcarbonyloxy group, or the like), an amino group (amino group, methylamino group, dimethylamino group, anilino group, N-methylanilino group, diphenylamino group, or the like), an acylamino group (formylamino group, acetylamino group, pivaloylamino group, lauroylamino group, benzoylamino group, or the like), an alkyl- or arylsulfonylamino group (methylsulfonylamino group, butylsulfonylamino group, phenylsulfonylamino group, 2,3,5-trichlorophenylsulfonylamino group, p-methylphenylsulfonylamino group, or the like), mercapto group, an alkylthio group (methylthio group, ethylthio group, n-hexadecylthio group, or the like), an arylthio group (phenylthio group, p-chlorophenylthio group, m-methoxyphenylthio group, or the like), a sulfamoyl group (N-ethylsulfamoyl group, N-(3-dodecyloxypropyl)sulfamoyl group, N,N-dimethylsulfamoyl group, N-acetylsulfamoyl group, N-benzoylsulfamoyl group, N—(N'-phenylcarbamoyl)sulfamoyl group, or the like), sulfo group, and a carbamoyl group (carbamoyl group, N-methylcarbamoyl group, N,N-dimethylcarbamoyl group, N,N-di-n-octylcarbamoyl group, N-(methylsulfonyl)carbamoyl group, or the like).

It is preferable that $W_a$ and $W_b$ be bonded to each other and form a ring; or $W_a$ be a hydrogen atom, while $W_b$ be an aromatic hydrocarbon ring, a non-aromatic hydrocarbon ring, an aromatic heterocyclic ring, or a non-aromatic heterocyclic ring, and more preferably an aromatic heterocyclic ring. The ring formed by $W_a$ and $W_b$ bonded to each other is preferably an aromatic heterocyclic ring, and more preferably a nitrogen-containing heterocyclic ring, as described below.

$R_3$ in General Formula (A) represents any substituent, and may be present or may be absent. Examples of the substituent include, but are not particularly limited to:

a halogen atom (fluorine atom, chlorine atom, bromine atom, iodine atom, or the like), an alkyl group (methyl group, ethyl group, n-propyl group, isopropyl group, tert-butyl group, n-octyl group, 2-ethylhexyl group, or the like), an alkenyl group (vinyl group, allyl group, or the like), an alkynyl group (ethynyl group, propargyl group, or the like), cyano group, hydroxyl group, nitro group, carboxyl group, an alkoxy group (methoxy group, ethoxy group, isopropoxy group, tert-butoxy group, n-octyloxy group, 2-methoxyethoxy group, or the like), an acyloxy group (formyloxy group, acetyloxy group, pivaloyloxy group, stearoyloxy group, or the like), an alkoxycarbonyl group (methoxycarbonyl group, ethoxycarbonyl group, or the like), an aryloxycarbonyl group (phenoxycarbonyl group, or the like), an amino group (amino group, methylamino group, dimethylamino group, or the like), an acylamino group (formylamino group, acetylamino group, pivaloylamino group, lauroylamino group, or the like), an alkylsulfonylamino group (methylsulfonylamino group, butylsulfonylamino group, or the like), mercapto group, an alkylthio group (methylthio group, ethylthio group, n-hexadecylthio group, or the like), a sulfamoyl group (N-ethylsulfamoyl group, N-(3-dodecyloxypropyl)sulfamoyl group, N,N-dimethylsulfamoyl group, N-acetylsulfamoyl group, or the like), sulfo group, an acyl group (acetyl group, or the like), and a carbamoyl group (carbamoyl group, N-methylcarbamoyl group, N,N-dimethylcarbamoyl group, N,N-di-n-octylcarbamoyl group, N-(methylsulfonyl)carbamoyl group, or the like).

Among them, $R_3$ is preferably a hydrogen atom, a halogen atom, an alkyl group (preferably having 1 to 20 carbon atoms), an alkenyl group (preferably having 3 to 20 carbon atoms), an aryl group (preferably having 6 to 20 carbon atoms), a heteroaryl group (preferably having 4 to 20 carbon atoms), hydroxyl group, carboxyl group, an alkoxy group (preferably having 1 to 20 carbon atoms), an aryloxy group (preferably having 6 to 20 carbon atoms), an acyl group, an acyloxy group, a cyano group, or an amino group; and more preferably a hydrogen atom, a halogen atom, an alkyl group, a cyano group, or an alkoxy group. These substituents may further have similar substituents.

m in General Formula (A) is the number of substituents represented by $R_3$; and represents an integer from 0 to 2, and preferably 0. When m is 2, $R_3$'s may be identical with or different from each other.

n in General Formula (A) represents an integer from 1 to 10, and is preferably 1. When n is 2 or more, a plurality of Q's, $L_2$'s, $W_a$'s, $W_b$'s, $R_3$'s, and m's may be identical with or different from each other.

$L_1$ and $L_2$ in General Formula (A) each independently represent a single bond, or a divalent linking group selected from the group consisting of an alkylene group, an alkenylene group, an alkynylene group, —O—, —(C=O)—, —(C=O)—O—, —NR$_L$—, —S—, —(O=S=O)— and —(C=O)—NR$_L$—, or a combination thereof; and $L_1$ and $L_2$ are each preferably —O—, —(C=O)—O—, —O—(C=O)—, —(C=O)—NH—, or —NH—(C=O)—.

$R_L$ represents a hydrogen atom or a substituent. Examples of the substituent represented by $R_L$ include an alkyl group (methyl group, ethyl group, n-propyl group, isopropyl group, tert-butyl group, n-octyl group, 2-ethylhexyl group, or the like), a cycloalkyl group (cyclohexyl group, cyclopentyl group, 4-n-dodecylcyclohexyl group, or the like), an aryl group (phenyl group, p-tolyl group, naphthyl group, or the like), a heteroaryl group (2-furyl group, 2-thienyl group, 2-pyrimidinyl group, 2-benzothiazolyl group, 2-pyridyl group, or the like), and cyano group.

$R_1$ and $R_2$ in General Formula (A) each independently represent a substituent. $R_1$ and $R_2$ may be identical with or different from each other. Examples of the substituent represented by $R_1$ and $R_2$ include:

a halogen atom (fluorine atom, chlorine atom, bromine atom, iodine atom, or the like), an alkyl group (methyl group, ethyl group, n-propyl group, isopropyl group, tert-butyl group, n-octyl group, 2-ethylhexyl group, or the like), a cycloalkyl group (cyclohexyl group, cyclopentyl group, 4-n-dodecylcyclohexyl group, or the like), an alkenyl group (vinyl group, allyl group, or the like), a cycloalkenyl group (2-cyclopenten-1-yl group, 2-cyclohexen-1-yl group, or the like), an alkynyl group (ethynyl group, propargyl group, or the like), an aryl group (phenyl group, p-tolyl group, naphthyl group, or the like), a heteroaryl group (2-furyl group, 2-thienyl group, 2-pyrimidinyl group, 2-benzothiazolyl group, 2-pyridyl group, or the like), cyano group, hydroxyl group, nitro group, carboxyl group, an alkoxy group (methoxy group, ethoxy group, isopropoxy group, tert-butoxy group, n-octyloxy group, 2-methoxyethoxy group, or the like), an aryloxy group (phenoxy group, 2-methylphenoxy group, 4-tert-butylphenoxy group, 3-nitrophenoxy group, 2-tetradecanoylaminophenoxy group, or the like), an acyloxy group (formyloxy group, acetyloxy group, pivaloyloxy group, stearoyloxy group, benzoyloxy group, p-methoxyphenylcarbonyloxy group, or the like), an amino group (amino group, methylamino group, dimethylamino group, anilino group, N-methylanilino group, diphenylamino group, or the like), an acylamino group (formylamino group, acetylamino group, pivaloylamino group, lauroylamino group, benzoylamino group, or the like), an alkyl- or arylsulfonylamino group (methylsulfonylamino group, butylsulfonylamino group, phenylsulfonylamino group, 2,3,5-trichlorophenylsulfonylamino group, p-methylphenylsulfonylamino group, or the like), mercapto group, an alkylthio group (methylthio group, ethylthio group, an n-hexadecylthio group, or the like), an arylthio group (phenylthio group, p-chlorophenylthio group, m-methoxyphenylthio group, or the like), a sulfamoyl group (N-ethylsulfamoyl group, N-(3-dodecyloxypropyl)sulfamoyl group, N,N-dimethylsulfamoyl group, N-acetylsulfamoyl group, N-benzoylsulfamoyl group, N—(N'-phenylcarbamoyl)sulfamoyl group, or the like), sulfo group, an acyl group (acetyl group, pivaloylbenzoyl group, or the like), and a carbamoyl group (carbamoyl group, N-methylcarbamoyl group, N,N-dimethylcarbamoyl group, N,N-di-n-octylcarbamoyl group, N-(methylsulfonyl)carbamoyl group, or the like).

Among them, $R_1$ and $R_2$ are each preferably an alkyl group (preferably an alkyl group having 1 to 20 carbon atoms), a cycloalkyl group (preferably a cycloalkyl group having 3 to 20 carbon atoms), an aryl group (preferably an aryl group having 6 to 20 carbon atoms), or a heteroaryl group (preferably an aryl group having 4 to 20 carbon atoms); and more preferably an aryl group or a cycloalkyl group. The aryl group is preferably a substituted or unsubstituted phenyl group, more preferably a phenyl group having a substituent, and even more preferably a phenyl group having a substituent at the 4-position. The cycloalkyl group is preferably a substituted or unsubstituted cyclohexyl group, more preferably a cyclohexyl group having a substituent, and even more preferably a cyclohexyl group having a substituent at the 4-position. The substituent represented by $R_1$ or $R_2$ may further have a similar substituent.

The compound represented by General Formula (A) is preferably a compound represented by General Formula (B).

[Chemical Formula 8]

General Formula (B)

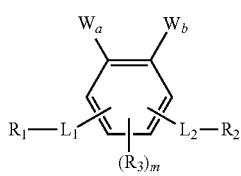

$W_a$, $W_b$, $R_3$, m, $L_1$, $L_2$, $R_L$, $R_1$ and $R_2$ in General Formula (B) have the same definitions as $W_a$, $W_b$, $R_3$, m, $L_1$, $L_2$, $R_L$, $R_1$ and $R_2$ in General Formula (A), respectively.

The compound represented by General Formula (B) is preferably a compound represented by General Formula (1B):

[Chemical Formula 9]

General Formula (1B)

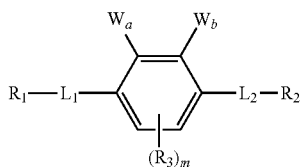

$W_a$, $W_b$, $R_3$, m, $L_1$, $L_2$, $R_L$, $R_1$, and $R_2$ in General Formula (1B) have the same definitions as $W_a$, $W_b$, $R_3$, m, $L_1$, $L_2$, $R_L$, $R_1$, and $R_2$ in General Formula (A), respectively.

$W_a$ and $W_b$ in General Formula (1B) may be bonded to each other and form a ring. The ring formed by $W_a$ and $W_b$ bonded to each other is preferably a nitrogen-containing heterocyclic ring. Examples of such a compound represented by General Formula (1B) include the following:

[Chemical Formula 10]

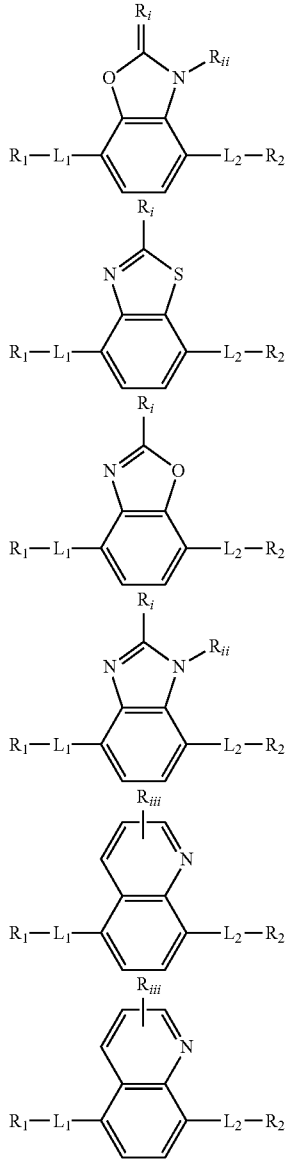

For example, in regard to a compound represented by the following formula, Q in General Formula (A) represents a benzene ring; $W_a$ represents a group containing an oxygen atom that is bonded to the benzene ring; and $W_b$ represents a group containing a nitrogen atom that is bonded to the benzene ring:

[Chemical Formula 11]

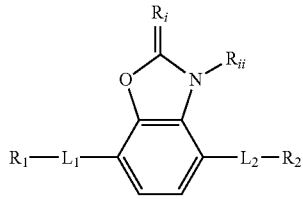

On the other hand, in regard to a compound represented by the following formula, Q in General Formula (A) represents a naphthalene ring:

[Chemical Formula 12]

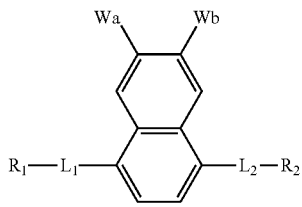

The compound represented by General Formula (B) is more preferably a compound represented by General Formula (2B):

[Chemical Formula 13]

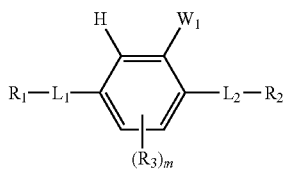

General Formula (2B)

$W_1$ in General Formula (2B) represents a cyclic group. The atom that is bonded to the benzene ring among the ring-constituting atoms of $W_1$ is preferably a carbon atom or a nitrogen atom. The cyclic group represented by $W_1$ is not particularly limited as long as it is any cyclic group, but specific examples include residues of aromatic heterocyclic rings such as pyrrole ring, furyl ring, thiophene ring, imidazole ring, oxazole ring, thiazole ring, benzimidazole ring, benzoxazole ring, benzothiazole ring, benzoxazinone ring, and pyridyl ring; residues of aromatic hydrocarbon rings such as benzene ring and naphthalene ring; residues of non-aromatic heterocyclic rings such as pyridone ring, pyridazinone ring, and imide ring; and residues of non-aromatic hydrocarbon rings such as cyclohexane ring and cyclopentane ring.

$R_3$, m, $L_1$, $L_2$, $R_L$, $R_1$ and $R_2$ in General Formula (2B) have the same definitions as $R_3$, m, $L_1$, $L_2$, $R_L$, $R_1$ and $R_2$ in General Formula (A), respectively.

Examples of the compound represented by General Formula (2B) include the following compounds:

[Chemical Formula 14]

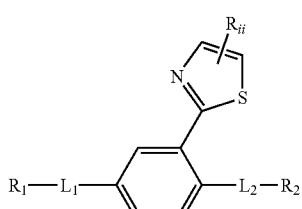

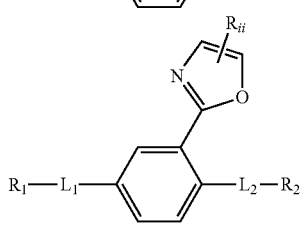

-continued

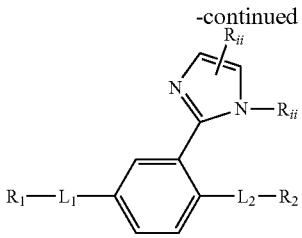

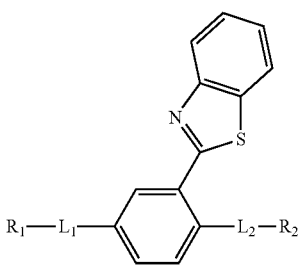

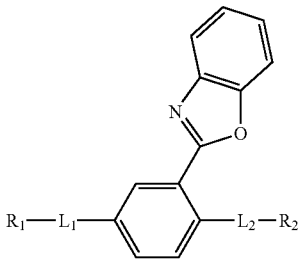

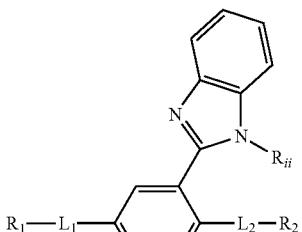

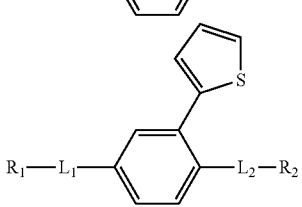

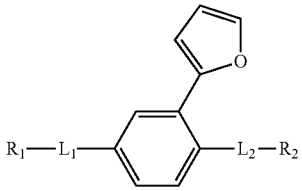

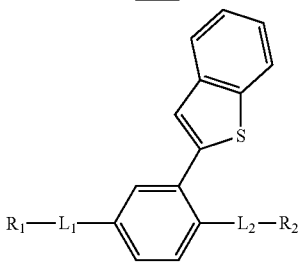

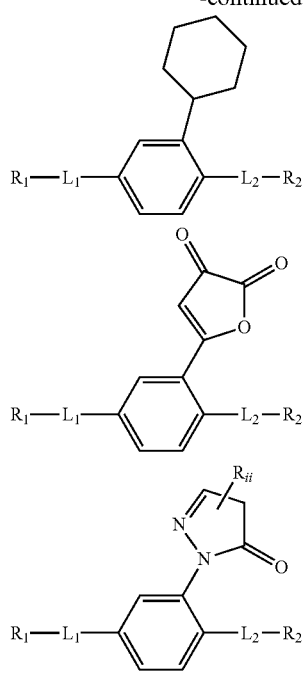
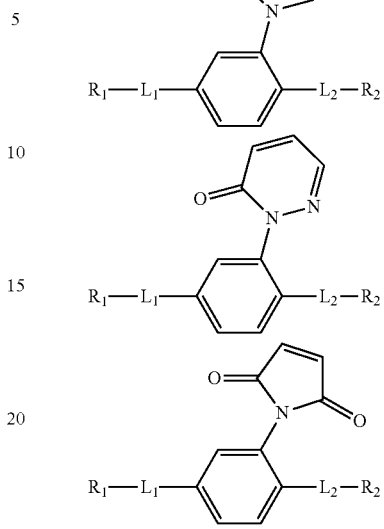
Specific examples of the compound represented by General Formula (A) include the following:

| Compound No. | $R_1$ | $L_1$ | $W_a$ $W_b$ $\underset{(R_3)_m}{\diagdown O \diagup}$ [Chemical Formula 15] | $L_2$ | $R_2$ | $n$ |
|---|---|---|---|---|---|---|
| A-1 | 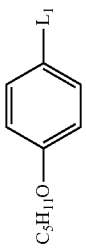 | 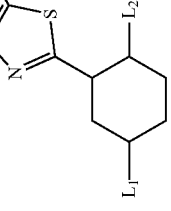 | 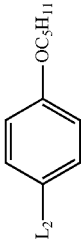 | 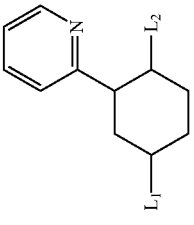 | 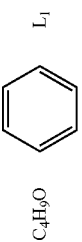 | 1 |
| A-2 | | | | | | 1 |
| A-3 | | | | | | 1 |

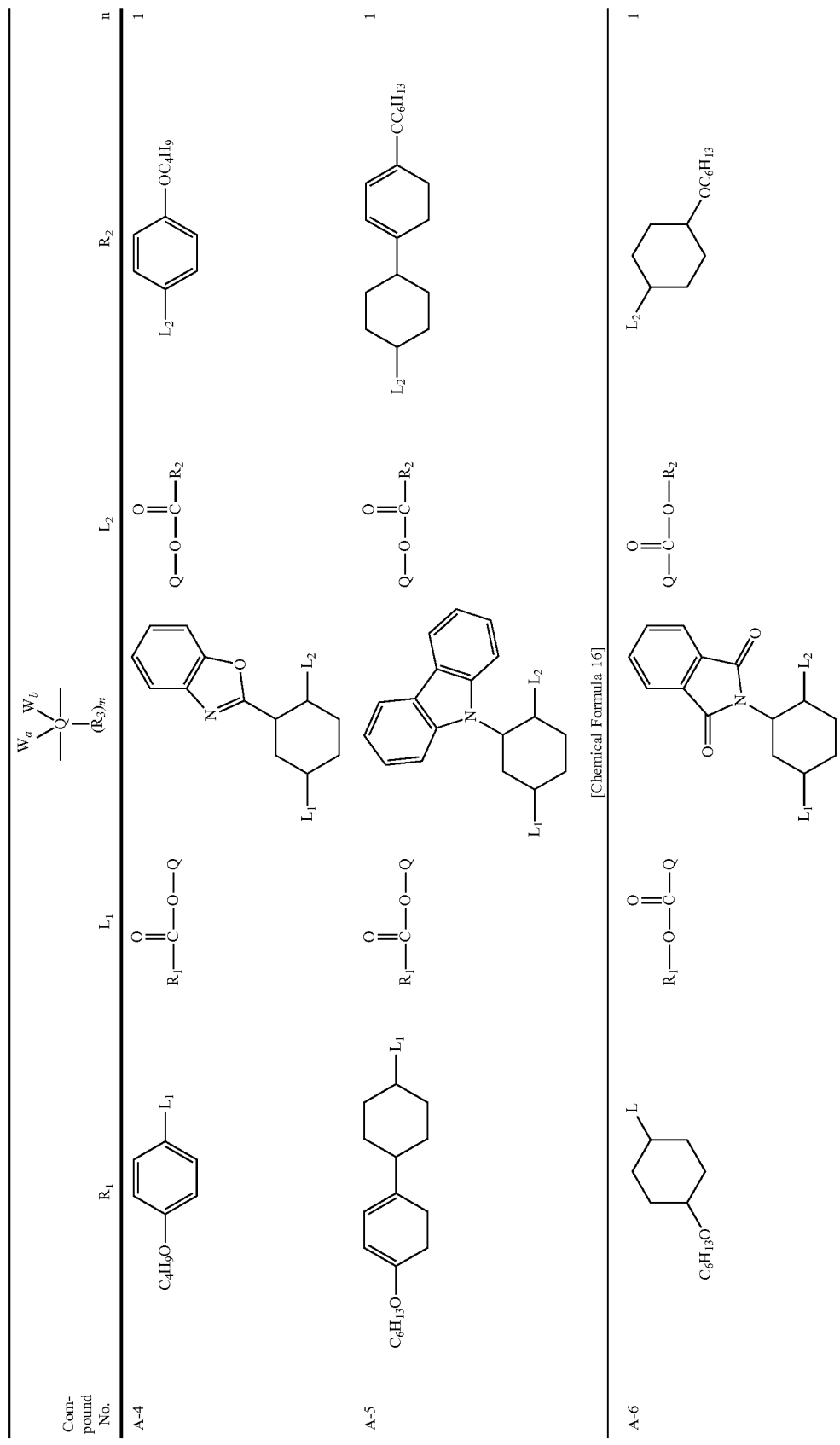

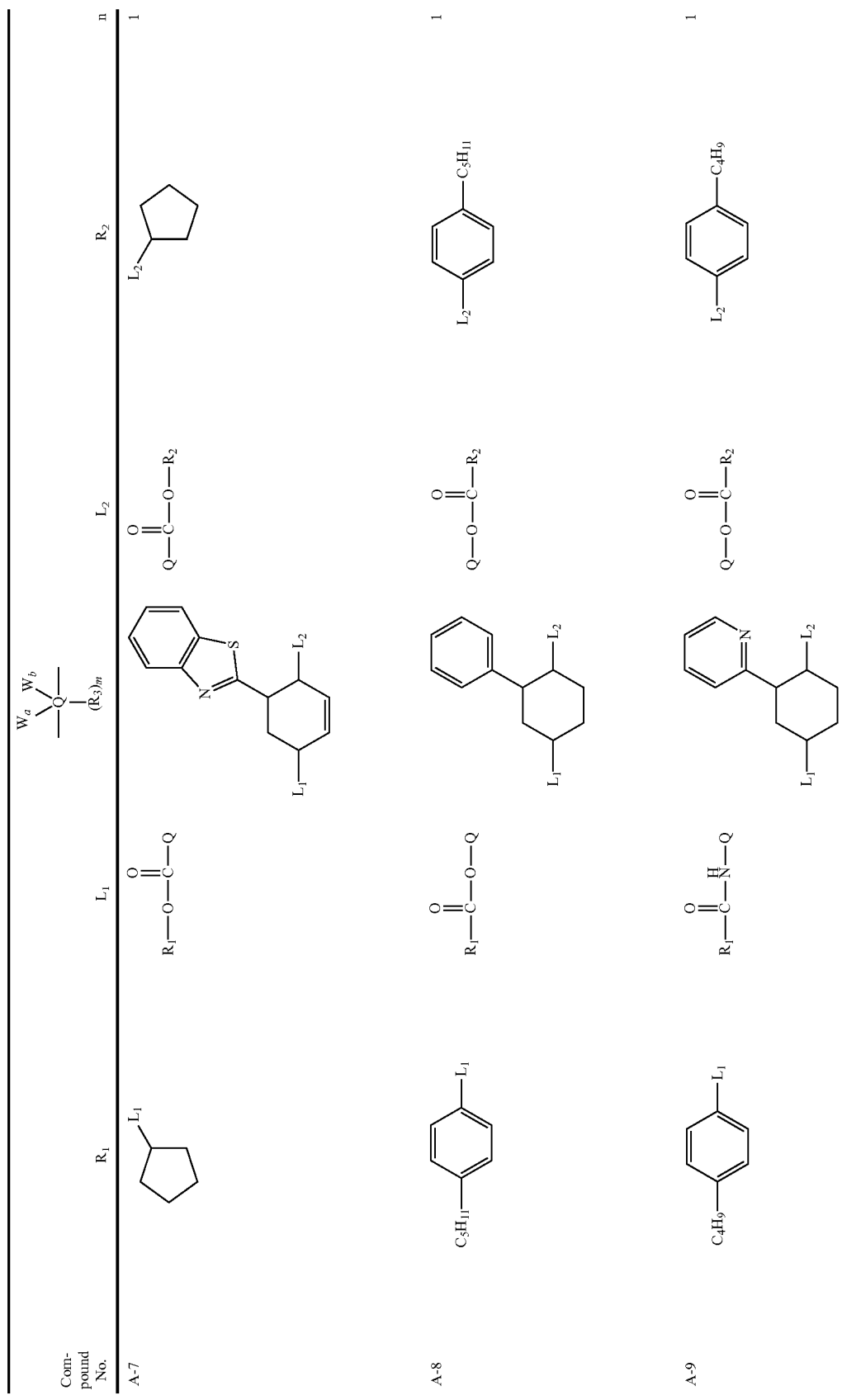

-continued

| Compound No. | $R_1$ | $L_1$ | $W_a$ $W_b$ — O — $(R_3)_m$ | $L_2$ | $R_2$ | n |
|---|---|---|---|---|---|---|
| A-10 | 4-C₈H₁₇-phenyl (L₁) | R₁—C(=O)—O—Q | benzotriazol-2-yl-cyclohexyl (L₁, L₂) | Q—O—C(=O)—R₂ | 4-C₄H₉-phenyl (L₂) | 1 |

[Chemical Formula 17]

| A-11 | 4-C₅H₁₁-phenyl (L₁) | R₁—C(=O)—O—Q | benzothiazol-2-yl-cyclohexyl (L₁, L₂) | Q—O—C(=O)—R₂ | 4-C₅H₁₁-phenyl (L₂) | 1 |
| A-12 | 4-C₈H₁₇-phenyl (L₁) | R₁—C(=O)—O—Q | pyridin-2-yl-cyclohexyl (L₁, L₂) | Q—O—C(=O)—R₂ | 4-C₈H₁₇-phenyl (L₂) | 1 |

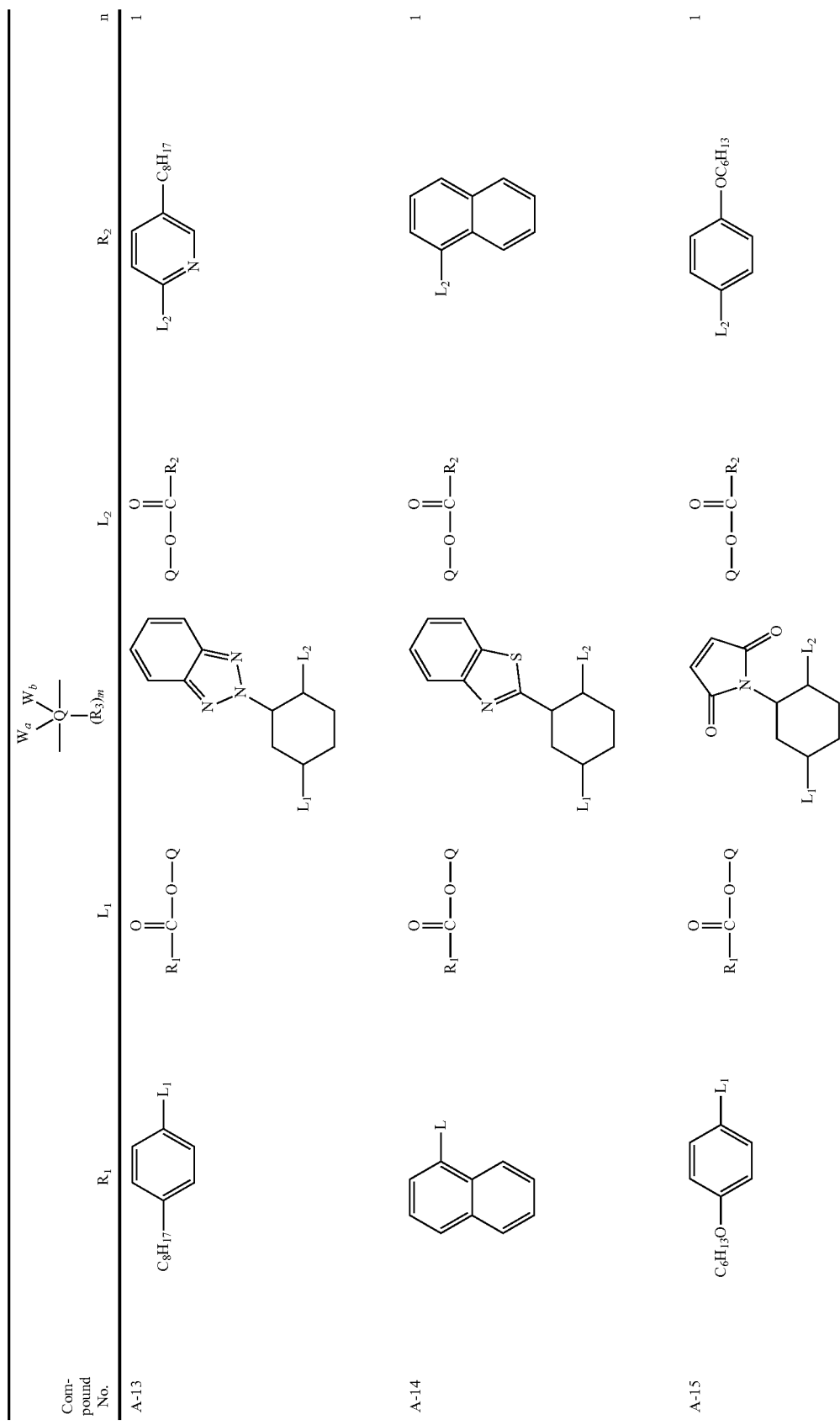

-continued
[Chemical Formula 18]
| Compound No. | R₁ | L₁ | $W_a$ $W_b$ / O (R₃)ₘ | L₂ | R₂ | n |
|---|---|---|---|---|---|---|
| A-16 | 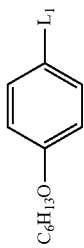 |  |  |  | 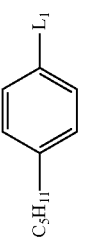 | 1 |
| A-17 | 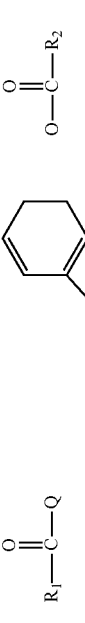 |  |  | 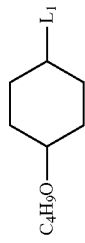 | 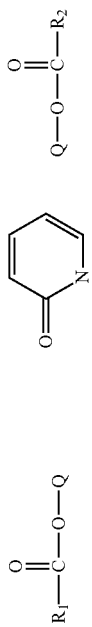 | 1 |
| A-18 |  | |  | | | 1 |

-continued
| Compound No. | $R_1$ | $L_1$ | $\underset{(R_3)_m}{W_a\ W_b}$ | $L_2$ | $R_2$ | n |
|---|---|---|---|---|---|---|
| A-19 | 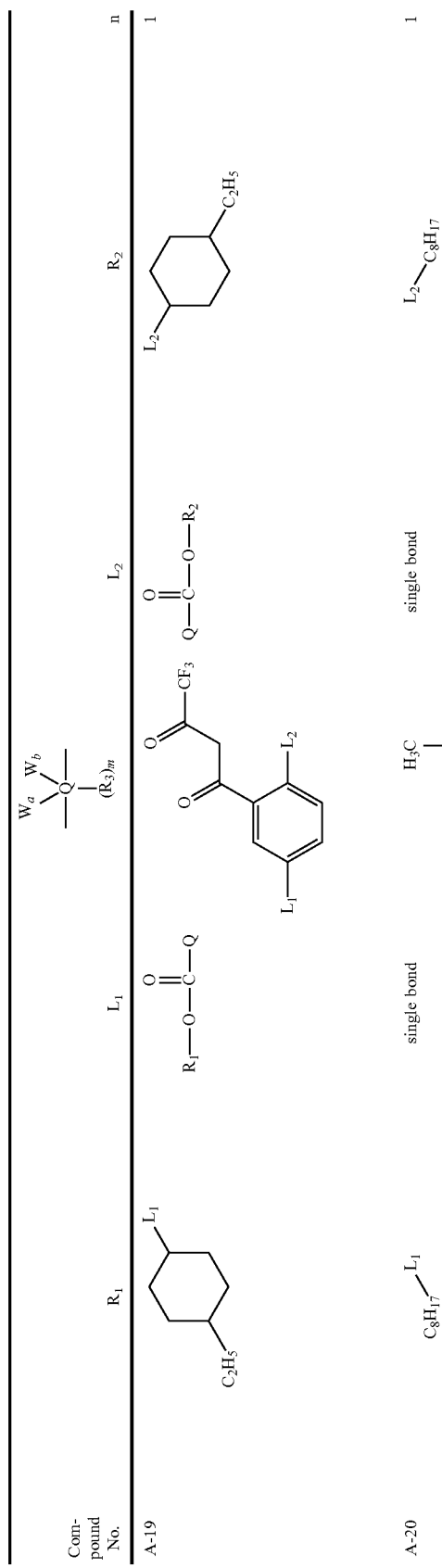 | 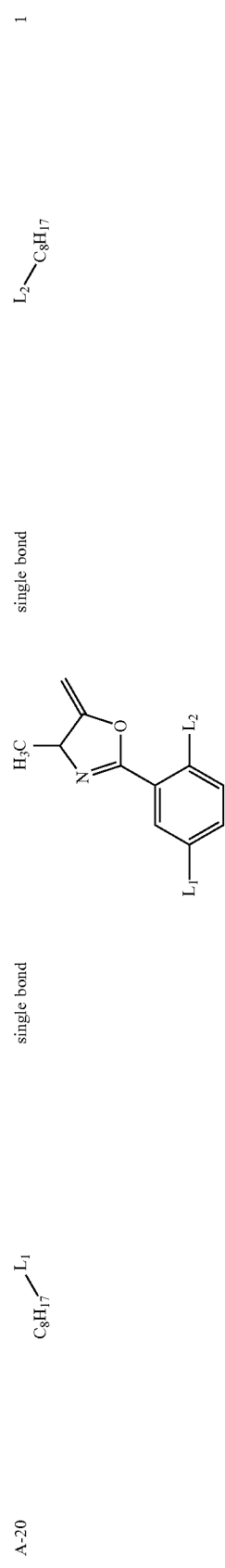 | 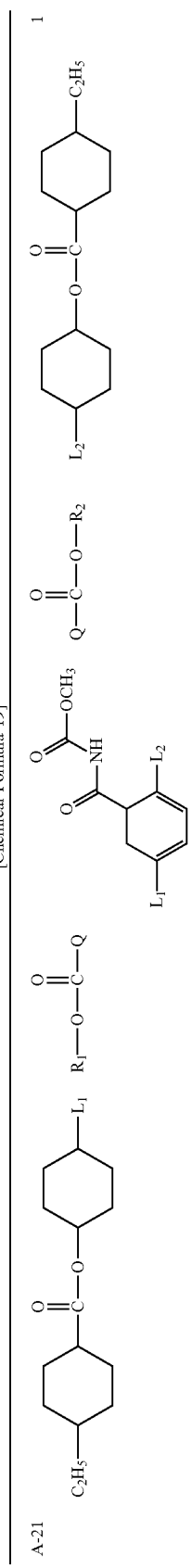 | | | 1 |
| A-20 | $C_8H_{17}$—$L_1$ | single bond | | single bond | $L_2$—$C_8H_{17}$ | 1 |
| A-21 | | | | | | 1 |
[Chemical Formula 19]

-continued

| Compound No. | R₁ | L₁ | $W_a\ W_b$ $\underset{(R_3)_m}{\big|}$ | L₂ | R₂ | n |
|---|---|---|---|---|---|---|
| A-22 | [cyclohexyl(C₂H₅)–C(=O)O–cyclohexyl–L₁] | –R₁–O–C(=O)–Q | Q–C(=O)–CH₂–C(=O)–CH₂–C(=O)–[2,5-(L₁)(L₂)C₆H₃], OC₂H₅ | –Q–O–C(=O)–R₂ | [cyclohexyl–C(=O)O–cyclohexyl(C₂H₅)–L₂] | 1 |
| A-23 | [cyclohexyl(C₂H₅)–C(=O)O–C₆H₄–L₁R₁] | –R₁–O–C(=O)–Q | Q–C(=O)–NH–[2,5-(L₁)(L₂)C₆H₃], OCH₃ | –Q–O–C(=O)–R₂ | [cyclohexyl–C(=O)O–C₆H₄–C(=O)O–cyclohexyl(C₂H₅)–L₂] | 1 |
| A-24 | [cyclohexyl(C₂H₅)–C(=O)O–C₆H₄–L₁R₁] | –R₁–O–C(=O)–Q | Q–C(=O)–CH₂–[2,5-(L₁)(L₂)C₆H₃], SCH₃ | –Q–O–C(=O)–R₂ | [cyclohexyl–C(=O)O–C₆H₄–C(=O)O–cyclohexyl(C₂H₅)–L₂] | 1 |
| A-25 | [cyclohexyl(C₅H₁₁)–C(=O)O–cyclohexyl–L₁] | –R₁–O–C(=O)–Q | 2-phenyl-4,7-(L₁)(L₂)-indole | –Q–O–C(=O)–R₂ | [cyclohexyl(OC₈H₁₇)–L₂] | 1 |

-continued

[Chemical Formula 20]

| Compound No. | $R_1$ | $L_1$ | | $L_2$ | $R_2$ | n |
|---|---|---|---|---|---|---|
| A-26 | (cyclohexyl-cyclohexyl)-C₂H₅ | R₁–C(=O)–O–Q | benzothiazole with CN-phenyl, $L_1$, $L_2$ | Q–O–C(=O)–R₂ | (cyclohexyl-cyclohexyl)-C₂H₅ | 1 |
| A-27 | cyclohexyl–O–C(=O)–phenyl–C(=O)–O–cyclohexyl–C₄H₉ | R₁L₁–C(=O)–O–Q | benzothiazole with (CH₃)₂N-phenyl, $L_1$, $L_2$ | Q–O–C(=O)–R₂ | cyclohexyl–O–C(=O)–phenyl–C(=O)–O–cyclohexyl–C₄H₉ | 1 |

| Compound No. | R₁ | L₁ | $\overset{W_a\ W_b}{\underset{(R_3)_m}{\mid}}$ | L₂ | R₂ | n |
|---|---|---|---|---|---|---|
| A-28 | C₂H₅-(cyclohexyl)-(cyclohexyl)-L₁ | R₁-C(=O)-O-Q | 4-(SO₂CH₃)-phenyl-benzothiazole (L₁, L₂) | Q-O-C(=O)-R₂ | L₂-(cyclohexyl)-(cyclohexyl)-C₂H₅ | 1 |
| A-29 | C₂H₅-(cyclohexyl)-(cyclohexyl)-L₁ | R₁-O-Q | 4-(CH₃)-phenyl-benzoxazole (L₁, L₂) | Q-O-R₂ | L₂-(cyclohexyl)-(cyclohexyl)-C₂H₅ | 1 |

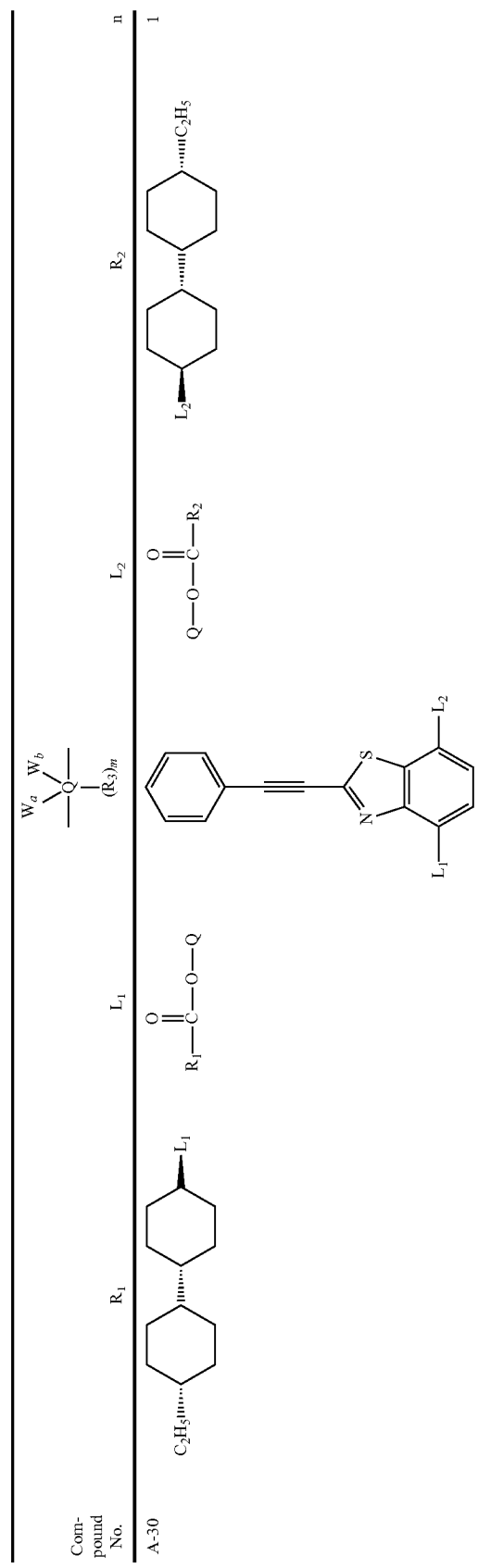
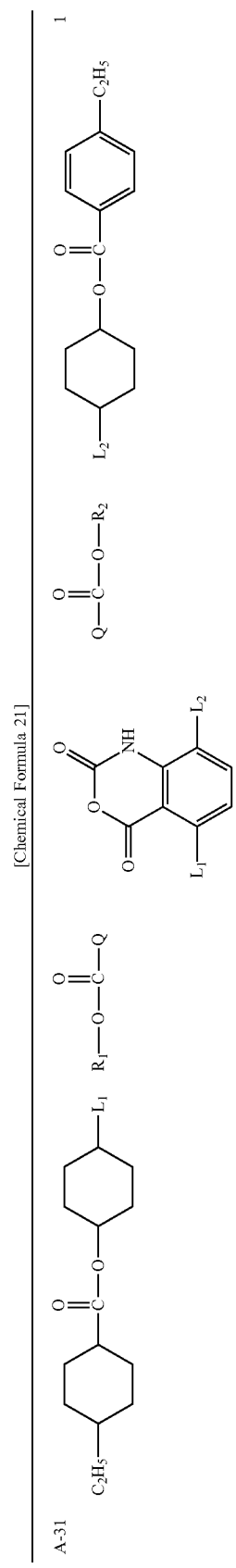
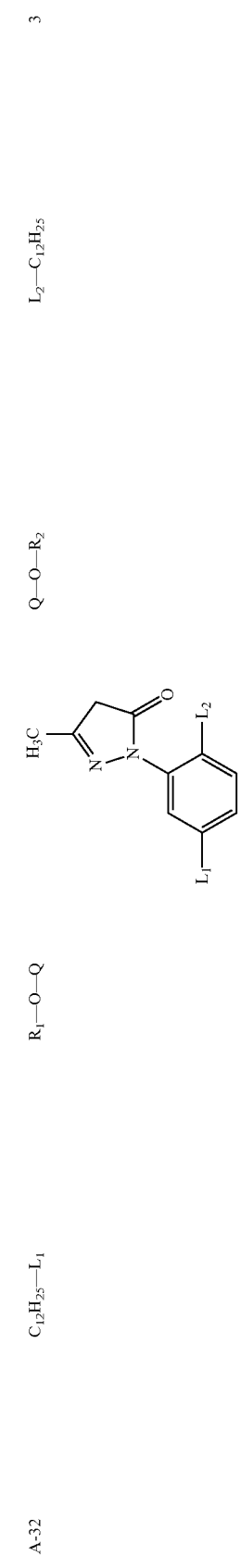

-continued

| Compound No. | R₁ | L₁ | $\overset{W_a\ W_b}{\underset{(R_3)_m}{\big|}}$ | L₂ | R₂ | n |
|---|---|---|---|---|---|---|
| A-33 | cyclohexyl-C(=O)-O- attached to cyclohexyl with C₂H₅ | $R_1-O-\overset{O}{\underset{\|}{C}}-Q$ | pyrazolone with H₃C, N-N, phenyl(2,5-L)  | $Q-\overset{O}{\underset{\|}{C}}-O-R_2$ | cyclohexyl-O-C(=O)-phenyl-C₂H₅ | 1 |
| A-34 | bicyclohexyl with C₂H₅ | $R_1-\overset{O}{\underset{\|}{C}}-O-Q$ | pyrazolone with H₃C, N-N, phenyl(2,5-L)  | $Q-O-\overset{O}{\underset{\|}{C}}-R_2$ | bicyclohexyl with C₂H₅ | 1 |
| A-35 | C₅H₁₁-O-CH₂CH₂-O-CH₂CH₂- | $R_1-\overset{O}{\underset{\|}{C}}-O-Q$ | isatin (indoline-2,3-dione) with L₂/L₁ | $Q-O-\overset{O}{\underset{\|}{C}}-R_2$ | -O-CH₂CH₂-O-CH₂CH₂-O-C₅H₁₁ | 1 |
| A-36 | cyclohexyl-C(=O)-O-cyclohexyl with C₅H₁₁ | $R_1-O-\overset{O}{\underset{\|}{C}}-Q$ | isatin (indoline-2,3-dione) with L₂/L₁ | $Q-\overset{O}{\underset{\|}{C}}-O-R_2$ | cyclohexyl-O-C(=O)-cyclohexyl-C₆H₁₁ | 1 |

[Chemical Formula 22]

-continued

| Compound No. | R₁ | L₁ | Wₐ Wᵦ (R₃)ₘ | L₂ | R₂ | n |
|---|---|---|---|---|---|---|
| A-37 | C₂H₅–C₆H₁₀–C(O)O–C₆H₁₀–L₁ | R₁–O–C(O)–Q | isatin (2,3-dioxoindoline) with L₁, L₂ | Q–C(O)–O–R₂ | L₂–C₆H₁₀–O–C(O)–C₆H₄–C₂H₅ | 1 |
| A-38 | C₅H₁₁–C₆H₁₀–L₁ | R₁–O–C(O)–Q | 2,5-disubstituted phenyl with C(O)CH₂C(O)CF₃ | Q–C(O)–O–R₂ | L₂–C₆H₁₀–C₅H₁₁ | 1 |
| A-39 | C₆H₁₃O–C₆H₄–C(O)O–C₆H₁₀–L₁ | R₁–O–C(O)–Q | 2,5-disubstituted phenyl with C(O)CH₂C(O)CF₃ | Q–C(O)–O–R₂ | L₂–C₆H₁₀–O–C(O)–C₆H₄–OC₆H₁₃ | 1 |
| A-40 | C₁₂H₂₅–L₁ | R₁–O–Q | pyrazoline with CF₃ and 2,5-disubstituted phenyl | Q–O–R₂ | L₂–C₁₂H₂₅ | 1 |

| Compound No. | $R_1$ | $L_1$ | $W_a \overset{\displaystyle W_b}{\underset{\displaystyle (R_3)_m}{-O-}}$ [Chemical Formula 23] | $L_2$ | $R_2$ | n |
|---|---|---|---|---|---|---|
| A-41 | cyclohexyl-cyclohexyl-C$_2$H$_5$ with $L_1$ | $R_1-\overset{O}{\underset{\|}{C}}-O-Q$ | benzothiazole-phenyl($L_1$, $L_2$) | $Q-O-\overset{O}{\underset{\|}{C}}-R_2$ | cyclohexyl-cyclohexyl-C$_2$H$_5$ with $L_2$ | 1 |
| A-42 | C$_5$H$_{11}$-cyclohexyl with $L_1$ | $R_1-\overset{O}{\underset{\|}{C}}-O-Q$ | benzothiazole-phenyl($L_1$, $L_2$) | $Q-O-\overset{O}{\underset{\|}{C}}-R_2$ | cyclohexyl-C$_5$H$_{11}$ with $L_2$ | 1 |
| A-43 | C$_4$H$_9$-cyclohexyl with $L_1$ | $R_1-\overset{O}{\underset{\|}{C}}-O-Q$ | benzothiazole-phenyl($L_1$, $L_2$, H$_3$CS) | $Q-O-\overset{O}{\underset{\|}{C}}-R_2$ | cyclohexyl-C$_4$H$_9$ with $L_2$ | 1 |

| Compound No. | $R_1$ | $L_1$ | $W_a$ $W_b$ $\underset{(R_3)_m}{\bigcirc}$ | $L_2$ | $R_2$ | n |
|---|---|---|---|---|---|---|
| A-44 | cyclohexyl-C(=O)-O-cyclohexyl-C5H11 | $R_1-\overset{O}{\underset{\|}{C}}-O-Q$ | N-methylbenzimidazole with L1, L2 substituents | $Q-O-\overset{O}{\underset{\|}{C}}-R_2$ | cyclohexyl-C(=O)-O-cyclohexyl-C5H11 | 1 |
| A-45 | C2H5O2C-cyclohexyl-L1 | $R_1-\overset{O}{\underset{\|}{C}}-O-Q$ | benzoxazole with L1, L2 substituents | $Q-O-\overset{O}{\underset{\|}{C}}-R_2$ | cyclohexyl-CO2C2H5 | 1 |
| A-46 | C2H5-cyclohexyl-cyclohexyl-L1 | $R_1-\overset{O}{\underset{\|}{C}}-O-Q$ | benzothiazole with L1, L2 substituents (Chemical Formula 24) | $Q-O-\overset{O}{\underset{\|}{C}}-R_2$ | cyclohexyl-cyclohexyl-C2H5 | 1 |

-continued

| Compound No. | R₁ | L₁ | Wₐ—O—Wᵦ / (R₃)ₘ | L₂ | R₂ | n |
|---|---|---|---|---|---|---|
| A-47 | cyclohexyl-C(=O)O-cyclohexyl-L₁, with C₄H₉ substituent | –C(=O)–O–Q | thiophene-phenyl(L₁,L₂) | –Q–O–C(=O)– | cyclohexyl-C(=O)O-cyclohexyl-L₂, with C₄H₉ substituent | 1 |
| A-48 | C₈H₁₇-cyclohexyl-L₁ | –C(=O)–O–Q | benzothiophene-phenyl(L₁,L₂) | –Q–O–C(=O)– | C₈H₁₇-cyclohexyl-L₂ | 1 |
| A-49 | C₄H₉-cyclohexyl-L₁ | –C(=O)–O–Q | CN-phenyl-phenyl(L₁,L₂)-CO₂CH₃ | –Q–O–C(=O)– | C₄H₉-cyclohexyl-L₂ | 1 |
| A-50 | C₄H₉O₂C-cyclohexyl-L₁ | –C(=O)–O–Q | pyridine-phenyl(L₁,L₂) | –Q–O–C(=O)– | CO₂C₄H₉-cyclohexyl-L₂ | 1 |

-continued

| Compound No. | R₁ | L₁ | $\underset{W_a \ W_b}{\overset{|}{\underset{|}{-}}}$ (R₃)ₘ | L₂ | R₂ | n |
|---|---|---|---|---|---|---|
| A-51 | cyclohexyl-C(=O)-cyclohexyl-C₅H₁₁ | R₁-L₁-C(=O)-O-Q | [Chemical Formula 25] benzoxazinone with L₂, L₁ substituents | Q-O-C(=O)-R₂ | L₂-cyclohexyl-cyclohexyl-C₅H₁₁ | 1 |
| A-52 | cyclohexyl-C(=O)-cyclohexyl-C₂H₅ | R₁-L₁-C(=O)-O-Q | benzoxazine with L₂, L₁ | Q-O-C(=O)-R₂ | L₂-cyclohexyl-cyclohexyl-C₂H₅ | 1 |
| A-53 | C₁₀H₂₁-L₁ | R₁-O-Q | perimidine NH with L₂, L₁ | Q-O-R₂ | L₂-C₁₀H₂₁ | 1 |

-continued

| Compound No. | $R_1$ | $L_1$ | $W_a \quad W_b$ $\underset{(R_3)_m}{\longrightarrow}$ | $L_2$ | $R_2$ | n |
|---|---|---|---|---|---|---|
| A-54 | cyclohexyl-$C_4H_9$ | $R_1-\overset{O}{\underset{\|}{C}}-O-Q$ | naphtho-thiazine-phenyl with $L_1$, $L_2$, $N(C_2H_5)_2$ | $Q-O-\overset{O}{\underset{\|}{C}}-R_2$ | cyclohexyl-$C_4H_9$ | 1 |
| A-55 | $C_2H_5O_2C$-cyclohexyl | $R_1-\overset{O}{\underset{\|}{C}}-O-Q$ | benzothiazinone-phenyl with $L_1$, $L_2$ | $Q-O-\overset{O}{\underset{\|}{C}}-R_2$ | cyclohexyl-$CO_2C_2H_5$ | 1 |

[Chemical Formula 26]

| Compound No. | $R_1$ | $L_1$ | | $L_2$ | $R_2$ | n |
|---|---|---|---|---|---|---|
| A-56 | bicyclohexyl-$C_2H_5$ | $R_1-\overset{O}{\underset{\|}{C}}-O-Q$ | furan-phenyl with $L_1$, $L_2$ | $Q-O-\overset{O}{\underset{\|}{C}}-R_2$ | bicyclohexyl-$C_2H_5$ | 1 |

-continued
| Compound No. | R₁ | L₁ | $\begin{array}{c} W_a \; W_b \\ -\!\!-\!\!O\!\!-\!\!(R_3)_m \end{array}$ | L₂ | R₂ | n |
|---|---|---|---|---|---|---|
| A-57 | 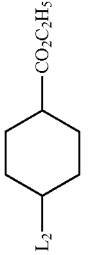 | 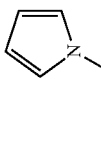 | 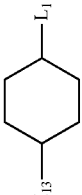 | 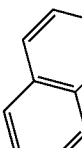 | 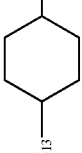 | 1 |
| A-58 | 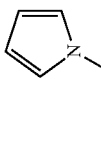 | 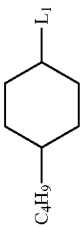 | 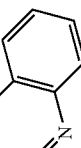 | 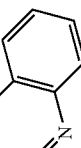 | 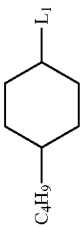 | 3 |
| A-59 | 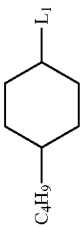 | 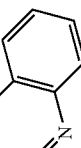 | 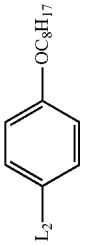 | 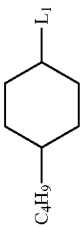 | 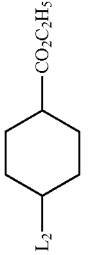 | 1 |
| A-60 | 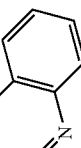 | 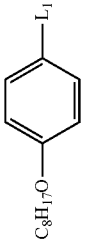 | 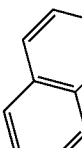 | 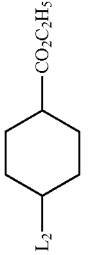 | 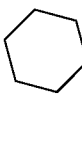 | 1 |

[Chemical Formula 27]

| Compound No. | $R_1$ | $L_1$ | $W_a\ W_b$ $\underset{(R_3)_m}{\overset{|}{\text{—O—}}}$ | $L_2$ | $R_2$ | n |
|---|---|---|---|---|---|---|
| A-61 | (cyclohexyl-$C_4H_9$)-$L_1$ | $R_1-\overset{O}{\underset{\|}{C}}-O-Q$ | benzotriazolyl-phenyl with $L_1$, $L_2$ | $Q-O-\overset{O}{\underset{\|}{C}}-R_2$ | (cyclohexyl-$C_4H_9$)-$L_1$ | 1 |
| A-62 | (bicyclohexyl-$C_2H_5$)-$L_1$ | $R_1-\overset{O}{\underset{\|}{C}}-O-Q$ | maleimide-phenyl with $L_1$, $L_2$ | $Q-O-\overset{O}{\underset{\|}{C}}-R_2$ | (bicyclohexyl-$C_2H_5$)-$L_2$ | 1 |
| A-63 | (phenyl-C(=O)-cyclohexyl)-$L_1$ | $R_1-\overset{O}{\underset{\|}{C}}-O-Q$ | succinimide-phenyl with $L_1$, $L_2$ | $Q-O-\overset{O}{\underset{\|}{C}}-R_2$ | (cyclohexyl-C(=O)-O-phenyl)-$L_2$ | 1 |
| A-64 | (cyclohexyl-O-C(=O)-phenyl-$OC_6H_{13}$)-$L_1$ | $R_1-\overset{O}{\underset{\|}{C}}-O-Q$ | phthalimide-phenyl with $L_1$, $L_2$ | $Q-O-\overset{O}{\underset{\|}{C}}-R_2$ | (cyclohexyl-O-C(=O)-phenyl-$OC_6H_{13}$)-$L_2$ | 1 |

-continued

| Compound No. | R₁ | L₁ | $\begin{array}{c}W_a\ W_b\\|\\-O-\\|\\(R_3)_m\end{array}$ | L₂ | R₂ | n |
|---|---|---|---|---|---|---|
| A-65 | cyclohexyl-cyclohexyl with C₂H₅ (L₁) | $R_1-\overset{O}{\underset{\|}{C}}-O-Q$ | furandione with L₁, L₂ on phenyl | $Q-O-\overset{O}{\underset{\|}{C}}-R_2$ | cyclohexyl-cyclohexyl with C₂H₅ (L₂) | 1 |
| A-66 | C₄H₉-O-CH₂CH₂- (L₁) | $R_1-\overset{O}{\underset{\|}{C}}-O-Q$ | pyridinone with L₁, L₂ on phenyl | $Q-O-\overset{O}{\underset{\|}{C}}-R_2$ | -CH₂CH₂-O-C₄H₉ (L₂) | 1 |
| A-67 | C₈H₁₇-L₁ | R₁—O—Q | glutarimide with L₁, L₂ on phenyl | Q—O—R₂ | L₂-C₈H₁₇ | 2 |
| A-68 | cyclohexyl-cyclohexyl with C₂H₅ (L₁) | $R_1-\overset{O}{\underset{\|}{C}}-O-Q$ | pyridinone with L₁, L₂ on phenyl | $Q-O-\overset{O}{\underset{\|}{C}}-R_2$ | cyclohexyl-cyclohexyl with C₂H₅ (L₂) | 1 |

[Chemical Formula 28]

-continued
| Compound No. | $R_1$ | $L_1$ | $W_a$ $W_b$ $\!\!\!\!-\!\!\!\!\overset{|}{\underset{|}{\text{O}}}\!\!\!\!-\!\!\!\!(R_3)_m$ | $L_2$ | $R_2$ | n |
|---|---|---|---|---|---|---|
| A-69 | $C_6H_{13}\!-\!L_1$ | $R_1\!-\!O\!-\!Q$ | 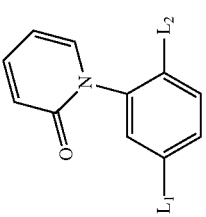 | $Q\!-\!O\!-\!R_2$ | $L_2\!-\!C_6H_{13}$ | 1 |
| A-70 | $C_6H_{13}\!-\!L_1$ | $R_1\!-\!O\!-\!Q$ | 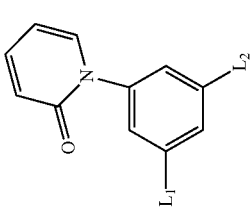 | $Q\!-\!O\!-\!R_2$ | $L_2\!-\!C_6H_{13}$ | 1 |
[Chemical Formula 29]
| A-71 | 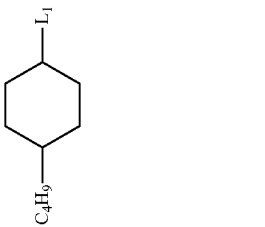 | 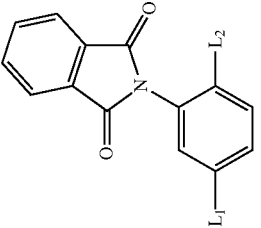 | 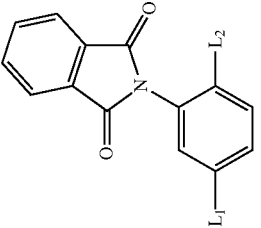 | | | 1 |

-continued

| Compound No. | $R_1$ | $L_1$ | $W_a$ $W_b$ / $(R_3)_m$ | $L_2$ | $R_2$ | n |
|---|---|---|---|---|---|---|
| A-72 | $C_8H_{17}-L_1$ | $R_1-O-Q$ | phthalimide-N-phenyl(L_1,L_2) | $Q-O-R_2$ | $L_2-C_8H_{17}$ | 1 |
| A-73 | $C_5H_{11}-L_1$ | $R_1-O-Q$ | maleimide-N-phenyl(L_1,L_2) | $Q-O-R_2$ | $L_2-C_5H_{11}$ | 1 |
| A-74 | bicyclohexyl with $C_2H_5$ and $L_1$ | $R_1-C(=O)-O-Q$ | morpholine-C(=O)-phenyl(L_1,L_2) | $Q-O-C(=O)-R_2$ | bicyclohexyl with $L_2$ and $C_2H_5$ | 1 |
| A-75 | bicyclohexyl with $C_2H_5$ and $L_1$ | $R_1-C(=O)-O-Q$ | maleimide-N-phenyl(L_1,L_2) with CN, CN | $Q-O-C(=O)-R_2$ | bicyclohexyl with $L_2$ and $C_2H_5$ | 1 |

-continued

[Chemical Formula 30]

| Compound No. | $R_1$ | $L_1$ | $\begin{array}{cc} W_a & W_b \\ & | \\ & O \\ & | \\ & (R_3)_m \end{array}$ | $L_2$ | $R_2$ | n |
|---|---|---|---|---|---|---|
| A-76 | C5H11O—⟨phenyl⟩—CO-O—⟨cyclohexyl⟩—L1 | R1—C(=O)—O—Q | phenothiazine with N-(2,5-L1,L2-phenyl) | Q—O—C(=O)—R2 | L2—⟨cyclohexyl⟩—O-CO—⟨phenyl⟩—OC5H11 | 2 |
| A-77 | C2H5O2C—⟨cyclohexyl⟩—L1 | R1—C(=O)—O—Q | carbazole with N-(2,5-L1,L2-phenyl) | Q—O—C(=O)—R2 | L2—⟨cyclohexyl⟩—CO2C2H5 | 1 |
| A-78 | C10H21—L1 | R1—O—Q | carbazole with N-(2,5-L1,L2-phenyl) | Q—O—R2 | L2—C10—H21 | 1 |

-continued

| Compound No. | R₁ | L₁ | Wₐ Wᵦ / (R₃)ₘ | L₂ | R₂ | n |
|---|---|---|---|---|---|---|
| A-79 | cyclohexyl with L₁, C₂H₅O₂C— substituent | —C(=O)—O—Q— | carbazole-phenyl with L₁, L₂, and H₃C—C(=O)— group | —Q—O—C(=O)—R₂ | cyclohexyl with L₂, —CO₂C₂H₅ | 1 |
| A-80 | bicyclohexyl with L₁, C₂H₅— substituent | —C(=O)—O—Q— | pyridazinone-phenyl with L₁, L₂, F substituents | —Q—O—C(=O)—R₂ | bicyclohexyl with L₂, C₂H₅— substituent | 1 |

In regard to the specific examples of the compound, in a case in which geometric isomers (trans-form and cis-form) exist, unless defined specifically, any isomer may be used without any limitation; however, trans-form having superior retardation development properties is preferred to cis-form.

The compound represented by General Formula (A) can be synthesized by a known method. Specifically, the compound can be synthesized by making reference to Japanese Patent Application Laid-Open No. 2008-107767, or the like.

Synthesis Example for Exemplary Compound A-41 extraction is carried out. The solvent is distilled off under reduced pressure from the organic layer thus obtained, and thus 3.5 g of compound (i) is obtained. The yield is 75%.

45 mL of tetrahydrofuran is added to 7.0 g of compound (m), and the mixture is cooled in an ice water bath. A tetrahydrofuran (5 mL) solution of 3.5 g of compound (i) and a tetrahydrofuran (1 mL) solution of 2 mg of dimethylaminopyridine are sequentially added dropwise to the mixture, and the mixture is stirred for 3 hours at room temperature. Subsequently, water and ethyl acetate are

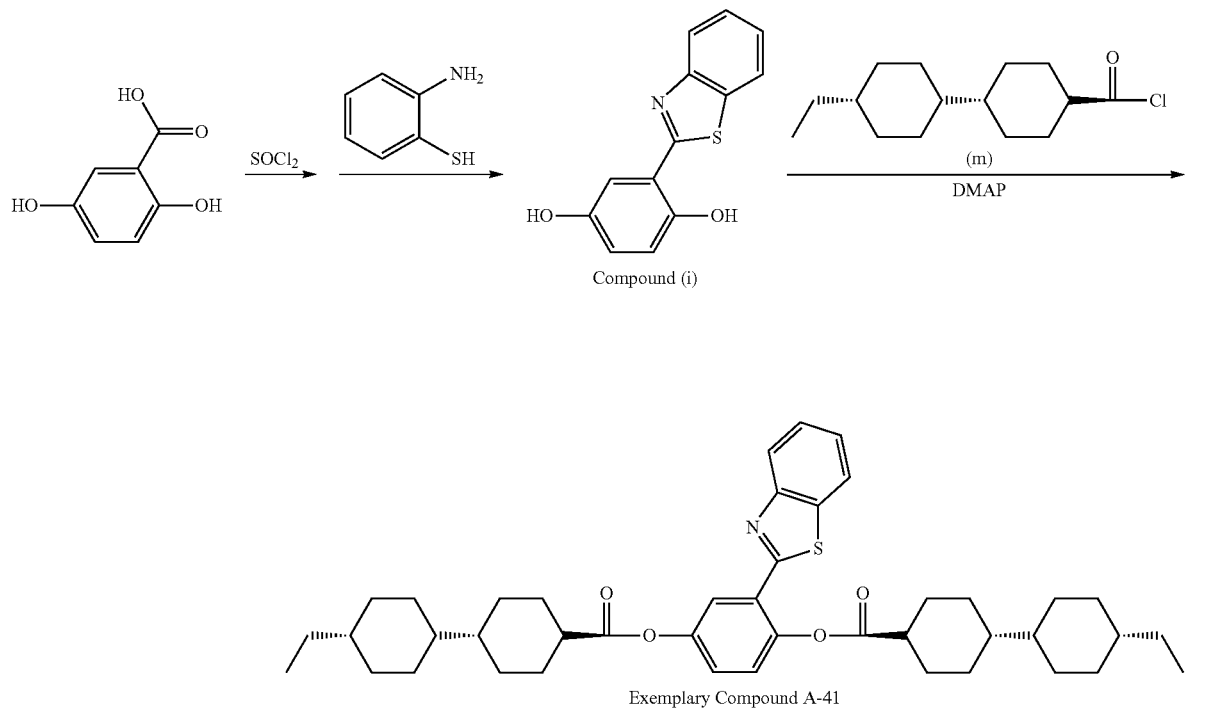

[Chemical Formula 31]

Exemplary Compound A-41

3 g of 2,5-dihydroxybenzoic acid is dissolved in 30 mL of toluene, 4.2 mL of thionyl chloride is added dropwise thereto, and the mixture is stirred for 2 hours. Toluene and thionyl chloride are distilled off under reduced pressure, subsequently 20 mL of toluene is added to the residue, and 2.4 g of o-aminothiophenol in toluene (5 mL) is added dropwise thereto. The mixture is stirred for 12 hours at room temperature, water and ethyl acetate are added thereto, and added thereto, and extraction is carried out. The solvent is distilled off under reduced pressure from the organic layer, crude crystals thus obtained are purified by silica gel chromatography (ethyl acetate/heptane), and thus Exemplary Compound (A-41) is obtained. The yield amount is 5.5 g, and the yield is 70%.

Synthesis Example for Exemplary Compound A-66

[Chemical Formula 32]

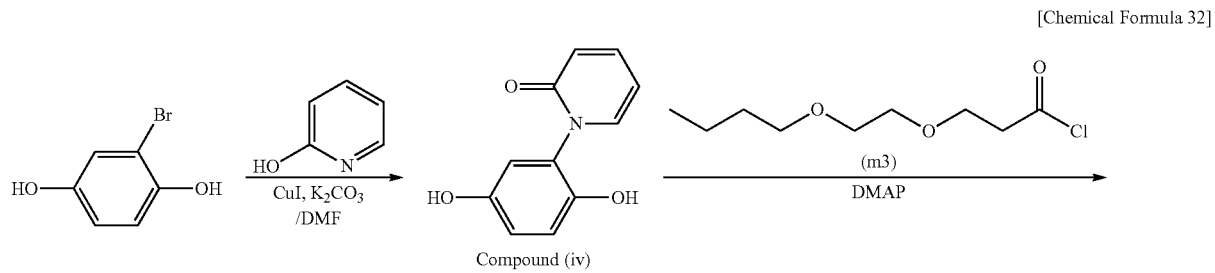

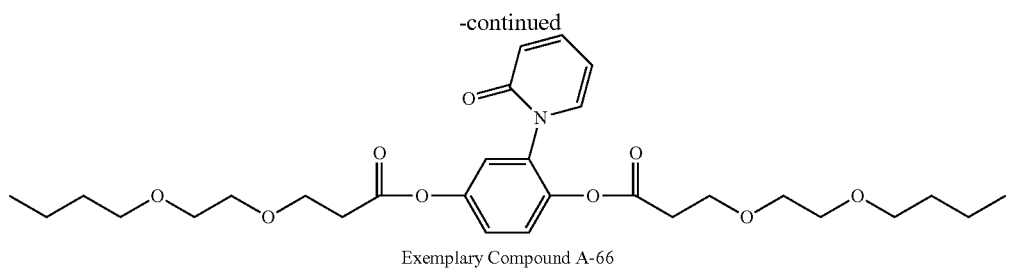

Exemplary Compound A-66

3.4 g of 2,5-dihydroxybromobenzene, 1.8 g of 2-hydroxypyridine, 1.7 g of copper iodide, and 3.8 g of potassium carbonate are dissolved in 30 mL of dimethylformamide (DMF), and the solution is heated for 6 hours at 150° C. The solution thus obtained is left to cool, water and toluene are added thereto, and extraction is carried out. The solvent is distilled off under reduced pressure from the organic layer thus obtained, and thus 2.3 g of compound (iv) is obtained. The yield is 63%.

50 mL of tetrahydrofuran is added to 4.3 g of compound (m3), the mixture is cooled in an ice water bath. A tetrahydrofuran solution of 2.3 g of compound (iv) and a tetrahydrofuran (1 mL) solution of 2 mg of dimethylaminopyridine are sequentially added dropwise to this mixture, and then the mixture is stirred for 3 hours at room temperature. Water and ethyl acetate are added to the solution thus obtained, and extraction is carried out. The solvent is distilled off under reduced pressure from the organic layer, crude crystals thus obtained are purified by silica gel chromatography (ethyl acetate/heptane), and thus Exemplary Compound (A-66) is obtained. The yield amount is 5.0 g, and the yield is 80%.

The content of the compound used in the present invention is appropriately set to the extent that the required wavelength dispersion regulation ability and retardation development properties can be given. Specifically, the content of the compound used in the present invention is preferably 1% to 15% by mass, and more preferably 2% to 10% by mass, with respect to the thermoplastic resin. If the content of the relevant compound is less than 1% by mass, it is difficult to obtain the desired retardation development properties or wavelength dispersion regulating function, and if the content is more than 15% by mass, the optical film is prone to cause bleed-out. If the content of the relevant compound is in the range described above, sufficient wavelength dispersibility and high retardation development properties may be given to the optical film of the present invention.

The optical film of the present invention may further contain various additives, as necessary.

(Sugar Ester Compound)

A sugar ester compound is a compound having one to twelve furanose structures or pyranose structures, and a compound in which all or some of the hydroxyl groups in the compound have been esterified.

Preferred examples of such a sugar ester compound include a sucrose ester compound represented by the following General Formula (3):

[Chemical Formula 33]

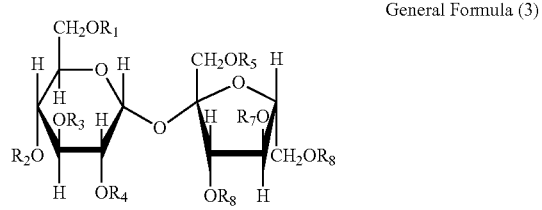

General Formula (3)

$R_1$ to $R_8$ in Formula (3) each represent a substituted or unsubstituted alkylcarbonyl group, or a substituted or unsubstituted arylcarbonyl group. $R_1$ to $R_8$ may be identical with or different from each other.

The substituted or unsubstituted alkylcarbonyl group is preferably a substituted or unsubstituted alkylcarbonyl group having 2 or more carbon atoms. Examples of the substituted or unsubstituted alkylcarbonyl group include a methylcarbonyl group (acetyl group). Examples of the substituent on the alkyl group include an aryl group such as a phenyl group.

The substituted or unsubstituted arylcarbonyl group is preferably a substituted or unsubstituted arylcarbonyl group having 7 or more carbon atoms. Examples of the arylcarbonyl group include a phenylcarbonyl group. Examples of the substituent on the aryl group include an alkyl group such as a methyl group, and an alkoxy group such as a methoxy group.

The average degree of ester substitution of the sucrose ester compound is preferably 3.0 to 7.5. If the average degree of ester substitution is less than 3.0 or more than 7.5, it is difficult to obtain sufficient compatibility with cellulose esters.

Specific examples of the sucrose ester compound represented by General Formula (3) include the following compounds. R in the table represents $R_1$ to $R_8$ in General Formula (3).

[Chemical Formula 34]

| Compound No. | R | Average degree of substitution |
|---|---|---|
| FA-1 | O‖—C—CH$_3$ | 3.3 |
| FA-2 | O‖—C—CH$_3$ | 4.2 |

[Chemical Formula 34]

| Compound No. | R | Average degree of substitution |
|---|---|---|
| FA-3 | —C(=O)—CH$_3$ | 5.7 |
| FA-4 | —C(=O)—CH$_3$ | 6.0 |
| FA-5 | —C(=O)—C$_6$H$_5$ | 3.5 |
| FA-6 | —C(=O)—C$_6$H$_5$ | 4.0 |
| FA-7 | —C(=O)—C$_6$H$_5$ | 5.5 |
| FA-8 | —C(=O)—C$_6$H$_5$ | 6.0 |
| FA-9 | —C(=O)—C$_6$H$_4$—CH$_3$ | 3.2 |
| FA-10 | —C(=O)—C$_6$H$_4$—CH$_3$ | 4.4 |
| FA-11 | —C(=O)—C$_6$H$_4$—CH$_3$ | 5.5 |
| FA-12 | —C(=O)—C$_6$H$_4$—CH$_3$ | 6.0 |
| FA-13 | —C(=O)—CH$_2$—C$_6$H$_5$ | 3.0 |
| FA-14 | —C(=O)—CH$_2$—C$_6$H$_5$ | 4.0 |
| FA-15 | —C(=O)—CH$_2$—C$_6$H$_5$ | 5.5 |
| FA-16 | —C(=O)—CH$_2$—C$_6$H$_5$ | 6.0 |
| FA-17 | —C(=O)—C$_6$H$_2$(OCH$_3$)$_3$ | 3.1 |
| FA-18 | —C(=O)—C$_6$H$_2$(OCH$_3$)$_3$ | 4.7 |
| FA-19 | —C(=O)—C$_6$H$_2$(OCH$_3$)$_3$ | 5.3 |
| FA-20 | —C(=O)—C$_6$H$_2$(OCH$_3$)$_3$ | 6.0 |
| FA-21 | —C(=O)—CH(CH$_3$)$_2$ | 3.5 |
| FA-22 | —C(=O)—CH(CH$_3$)$_2$ | 4.6 |
| FA-23 | —C(=O)—CH(CH$_3$)$_2$ | 5.6 |
| FA-24 | —C(=O)—CH(CH$_3$)$_2$ | 6.0 |

In addition, examples of the sugar ester compound include the compounds described in Japanese Patent Application Laid-Open Nos. 62-42996 and Japanese Patent Application Laid-Open No. 10-237084.

The content of the sugar ester compound is preferably 0.5% to 35% by mass, and more preferably 5% to 30% by mass, with respect to the thermoplastic resin.

The optical film of the present invention may contain a plasticizer in order to increase fluidity of the composition at the film production, or flexibility of the film. Examples of the plasticizer include polyester-based plasticizers, polyhydric alcohol ester-based plasticizers, polyvalent carboxylic acid ester-based plasticizers (including phthalic acid ester-based plasticizers), glycolate-based plasticizers, and ester-based plasticizers (including citric acid ester-based plasticizers, fatty acid ester-based plasticizers, phosphoric acid ester-based plasticizers, trimellitic acid ester-based plasticizers, and the like). These plasticizers may be used singly or in combination.

A polyester-based plasticizer is a compound obtained by allowing a monovalent to tetravalent carboxylic acid to react with a monohydric to hexahydric alcohol, and is preferably a compound obtained by allowing a divalent carboxylic acid to react with glycol.

Examples of the divalent carboxylic acid include glutaric acid, itaconic acid, adipic acid, phthalic acid, azelaic acid, and sebacic acid. Particularly, a compound obtained using adipic acid, phthalic acid or the like as the divalent carboxylic acid may provide favorable plasticity.

Examples of the glycol include ethylene glycol, propylene glycol, 1,3-butylene glycol, 1,4-butylene glycol, 1,6-hexamethylene glycol, neopentylene glycol, diethylene glycol, triethylene glycol, and dipropylene glycol. The divalent carboxylic acids and glycols may be used singly or in combination.

The polyester-based plasticizer may be any of an ester, an oligoester, or a polyester. The molecular weight of the polyester-based plasticizer is preferably in the range of 100 to 10,000, and from the viewpoint of having a superior effect of providing plasticity, the molecular weight is more preferably in the range of 600 to 3,000.

The viscosity of the polyester-based plasticizer may depend on the molecular structure or the molecular weight, and in the case of an adipic acid-based plasticizer, from the viewpoint of having high compatibility with thermoplastic resins and having a superior effect of providing plasticity, the viscosity is preferably in the range of 200 MPa·s to 5,000 MPa·s (25° C.). The polyester-based plasticizers may be used singly or in combination.

A polyhydric alcohol ester-based plasticizer is an ester compound between a divalent or higher-valent aliphatic polyhydric alcohol and a monocarboxylic acid (alcohol ester), and is preferably a divalent to eicosavalent aliphatic polyhydric alcohol ester. It is preferable that the polyhydric alcohol ester-based compound have an aromatic ring or a cycloalkyl ring in the molecule.

Examples of the aliphatic polyhydric alcohol include ethylene glycol, propylene glycol, trimethylolpropane, and pentaerythritol.

The monocarboxylic acid may be an aliphatic monocarboxylic acid, an alicyclic monocarboxylic acid, or an aromatic monocarboxylic acid. The monocarboxylic acids may be used singly or as a mixture thereof. Furthermore, all of the OH groups contained in the aliphatic polyhydric alcohol may be esterified, or some of them may be left as OH groups.

The aliphatic monocarboxylic acid is preferably a linear or branched fatty acid having 1 to 32 carbon atoms. The number of carbon atoms of the aliphatic monocarboxylic acid is more preferably 1 to 20, and even more preferably 1 to 10. Examples of such an aliphatic monocarboxylic acid include acetic acid, propionic acid, butyric acid, and valeric acid, and in order to increase compatibility with cellulose esters, the aliphatic monocarboxylic acid is preferably acetic acid.

Examples of the alicyclic monocarboxylic acid include cyclopentanecarboxylic acid, cyclohexanecarboxylic acid, and cyclooctanecarboxylic acid.

Examples of the aromatic monocarboxylic acid include benzoic acid; benzoic acid having one to three alkyl groups or alkoxy groups (for example, methoxy groups or ethoxy groups) introduced to the benzene ring (for example, toluic acid); and an aromatic monocarboxylic acid having two or more benzene rings (for example, biphenylcarboxylic acid, naphthalenecarboxylic acid, or tetralinecarboxylic acid). A preferred example of the aromatic monocarboxylic acid is benzoic acid.

The molecular weight of the polyhydric alcohol ester-based plasticizer is not particularly limited, but the molecular weight is preferably 300 to 1500, and more preferably 350 to 750. In order to make the plasticizer difficult to volatilize, it is preferred that the plasticizer have a larger molecular weight; and in order to increase moisture permeability and compatibility with cellulose esters, a plasticizer having a smaller molecular weight is preferred.

Specific examples of the polyhydric alcohol ester-based plasticizer include trimethylolpropane triacetate, pentaerythritol tetraacetate, and the ester compound (A) represented by formula (I) described in Japanese Patent Application Laid-Open No. 2008-88292.

A polyvalent carboxylic acid ester-based plasticizer is an ester compound between a divalent or higher-valent, preferably divalent to eicosavalent, polyvalent carboxylic acid and an alcohol compound. The polyvalent carboxylic acid is preferably a divalent to eicosavalent aliphatic polyvalent carboxylic acid, a trivalent to eicosavalent aromatic polyvalent carboxylic acid, or trivalent to eicosavalent alicyclic polycarboxylic acid.

Examples of the polyvalent carboxylic acid include trivalent or higher-valent aromatic polyvalent carboxylic acids such as trimellitic acid, trimesic acid and pyromellitic acid, or derivatives thereof; aliphatic polyvalent carboxylic acids such as succinic acid, adipic acid, azelaic acid, sebacic acid, oxalic acid, fumaric acid, maleic acid, and tetrahydrophthalic acid; and polyvalent oxycarboxylic acids such as tartaric acid, tartronic acid, malic acid, and citric acid. In order to suppress volatilization from the film, a polyvalent oxycarboxylic acid is preferred.

Examples of the alcohol compound include a linear or branched saturated aliphatic alcohol compound, a linear or branched unsaturated aliphatic alcohol compound, an alicyclic alcohol compound, or an aromatic alcohol compound. The number of carbon atoms of the saturated aliphatic alcohol compound or unsaturated aliphatic alcohol compound is preferably 1 to 32, more preferably 1 to 20, and even more preferably 1 to 10. Examples of the alicyclic alcohol compound include cyclopentanol and cyclohexanol. Examples of the aromatic alcohol compound include phenol, para-cresol, dimethylphenol, benzyl alcohol, and cinnamyl alcohol. The alcohol compounds may be of a single kind, or a mixture of two or more kinds.

The molecular weight of the polyvalent carboxylic acid ester-based plasticizer is not particularly limited and is preferably 300 to 1,000, and more preferably 350 to 750. The molecular weight of the polyvalent carboxylic acid ester-based plasticizer is preferably larger from the viewpoint of suppressing bleed-out; and from the viewpoint of moisture permeability or compatibility with cellulose esters, the molecular weight is preferably smaller.

The acid value of the polyvalent carboxylic acid ester-based plasticizer is 1 mg KOH/g or less, and more preferably 0.2 mg KOH/g or less. The acid value refers to the number of milligrams of potassium hydroxide required to neutralize the acid contained in 1 g of a sample (carboxyl groups present in the sample). The acid value is measured according to JIS K0070.

Examples of the polyvalent carboxylic acid ester-based plasticizer include ester compound (B) represented by General Formula (II) described in Japanese Patent Application Laid-Open No. 2008-88292.

The polyvalent carboxylic acid ester-based plasticizer may be a phthalic acid ester-based plasticizer. Examples of the phthalic acid ester-based plasticizer include diethyl phthalate, dimethoxyethyl phthalate, dimethyl phthalate, dioctyl phthalate, dibutyl phthalate, di-2-ethylhexyl phthalate, dioctyl phthalate, dicyclohexyl phthalate, and dicyclohexyl terephthalate.

Examples of the glycolate-based plasticizer include alkyl phthalyl alkyl glycolate. Examples of the alkyl phthalyl alkyl glycolate include methyl phthalyl methyl glycolate, ethyl phthalyl ethyl glycolate, propyl phthalyl propyl glycolate, butyl phthalyl butyl glycolate, and octyl phthalyl octyl glycolate.

Examples of the ester-based plasticizer include fatty acid ester-based plasticizers, citric acid ester-based plasticizers, phosphoric acid ester-based plasticizers, and trimellitic acid-based plasticizers.

Examples of the fatty acid ester-based plasticizers include butyl oleate, methyl acetyl ricinolate, and dibutyl sebacate. Examples of the citric acid ester-based plasticizers include acetyl trimethyl citrate, acetyl triethyl citrate, and acetyl tributyl citrate. Examples of the phosphoric acid ester-based plasticizers include triphenyl phosphate, tricresyl phosphate, cresyl diphenyl phosphate, octyl diphenyl phosphate, diphenyl biphenyl phosphate, trioctyl phosphate, and tributyl phosphate. Examples of the trimellitic acid-based plasticizers include octyl trimellitate, n-octyl trimellitate, isodecyl trimellitate, and isononyl trimellitate.

The content of the plasticizer is preferably 0.5% to 30% by mass with respect to the thermoplastic resin. If the content of the plasticizer is more than 30% by mass, the film is prone to cause bleed-out.

The optical film of the present invention may further contain antioxidants, antistatic agents flame retardants and the like for preventing thermal decomposition or coloration caused by heat at the time of molding processing.

A phosphorus-based flame retardant may be one or more selected from red phosphorus, triaryl phosphoric acid esters, diaryl phosphoric acid esters, monoaryl phosphoric acid esters, arylphosphonic acid compounds, arylphosphine oxide compounds, condensed aryl phosphoric acid esters, halogenated alkyl phosphoric acid esters, halogen-containing condensed phosphoric acid esters, halogen-containing condensed phosphonic acid esters, and halogen-containing phosphorous acid esters. Specific examples thereof include triphenyl phosphate, 9,10-dihydro-9-oxa-10-phosphaphenanthrene-10 oxide, phenylphosphonic acid, tris(β-chloroethyl)phosphate, tris(dichloropropyl)phosphate, and tris(tribromoneopentyl)phosphate.

Ultraviolet Absorber

The optical film of the present invention may further contain an ultraviolet absorber. The ultraviolet absorber may for example be a benzotriazole-based compound, a 2-hydroxybenzophenone-based compound, or salicylic acid phenyl ester-based compound. Specific examples include triazoles such as 2-(5-methyl-2-hydroxyphenyl)benzotriazole, 2-[2-hydroxy-3,5-bis(α,α-dimethylbenzyl)phenyl]-2H-benzotriazole, and 2-(3,5-di-t-butyl-2-hydroxyphenyl)benzotriazole; and benzophenones such as 2-hydroxy-4-methoxybenzophenone, 2-hydroxy-4-octoxybenzophenone, and 2,2'-dihydroxy-4-methoxybenzophenone.

Among them, an ultraviolet absorber having a molecular weight of 400 or more has a high boiling point, does not easily volatilize, and does not easily scatter away even at the time of high temperature molding; therefore, weather resistance may be imparted to the resultant film, even if the amount of addition is relatively small.

Examples of the ultraviolet absorber having a molecular weight of 400 or more include benzotriazole-based compounds such as 2-[2-hydroxy-3,5-bis(α,α-dimethylbenzyl)phenyl]-2-benzotriazole, and 2,2-methylenebis[4-(1,1,3,3-tetrabutyl)-6-(2H-benzotriazol-2-yl)phenol];

hindered amine-based compounds such as bis(2,2,6,6-tetramethyl-4-piperidyl)sebacate, bis(1,2,2,6,6-pentamethyl-4-piperidyl)sebacate; and hybrid compounds having both a hindered phenol structure and a hindered amine structure in the molecule, such as bis(1,2,2,6,6-pentamethyl-4-piperidyl) 2-(3,5-di-t-butyl-4-hydroxybenzyl)-2-n-butylmalonate, and 1-[2-[3-(3,5-di-t-butyl-4-hydroxyphenyl)propionyloxy]ethyl]-4-[3-(3,5-di-t-butyl-4-hydroxyphenyl)propionyloxy]-2,2,6,6-tetramethylpiperidine. Preferred examples include 2-[2-hydroxy-3,5-bis(α,α-dimethylbenzyl)phenyl]-2-benzotriazole, and 2,2-methylenebis[4-(1,1,3,3-tetrabutyl)-6-(2H-benzotriazol-2-yl)phenol]. These may be used singly or in combination.

Fine Particles

Fine particles are formed from an inorganic compound or an organic compound. Examples of the inorganic compound include silicon dioxide, titanium dioxide, aluminum oxide, zirconium oxide, calcium carbonate, talc, clay, calcined kaolin, calcined calcium silicate, hydrated calcium silicate, aluminum silicate, magnesium silicate, and calcium phosphate. Examples of the organic compound include polytetrafluoroethylene, cellulose acetate, polystyrene, polymethyl methacrylate, polypropyl methacrylate, polymethyl acrylate, polyethylene carbonate, acrylstryene-based resins, silicone-based resins, polycarbonate resins, benzoguanamine-based resins, melamine-based resins, polyolefin-based powder, polyester-based resins, polyamide-based resins, polyimide-based resins, polyfluoroethylene-based resins, pulverization and classification products of organic polymer compounds such as starch, polymer compounds synthesized by a suspension polymerization method, and polymer compounds shaped into spheres by a spray drying method, a dispersion method or the like.

The fine particles may be composed of a compound containing silicon (preferably, silicon dioxide), from the viewpoint of maintaining the haze of the resulting film at a low level.

Examples of fine particles of silicon dioxide include AEROSIL R972, R972V, R974, R812, 200, 200V, 300, R202, OX50, TT600 (all manufactured by Nippon Aerosil Co., Ltd.).

Examples of fine particles of zirconium oxide include AEROSIL R976 and R811 (all manufactured by Nippon Aerosil Co., Ltd.).

Examples of the resin for polymer fine particles include silicone resins, fluororesins, and (meth)acrylic resins, and preferred examples include silicone resins, with more preferred examples being silicone resins having a three-dimensional network structure. Examples of such silicone resins include TOSPEARL 103, TOSPEARL 105, TOSPEARL 108, TOSPEARL 120, TOSPEARL 145, TOSPEARL 3120, and TOSPEARL 240 (all manufactured by Toshiba Silicone Co., Ltd.).

Among them, AEROSIL 200V and AEROSIL R972V are particularly preferred from the viewpoint that the haze of the optical film can be maintained low, while sliding properties of the film surface can be increased.

The average particle size of primary particles of the fine particles is preferably 5 nm to 400 nm, and more preferably 10 nm to 300 nm. The fine particles may form secondary aggregates mainly having a particle size of 0.05 μm to 0.3 μm. When the average particle size of the fine particles is 100 nm to 400 nm, the fine particles may exist as primary particles without being aggregated.

It is preferable to incorporate fine particles such that the dynamic friction coefficient of at least one surface of the optical film is 0.2 to 1.0. The content of the fine particles is preferably 0.01% to 1% by mass, and more preferably 0.05% to 0.5% by mass, with respect to the thermoplastic resin.

Dispersant

The optical film of the present invention may further contain a dispersant in order to increase dispersibility of the fine particles. The dispersant is one or two or more kinds selected from amine-based dispersants and carboxyl group-containing polymeric dispersants.

Amine-based dispersants are preferably alkylamines, or amine salts of polycarboxylic acids, and specific examples thereof include polyester acids, polyether ester acids, fatty acids, fatty acid amides, polycarboxylic acids, alkylene oxides, polyalkylene oxides, polyoxyethylene fatty acid esters, and compounds obtained by aminating polyoxyethylene glycerin fatty acid esters. Examples of amine salts include amideamine salts, aliphatic amine salts, aromatic amine salts, alkanolamine salts, and polyvalent amine salts.

Specific examples of amine-based dispersants include polyoxyethylene fatty acid amides, polyoxyethylene alkylamines, tripropylamine, diethylaminoethylamine, dimethylaminopropylamine, and diethylaminopropylamine. Examples of commercially available products include SOL-SPERSE series (manufactured by Lubrizol Corp.), AJISPER series (manufactured by Ajinomoto Co., Inc.), BYK series (manufactured by BYK Chemie GmbH), and EFKA series (manufactured by EFKA GmbH & Co., KG).

The carboxyl group-containing polymeric dispersant is preferably a polycarboxylic acid or a salt thereof, and examples include polycarboxylic acids, ammonium polycarboxylate, and sodium polycarboxylate. Specific examples of the carboxyl group-containing polymeric dispersant include polyacrylic acid, ammonium polyacrylate, sodium polyacrylate, an ammonium polyacrylate copolymer, polymaleic acid, ammonium polymaleate, and sodium polymaleate.

The amine-based dispersant or carboxyl group-containing polymeric dispersant may be used by dissolving the dispersant in a solvent component, or a commercially available product may also be used.

The content of the dispersant may vary with the kind of the dispersant or the like, but the content is preferably 0.2% by mass or more with respect to the fine particles. If the content of the dispersant is less than 0.2% by mass with respect to the fine particles, dispersibility of the fine particles cannot be sufficiently increased.

When the optical film of the present invention further contains a surfactant and the like, it may be more difficult for the adsorption of the dispersant to the surface of fine particles to occur compared to the adsorption of the surfactant, and the fine particles may be easily reaggregated. Since dispersants are expensive, it is preferable that the content of the dispersant be as small as possible. On the other hand, if the content of the dispersant is too small, the fine particles are prone to cause poor wetting, or a decrease in dispersion stability. Therefore, the content of the dispersant in the case in which the optical film of the present invention further contains a surfactant and the like, may be adjusted to about 0.05 parts to 10 parts by weight relative to 10 parts by weight of the fine particles.

Properties of Optical Film

The optical film of the present invention is preferably such that the retardation in the in-plane direction, $R_0(550)$, that is measured at the wavelength of 550 nm under condition of 23° C. and 55% RH, satisfy the following requirement (a). An optical film in which $R_0(550)$ satisfies the following range can preferably function as, for example, a λ/4 retardation film.

$$110 \text{ nm} \leq R_0(550) \leq 170 \text{ nm} \tag{a}$$

The optical film of the present invention more preferably satisfies the requirement: $120 \leq R_0(550) \leq 160$, and even more preferably satisfies the requirement: $130 \leq R_0(550) \leq 150$. Furthermore, the optical film of the present invention is preferably such that the retardation in the thickness direction, Rth(550), that is measured at the wavelength of 550 nm under the conditions of 23° C. and 55% RH, satisfy the requirement: 50 nm≤Rth(550)≤250 nm It is preferable that when the retardations in the in-plane direction that are measured at the wavelengths of 450 nm and 650 nm under the conditions of 23° C. and 55% RH are designated as $R_0(450)$ and $R_0(650)$, respectively, the optical film of the present invention further satisfy the following requirements (b) and (c):

$$0.72 \leq R_0(450)/R_0(550) \leq 0.96 \tag{b}$$

$$0.83 \leq R_0(550)/R_0(650) \leq 0.97 \tag{c}$$

An optical film in which $R_0(450)/R_0(550)$ and $R_0(550)/R_0(650)$ satisfy the above-described ranges can give, for example, a retardation of λ/4 to light over a wide wavelength region, and thus can preferably function as a λ/4 retardation film. Furthermore, light leakage when a black image is displayed, changes in color tone when viewed in oblique directions, and the like can also be reduced. Specifically, when the requirement (b) $0.72 \leq R_0(450)/R_0(550) \leq 0.96$ is satisfied, blue color reproducibility is high; and when the requirement (c) $0.83 \leq R_0(550)/R_0(650) \leq 0.97$ is satisfied, red color reproducibility is high.

It is more preferable that the optical film of the present invention satisfy the requirement: $0.79 \leq R_0(450)/R_0(550) \leq 0.89$, and it is more preferable that the optical film satisfy the requirement: $0.84 \leq R_0(550)/R_0(650) \leq 0.93$.

$R_0$ (retardation), $R_0(450)/R_0(550)$, and $R_0(550)/R_0(650)$ (wavelength dispersibility) may be adjusted by the content of the compound used in the present invention, or the stretching conditions. In order to satisfy all of the above requirements (a) to (c), for example, it is preferable to incorporate the compound used in the present invention in a certain amount or more, and to adjust the stretching conditions.

$R_0$ and Rth are respectively defined by the following formulas:

$$R_0 = (nx - ny) \times d \text{ (nm)} \tag{Formula (I)}$$

$$Rth = \{(nx + ny)/2 - nz\} \times d \text{ (nm)} \tag{Formula (II)}$$

wherein in Formulas (I) and (II), nx represents the refractive index in the slow axis direction x, at which the refractive index in the in-plane direction of the optical film becomes maximum;

ny represents the refractive index in a direction y perpendicular to the slow axis direction x with respect to the in-plane direction of the optical film;

nz represents the refractive index in the thickness direction z of the optical film; and d (nm) represents the thickness of the optical film.

$R_0$ and Rth can be measured using an automatic birefringence meter; for example, AXOSCAN manufactured by Axometrics, Inc., KOBRA-21ADH manufactured by Oji Scientific Instruments Co., Ltd., or the like. Specifically, $R_0$ and Rth can be measured by the following method.

1) An optical film is humidified at 23° C. and 55% RH. The average refractive indices of the optical film after humidification at 450 nm, 550 nm and 650 nm are measured using an Abbe refractometer and a spectroscopic light source. Furthermore, the thickness of the optical film is measured using a film thickness meter.

2) The retardation in the in-plane direction, $R_0(450)$, $R_0(550)$ or $R_0(650)$, at the time when light having the measurement wavelength of 450 nm, 550 nm, or 650 nm is incident on the optical film after humidification in parallel to the normal line of the film surface, is measured using an AXOSCAN manufactured by Axometrics Co., Ltd.

3) The retardation R(φ) obtained when light having the measurement wavelength of 450 nm, 550 nm or 650 nm is caused to enter at an angle of φ (incident angle (φ)) with respect to the normal line of the surface of the optical film is measured using an AXOSCAN manufactured by Axometrics Co. Ltd., by employing the in-plane slow axis of the optical film as an axis of tilt (axis of rotation). The measurement of the retardation R(φ) can be carried out over the range of φ of 0° to 50°, at six points at an interval of 10°. The in-plane slow axis of the optical film can be identified by an AXOSCAN manufactured by Axometrics Co., Ltd.

4) nx, ny and nz are calculated using an AXOSCAN manufactured by Axometrics Co., Ltd., from $R_0$ and R(φ) measured at each wavelength (λ), and the average refractive indices and film thickness described above. Then, the retardations in the thickness direction, Rth(450), Rth(550) and Rth(650), at the measurement wavelengths of 450 nm, 550 nm and 650 nm are calculated. Measurement of the retardation can be carried out under the conditions of 23° C. and 55% RH.

$$R_0(\lambda)=(nx(\lambda)-ny(\lambda))\times d \text{ (nm)} \qquad \text{Formula (I)}$$

$$Rth(\lambda)=\{(nx(\lambda)+ny(\lambda))/2-nz(\lambda)\}\times d \text{ (nm)} \qquad \text{Formula (II)}$$

wherein in Formulas (I) and (II), nx(λ) represents the refractive index in the slow axis x, at which the refractive index in the in-plane direction of the optical film becomes maximum when light having a wavelength of λ is incident;

ny(λ) represents the refractive index in a direction y perpendicular to the slow axis direction x in the in-plane direction of the optical film when light having the wavelength λ is incident;

nz(λ) represents the refractive index in the thickness direction z of the optical film when light having the wavelength λ is incident; and d (nm) represents the thickness of the optical film.

Furthermore, $R_0(450)/R_0(550)$ is calculated from $R_0(450)$ and $R_0(550)$ thus obtained; and $R_0(550)/R_0(650)$ is calculated from $R_0(550)$ and $R_0(650)$ thus obtained.

The angle θ (angle of orientation) formed by the in-plane slow axis of the optical film and the width direction of the film is preferably from 40° to 50°. When the angle of orientation is in the above-mentioned range, a circularly polarizing plate can be produced easily by bonding, in a roll-to-roll manner, an optical film having a slow axis in an oblique direction with respect to the longitudinal direction, which is wound off from a roll body, with a polarizer film having a transmission axis parallel to the longitudinal direction, which is wound off from a roll body, such that the films overlap with each other in longitudinal direction. Thereby, it is advantageous in terms of production, with reduced cut loss of the film. Measurement of the angle of orientation θ of the optical film can be carried out using an automatic birefringence meter, KOBRA-21ADH (Oji Scientific Instruments Co., Ltd.).

The optical film is preferably such that $Nz=Rth(550)/R_0(550)+0.5$ satisfies the relationship of the following formula (d). When the Nz value is in the following range, the retardation in the thickness direction, Rth, becomes relatively smaller than the retardation in the in-plane direction, $R_0$, and therefore, any change in color tone in an oblique direction of a display device that includes the optical film of the present invention can be reduced.

$$0\leq Nz=Rth(550)/R_0(550)+0.5\leq 1 \qquad (d)$$

$$R_0(\lambda)=(nx(\lambda)-ny(\lambda))\times d \text{ (nm)} \qquad \text{Formula (I)}$$

$$Rth(\lambda)=\{(nx(\lambda)+ny(\lambda))/2-nz(\lambda)\}\times d \text{ (nm)} \qquad \text{Formula (II)}$$

wherein in Formulas (I) and (II), nx(λ) represents the refractive index in the slow axis direction x, at which the refractive index in the in-plane direction of the optical film becomes maximum when light having the wavelength λ is incident;

ny(λ) represents the refractive index in a direction y perpendicular to the slow axis direction x in the in-plane direction of the optical film when light having the wavelength λ is incident;

nz(λ) represents the refractive index in the thickness direction z of the optical film when light having the wavelength λ is incident; and d (nm) represents the thickness of the optical film.

The thickness of the optical film is preferably 250 μm or less, more preferably 100 μm or less, and even more preferably 70 μm or less, in order to reduce variation in the retardation caused by heat or humidity. On the other hand, in order to develop a film strength or retardation at a certain level or higher, the thickness of the optical film is preferably 10 μm or more, and more preferably 20 μm or more. When the thickness of the optical film is in such a range, it is preferable from the viewpoints of thickness reduction of the display device, and productivity.

The haze (total haze) of the optical film is preferably less than 1%, more preferably 0.5% or less, and even more preferably 0.2% or less. When the haze is 1% or more, transparency of the film is reduced, and the film may not sufficiently function as an optical film.

The haze (total haze) of the optical film can be measured according to JIS K-7136 using a hazemeter NDH-2000 manufactured by Nippon Denshoku Industries Co., Ltd. A halogen bulb of 5 V and 9 W may be used as a light source for the haze meter, and a silicon photocell (attached with a relative luminous efficiency filter) may be used as a light receiving section. Measurement of the haze can be carried out under the conditions of 23° C. and 55% RH.

The visible light transmittance of the optical film is preferably 90% or more, and more preferably 93% or more. The fracture elongation in at least one direction of the optical film of the present invention, which is measured according to JIS-K7127-1999, is preferably 10% or more, more preferably 20% or more, and even more preferably 30% or more.

The optical film of the present invention has high retardation in the in-plane direction, and exhibits sufficient reverse wavelength dispersibility. Therefore, the optical film of the present invention has high retardation over a wide wavelength region.

The optical film of the present invention is used as an optical film for an image display device such an organic EL display device or a liquid crystal display device; specifically as a polarizing plate protective film, a retardation film, an optical compensation film, or an antireflective film. Preferably, the optical film of the present invention is used as a λ/4 retardation film.

The λ/4 retardation film has a retardation in the in-plane direction $R_0$ of about ¼ of the wavelength of predetermined light (typically, visible light region). The λ/4 retardation film is preferably formed from a single layer of the optical film of the present invention. The λ/4 retardation film is preferably used in an antireflective film of an organic EL display device.

2. Method for Producing Optical Film

The optical film of the present invention can be produced by a solution casting method or a melt casting method. From the viewpoint of suppressing optical defects such as coloration of the optical film, foreign matter defects, and die lines, a solution casting method is preferred; and from the viewpoint of suppressing remaining of a solvent in the optical film, a melt casting method is preferred.

A) Solution Casting Method

The method for producing an optical film containing cellulose acetate by a solution casting method includes: A1) a step of dissolving at least cellulose acetate and optionally other additives in a solvent, and thereby producing a dope; A2) a step of casting the dope on an endless metal support; A3) a step of evaporating the solvent from the cast dope to obtain a web; A4) a step of detaching the web from the metal support; and A5) a step of drying the web, and then stretching the web to obtain a film.

A1) Dope Producing Step

In a melting pot, cellulose acetate and other additives as necessary are dissolved in a solvent, and thus a dope is produced.

Any solvent can be used without limitations as long as the solvent is capable of dissolving cellulose acetate and other additives. Examples of the solvent include, as chlorine-based organic solvents, methylene chloride; and as non-chlorine-based organic solvents, methyl acetate, ethyl acetate, amyl acetate, acetone, tetrahydrofuran, 1,3-dioxolane, 1,4-dioxane, cyclohexanone, ethyl formate, 2,2,2-trifluoroethanol, 2,2,3,3-hexafluoro-1-propanol, 1,3-difluoro-2-propanol, 1,1,1,3,3,3-hexafluoro-2-methyl-2-propanol, 1,1,1,3,3,3-hexafluoro-2-propanol, 2,2,3,3,3-pentafluoro-1-propanol, and nitroethane. Preferably, methylene chloride, methyl acetate, ethyl acetate, acetone and the like can be used.

It is preferable that the dope further contain a linear or branched aliphatic alcohol having 1 to 4 carbon atoms in an amount of 1% to 40% by mass. When the proportion of the alcohol in the dope is high, the web undergoes gelling, and detachment of the web from the metal support is made easier. On the other hand, when the proportion of the alcohol in the dope is small, dissolution of cellulose acetate in a non-chlorine-based organic solvent can be promoted.

Examples of the linear or branched aliphatic alcohol having 1 to 4 carbon atoms include methanol, ethanol, n-propanol, isopropanol, n-butanol, sec-butanol, and tert-butanol. Among them, from the viewpoint of enhancing the stability of the dope, having a relatively low boiling point, and having high dryability, ethanol is preferred.

Among others, the solvent is preferably a mixture of methylene chloride and a linear or branched aliphatic alcohol having 1 to 4 carbon atoms.

The concentration of cellulose acetate in the dope is preferably higher in order to reduce the drying load; however, if the concentration of cellulose acetate is too high, it is difficult to filter the dope. Therefore, the concentration of cellulose acetate in the dope is preferably 10% to 35% by mass, and more preferably 15% to 25% by mass.

The method of dissolving cellulose acetate in a solvent may be, for example, a method of dissolving cellulose acetate by heating under pressure. The heating temperature is preferably higher from the viewpoint of increasing the solubility of cellulose acetate, but if the temperature is too high, it is needed to increase the pressure, so that productivity is decreased. Therefore, the heating temperature is preferably 45° C. to 120° C.

The additives may be added to the dope in a batch, or additive solutions may be separately provided and added in-line. Particularly, for the fine particles, it is preferable to add in-line a portion or the entire amount of the particles in order to reduce the load to the filtering material.

In the case of adding in-line additive solutions, it is preferable to dissolve a small amount of a thermoplastic resin in order to facilitate mixing with the dope. A preferred content of the thermoplastic resin is set to 1 part to 10 parts by mass, and more preferably set to 3 parts to 5 parts by mass, relative to 100 parts by mass of the solvent.

For the in-line addition and mixing, for example, an in-line mixer such as a static mixer (manufactured by Toray Engineering Co., Ltd.) or SWJ (Toray static in-tube mixer, Hi-Mixer) is preferably used.

The resultant dope may include, for example, insoluble materials such as the impurities included in the raw material cellulose acetate. These insoluble materials may serve as bright spot foreign matters for the resulting film. In order to remove these insoluble materials and the like, it is preferable to further filter the dope thus obtained.

Filtration of the dope is preferably carried out such that the number of bright spot foreign matters is less than a predetermined number. Specifically, it is preferable that the number of bright spot foreign matters having a diameter of 0.01 mm or more is 200 objects/cm$^2$ or less, preferably 100 objects/cm$^2$ or less, more preferably 50 objects/cm$^2$ or less, even more preferably 30 objects/cm$^2$ or less, and particularly preferably 10 objects/cm$^2$ or less.

The number of bright spot foreign matters having a diameter of 0.01 mm or less is preferably 200 objects/cm$^2$ or less, more preferably 100 objects/cm$^2$ or less, even more preferably 50 objects/cm$^2$ or less, even more preferably 30 objects/cm$^2$ or less, and particularly preferably 10 objects/cm$^2$ or less, and it is most preferable that the bright spot foreign matters are completely absent.

The number of bright spot foreign matters of the film can be measured by the following procedure.

1) Two sheets of polarizing plates are disposed in a cross-Nicol state, and the film thus obtained is disposed therebetween.

2) When light is exposed to the side of one of the polarizing plates, and observation is made from the side of the other polarizing plate, the number of spots at which leaking light is observed (foreign matters) is counted.

A2) Casting Step

The dope is cast on an endless type metal support through a slit of a pressurized die.

Regarding the metal support, a stainless steel belt, a drum finished by plating the surface with a cast metal, and the like are preferably used. The surface of the metal support is preferably mirror surface-finished.

The width of the cast may be adjusted to 1 m to 4 m. The surface temperature of the metal support for the casting step is set to from −50° C. to a temperature at which the solvent does not undergo boiling and foaming. A higher temperature is preferred because the drying rate of the web can be made faster; however, if the temperature is excessively high, the web may form blisters, or the flatness may be decreased.

The surface temperature of the metal support is preferably 0° C. to 100° C., and more preferably 5° C. to 30° C. It is also acceptable to cool the metal support and gelate the web so that the web may be detached from the drum in a state of containing a large amount of residual solvent.

The method for adjusting the temperature of the metal support is not particularly limited; available methods involve blowing warm or cold air to the metal support or allowing warm water to contact the back side of the metal support. When warm water is used, since the transfer of heat is achieved efficiently, the time taken until the temperature of the metal support becomes steady is short, which is preferable.

In the case of using warm air, warm air at a temperature higher than or equal to the boiling point of the solvent may be used, while air at a temperature higher than the intended temperature is used while preventing foaming, in consideration of the decrease in the temperature of the web caused by the latent heat of vaporization of the solvent. Particularly, it is preferable to perform drying efficiently by varying the temperature of the support and the temperature of the drying air during the period of from casting to the detachment.

A3) Solvent Evaporating Step

The web (dope film obtained by casting the dope on the metal support) is heated on the metal support, and thereby the solvent is evaporated. The method for drying the web or the drying conditions may be set similarly to those of the A2) casting step described above.

A4) Detaching Step

The web from which the solvent has been evaporated on the metal support is detached at the position of detachment on the metal support.

The amount of residual solvent of the web when the web is detached at the position of detachment on the metal support is preferably set to 10% to 150% by mass, more preferably to 20% to 40% by mass or 60% to 130% by mass, and even more preferably to 20% to 30% by mass or 70% to 120% by mass, in order to increase the flatness of the resultant film.

The amount of residual solvent of the web is defined by the following formula:

Amount of residual solvent (%)=(mass of web before heat treatment−mass of web after heat treatment)/(mass of web after heat treatment)×100

Meanwhile, the heat treatment used when the amount of residual solvent is measured means a heat treatment at 115° C. for one hour.

A5) Drying and Stretching Step

The web obtained by detaching from the metal support is dried as necessary, and then is stretched. Regarding the drying of the web, the web may be dried while conveying the web using a number of rolls disposed vertically, or may be dried while conveying the web in a state of having the two edges of the web fixed with clips.

The method for drying the web is desirably a method of drying with hot air, infrared radiation, a heated roll, microwaves, and the like, and in view of being simple, a method of drying with hot air is preferred.

By stretching the web, an optical film having a desired retardation is obtained. The retardation of the optical compensation film can be controlled by adjusting the magnitude of the tension applied to the web.

Stretching of the web is carried out in any one or more direction of the width direction (TD direction), conveyance direction (MD direction), or an oblique direction of the web. In order to adjust the angle θ formed by the in-plane slow axis of the resulting optical film and the width direction of the film to 40° to 50°, it is preferable to stretch the web at least in an oblique direction; specifically, in the 45°-direction with respect to the width direction of the web.

Thereby, a circularly polarizing plate can be produced easily only by bonding, in a roll-to-roll manner, the polarizing film having a transmission axis in the longitudinal direction, which is wound off from a roll body, with the optical film having a slow axis at an angle of 45° with respect to the longitudinal direction, which is wound off from a roll body, such that the longitudinal directions would overlap with each other. Therefore, the cut loss of the film can be reduced, and thus it is advantageous in terms of production.

Stretching of the web may be carried out by uniaxial stretching, or by biaxial stretching. Biaxial stretching may be sequential biaxial stretching, or may be simultaneous biaxial stretching.

The stretch ratio may vary with the film thickness of the resultant optical film, or the retardation required; however, the stretch ratio may be adjusted to, for example, 1.5 times to 2.5 times in an oblique direction.

The stretching temperature of the web may be preferably set to 120° C. to 230° C., more preferably to 150° C. to 220° C., and even more preferably to higher than 150° C. and 210° C. or lower.

The method for stretching the web is not particularly limited, and a method of producing differences in the circumferential speed in a plurality of rolls, and stretching in the casting direction (MD direction) by utilizing the differences in the roll circumferential speed among the rolls (roll stretching method); a method of fixing two edges of the web with clips or pins, and extending the distance between the clips or pins toward the casting direction (MD direction) to stretch the web in the casting direction (MD direction), or extending the distance in the width direction (TD direction) to stretch the web in the width direction (TD direction), or extending the distance in both the casting direction (MD direction) and the width direction (TD direction) to stretch the web in both the casting direction (MD direction) and the width direction (TD direction) (tenter stretching method); and the like may be used. In order to stretch the web in an oblique direction, a tenter that is capable of independently controlling the grip distance (distance from the initiation of gripping to the completion of gripping) of the web transversely using a transverse gripping means, may also be used. These stretching methods may be used in combination.

Examples of a stretching apparatus having a mechanism of stretching in an oblique direction include the stretching apparatus described in Example 1 of Japanese Patent Application Laid-Open No. 2003-340916, the stretching apparatus described in FIG. 1 of Japanese Patent Application Laid-Open No. 2005-284024, the stretching apparatus described in Japanese Patent Application Laid-Open No. 2007-30466, and the stretching apparatus used in Example 1 of Japanese Patent Application Laid-Open No. 2007-94007.

The residual solvent in the web at the time of initiation of stretching may be adjusted preferably to 20% by mass or less, and more preferably to 15% by mass or less.

The film obtained after stretching is dried if necessary, and then is wound. Regarding the drying of the film, as described above, the film may be dried while conveying the film using a number of rolls disposed up and down (roll system), or may be dried while conveying the film in a state of having two edges of the web fixed with clips (tenter system).

B) Melt Casting Method

The method for producing the optical film of the present invention by a melt casting method includes: B1) a step of producing molten pellets (pelletization step); B2) a step of melt kneading the molten pellets, and then extruding the molten pellets (melt extrusion step); B3) a step of cooling and solidifying the molten resin, and obtaining a web (cooling and solidification step); and B4) a step of stretching the web (stretching step).

B1) Pelletizing Step

A resin composition containing a thermoplastic resin, which is a main component of the optical film, is preferably kneaded in advance and pelletized. Pelletization can be carried out by a known method, and for example, a resin composition containing the thermoplastic resin described above and optionally containing additives such as a plasticizer is melt kneaded with an extruder, and then extruded into a strand shape from a die. The molten resin extruded in a strand form is water-cooled or air cooled, and then cut, and thereby pellets can be obtained.

Raw materials for the pellets are preferably dried before being supplied to an extruder in order to prevent the decomposition.

Mixing of an oxidation inhibitor and the thermoplastic resin may be carried out by mixing the components in a solid state; mixing by impregnating the oxidation inhibitor dissolved in a solvent, into the thermoplastic resin; or mixing by spraying the oxidation inhibitor to the thermoplastic resin. Furthermore, the atmosphere around the feeder part of the extruder or the outlet part of the die is preferably set to an atmosphere of dehumidified air or nitrogen gas, in order to prevent deterioration of the raw materials of the pellets.

In the extruder, the resin is preferably kneaded at a low shearing force or a low temperature in order to prevent the deterioration of the resin (the decrease in the molecular weight, and the coloring and the formation of gel, or the like). For example, when the resin is kneaded in the twin-screw extruder, the rotation directions of two screws are preferably set to the same direction by using a deep groove type screw. In order to uniformly knead the resin, two screw shapes preferably engage with each other.

The optical film may also be produced, without pelletizing the resin composition containing a thermoplastic resin, but by performing melt kneading using the thermoplastic resin that has not been melt kneaded, directly as a raw material using an extruder.

B2) Melt-Extruding Step

The obtained molten pellets and other additives if needed are supplied to the extruder from the hopper. The pellets are preferably supplied under a vacuum, a reduced pressure, or an inert gas atmosphere in order to prevent the oxidation decomposition of the pellets, or the like. Then, the molten pellets and other optional additives (film materials) are melt kneaded with an extruder.

The melt temperature of the film materials in the extruder may vary with the kind of the film material, but when the glass transition temperature of the film is designated as Tg° C., the melt temperature is preferably in the range of Tg° C. to (Tg+100°) C., and more preferably in the range of (Tg+10°) C. to (Tg+90°) C.

Furthermore, when additives such as a plasticizer and fine particles are added in the middle of the extruder processing, a mixing apparatus such as a static mixer may be further disposed in the downstream side of the extruder, in order to mix these components uniformly.

The molten resin extruded from the extruder is filtered, if necessary, through a leaf disc filter or the like, subsequently further mixed with a static mixer or the like, and extruded from the die into a film shape.

It is preferable to stabilize the extrusion flow amount using a gear pump. Furthermore, the leaf disc filter used for the removal of foreign matters is preferably a stainless steel fiber sintered filter. A stainless steel fiber sintered filter is a product obtained by producing a complicatedly entangled state of stainless steel fibers, subsequently compressing the fibers, sintering the contact sites, and integrating the sintered product. The filtering accuracy can be adjusted by changing the density by the thickness of the fiber and the amount of compression.

The melt temperature Tm of the resin at the outlet area of the die may be adjusted to about 200° C. to 300° C.

B3) Cooling and Solidification Step

The resin extruded from the die is nipped with a cooling roll and an elastic touch roll, and the molten resin in a film form is fabricated to a predetermined thickness. The molten resin in a film form is cooled gradually with a plurality of cooling rolls, and thereby solidified.

When the glass transition temperature of the resultant film is designated as Tg (° C.), the surface temperature Tr1 of the cooling roll can be adjusted to Tg (° C.) or lower. The surface temperatures of the a plurality of cooling rolls may be different from each other.

An elastic touch roll is also referred to as a compression rotator. Regarding the elastic touch roll, commercially available products may also be used. The film surface temperature Tt on the side of the elastic touch roll may be adjusted to from Tg of the film to (Tg+110° C.).

The solidified molten resin in a film form is detached from the cooling roll using a detaching roll or the like, and thus a web is obtained. When the film-like molten resin is peeled, tension is preferably adjusted in order to prevent the deformation of the resultant web.

B4) Stretching Step

The web thus obtained is stretched using a stretching machine, and thus a film is obtained. Stretching is carried out in any one or more directions of the width direction (TD direction) and the conveyance direction (MD direction) of the web, or an oblique direction. In order to adjust the angle θ1 formed by the in-plane slow axis of the resultant optical film and the width direction of the film to 40° to 50°, it is preferable to stretch the film at least in an oblique direction; specifically, in the 45°-direction with respect to the width direction of the web.

The method for stretching the web, the stretch ratio, and the stretching temperature may be set similarly to those described above.

3. Circularly Polarizing Plate

The circularly polarizing plate of the present invention includes a polarizer (linearly polarizing film), and the optical film of the present invention that is disposed on at least one surface of the polarizer. The optical film of the present invention may be disposed directly on the polarizer, or may be disposed with another layer or film interposed therebetween.

The polarizer may be an iodine-based polarizing film, a dye-based polarizing film using a dichroic dye, or a polyene-based polarizing film. An iodine-based polarizing film and a dye-based polarizing film may be generally a film obtained by uniaxially stretching a polyvinyl alcohol-based film, and then dyeing the film with iodine or a dichroic dye; or may be a film obtained by dyeing a polyvinyl alcohol-based film with iodine or a dichroic dye, and then uniaxially stretching the film (preferably, a film that has been further subjected to a durability treatment with a boron compound). The transmission axis of the polarizer is in parallel with the stretching direction of the film.

The polyvinyl alcohol-based film may be a film produced from a polyvinyl alcohol aqueous solution. As the polyvinyl alcohol-based film, an ethylene-modified polyvinyl alcohol film is preferable as it has excellent polarizing performance and durability performance, and minimal color spotting.

Examples of the dichroic dye include an azo-based dye, a stilbene-based dye, a pyrazolone-based dye, a triphenyl-methane-based dye, a quinoline-based dye, an oxazine-based dye, a thiazine-based dye, and an anthraquinone-based dye.

The thickness of the polarizer is preferably 5 μm to 30 μm, and more preferably 10 μm to 20 μm.

The angle at which the transmission axis of the polarizer and the in-plane slow axis of the optical film of the present invention intersect each other is preferably 40° to 50°.

A reflective polarizing plate may be further disposed between the polarizer and the optical film of the present invention. A reflective polarizing plate transmits linearly polarized light in a direction parallel to the transmission axis of the polarizer, and reflects linearly polarized light in a direction different from that of the transmission axis. An organic EL display device having such a circularly polarizing plate can emit more of the light emitted by a luminescent layer, to the outside.

Examples of the reflective polarizing plate include a birefringent light polarizer in which polymer thin films having different refractive indices are alternately laminated in one direction (described in Japanese Translation of PCT Application Laid-Open No. 8-503312); and a polarizing separating membrane having a cholesteric structure (described in Japanese Patent Application Laid-Open No. 11-44816). Furthermore, a protective film may be further disposed at the surface of the polarizer.

When the optical film of the present invention is disposed on one surface of the polarizer, a transparent protective film other than the optical film of the present invention may be disposed on the other surface of the polarizer. The transparent protective film is not particularly limited, and may be a conventional cellulose ester film or the like. Examples of cellulose ester films that are preferably used include commercially available cellulose ester films (for example, Konica Minolta TAC KC8UX, KC5UX, KC8UCR3, KC8UCR4, KC8UCR5, KC8UY, KC6UY, KC4UY, KC4UE, KC8UE, KC8UY-HA, KC8UX-RHA, KC8UXW-RHA-C, KC8UXW-RHA-NC, and KC4UXW-RHA-NC, all manufactured by Konica Minolta Opto, Inc.).

The thickness of the transparent protective film is not particularly limited, but may be adjusted to about 10 μm to 200 μm, and the thickness is preferably 10 μm to 100 μm, and more preferably 10 μm to 70 μm.

In a case in which a transparent protective film or a λ/4 retardation film is disposed on the outermost surface of a display or the like, the transparent protective film or the λ/4 retardation film may be further provided at the outermost surface with a transparent hard coat layer, an antiglare layer, an antireflective layer, or the like.

The circularly polarizing plate can be produced through a step of bonding a polarizer and the optical film of the present invention. For the adhesive used for the bonding, for example, an aqueous solution of a fully saponified polyvinyl alcohol, or the like is preferably used.

The circularly polarizing plate can be preferably used in an image display device such as an organic EL display device or a liquid crystal display device that will be described below.

4. Image Display Device

The image display device of the present invention includes the optical film of the present invention. Examples of the image display device of the present invention include an organic EL display device and a liquid crystal display device.

Figure 2:
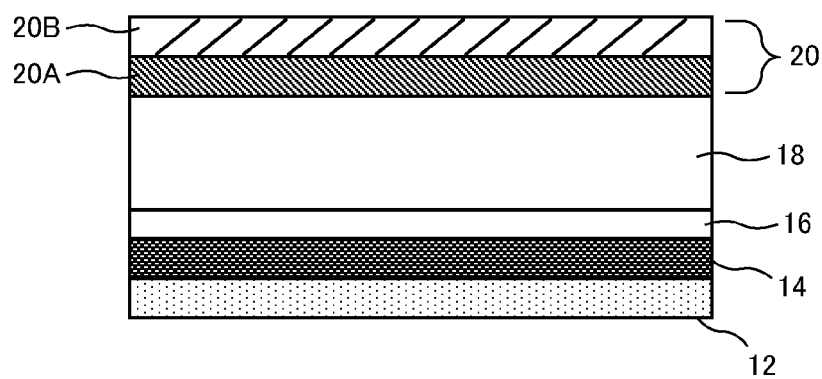
FIG. 2 is a schematic drawing illustrating an example of the configuration of an organic EL display device.

FIG. 2 is a schematic drawing illustrating an example of the configuration of an organic EL display device. As illustrated in FIG. 2, organic EL display device 10 includes light reflective electrode 12, light emitting layer 14, transparent electrode layer 16, transparent substrate 18, and circularly polarizing plate 20 in the order presented. Circularly polarizing plate 20 has λ/4 retardation film 20A and polarizer (linearly polarizing film) 20B; and the optical film of the present invention can be employed as λ/4 retardation film 20A.

Light reflective electrode 12 is preferably composed of a metallic material having high light reflectance. Examples of the metallic material include Mg, MgAg, MgIn, Al, and LiAl. The flatter the surface of light reflective electrode 12, the more it is preferable because diffused reflection of light can be prevented.

Light reflective electrode 12 can be formed by sputtering. Light reflective electrode 12 may be patterned. Patterning can be carried out by etching.

Light emitting layer 14 includes a R (red) light emitting layer, a G (green) light emitting layer, and a B (blue) light emitting layer. Each of the light emitting layers contains a luminescent material. The luminescent material may be an inorganic compound, or may be an organic compound, and is preferably an organic compound.

Each of the light emitting layers may further contain a charge transport material and further have a function as a charge transport layer; or may further contain a hole transport material and further have a function as a hole transport layer. When the light emitting layers do not contain a charge transport material or a hole transport material, organic EL display device 10 may further have a charge transport layer or a hole transport layer.

Each of the light emitting layer may be obtained by patterning. Patterning can be carried out using a photomask or the like. Light emitting layer 14 can be formed by vapor depositing a luminescent material, or the like.

Transparent electrode layer 16 may be generally an ITO electrode. Transparent electrode 16 can be formed by sputtering or the like. The transparent electrode layer 16 may be patterned. Patterning can be carried out by etching.

Transparent substrate 18 may be any substrate capable of transmitting light, and may be a glass substrate, a plastic film, a thin film, or the like.

Circularly polarizing plate 20 is such that the side of λ/4 retardation film 20A is disposed to be on the side of transparent substrate 18; and the side of polarizer 20B is disposed on the visible side.

In the organic EL display device of the present invention, when electricity is passed between light reflective electrode 12 and transparent electrode layer 16, light emitting layer 14 emits light, and the organic EL display device can display an image. Furthermore, since the R (red) light emitting layer, the G (green) light emitting layer, and the B (blue) light emitting layer are respectively configured to be able to pass electricity, displaying of full-color images is enabled.

The optical film of the present invention or a circularly polarizing plate including the same can be applied not only to an organic EL display device having the configuration described above, but also to the organic EL display devices described in WO96/34514, Japanese Patent Application Laid-Open No. 9-127885, and Japanese Patent Application Laid-Open No. 11-45058. In that case, the optical film or circularly polarizing plate of the present invention may be disposed instead of, or together with, the antireflective means of the organic EL display device that has been provided in advance. Furthermore, the optical film or circularly polarizing plate of the present invention may also be applied to, for example, the inorganic EL display device described in "Electroluminescence Display" (written by INOGUCHI, Toshio, Sangyo Tosho Publishing Co., Ltd., published in 1991).

Figure 3:
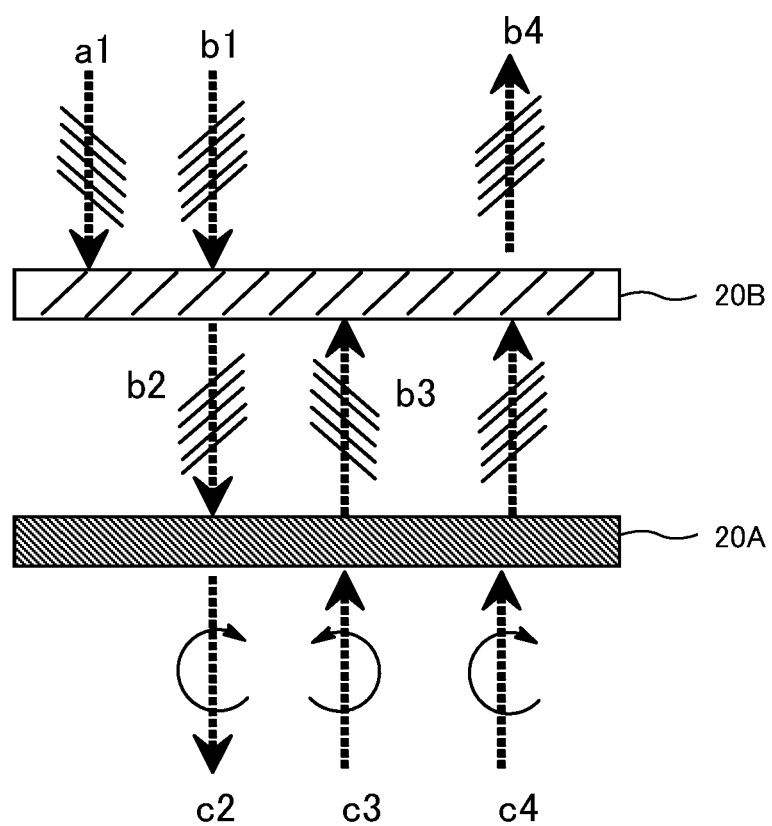
FIG. 3 is a schematic drawing for describing an antireflective function exhibited by a circularly polarizing plate.

FIG. 3 is a schematic drawing illustrating the antireflective function provided by circularly polarizing plate 20. As illustrated in FIG. 3, circularly polarizing plate 20 has polarizer (LP) 20B and λ/4 retardation film 20A disposed on one surface of the polarizer.

When light (including a1 and b1) is incident from the exterior in parallel to the normal line of the display screen of the organic EL display device, only linearly polarized light (b1) that is parallel to the direction of the transmission axis of polarizer (LP) 20B passes through polarizer (LP) 20B. The other linearly polarized light (a1) that is not parallel to the direction of the transmission axis of polarizer (LP) 20B is absorbed by polarizer (LP) 20B. Linearly polarized light component (b2) that has passed through polarizer (LP) 20B is converted to circularly polarized light (c2) by passing through λ/4 retardation film 20A. Circularly polarized light (c2) is converted to reversed circularly polarized light (c3) when reflected at light reflective electrode 12 (see FIGS. 1(A) and 1(B)) of the organic EL display device. Reversed circularly polarized light (c3) is converted to linearly polarized light (b3) in a direction perpendicular to the direction of the transmission axis of polarizer (LP) 20B by passing through λ/4 retardation film 20A. This linearly polarized light (b3) cannot pass through polarizer (LP) 20B and is absorbed thereby.

As such, since light (including a1 and b1) that is incident from the exterior into the organic EL display device is all absorbed by polarizer (LP) 20B, even if the light is reflected at the light reflective electrode of the organic EL display device, no light is emitted to the outside. Therefore, deterioration of the image display characteristics caused by reflection of the background can be prevented.

Further, since λ/4 retardation film 20A of the present invention exhibits sufficient reverse wavelength dispersibility, the λ/4 retardation film can give a retardation of λ/4 to light over a wide wavelength region. Therefore, most of the light incident from the exterior can be prevented from leaking to the outside of the display device. Thereby, the "light leakage in the front direction" on the occasion of displaying a black image on the organic EL display device can be suppressed, and reflection can be prevented.

Furthermore, λ/4 retardation film 20A of the present invention has sufficient reverse wavelength dispersibility, and the thickness of the film can be made small. Therefore, the difference between the color tone in the front direction and the color tone in an oblique direction can be made small. As a result, visibility from an oblique direction can be increased.

Furthermore, the light from the interior of the organic EL display device, that is, the light from light emitting layer 14 (see FIGS. 1A to 1C), includes two kinds of circularly polarized light components (c3 and c4). One component of circularly polarized light (c3) is converted to linearly polarized light (b3) in a direction perpendicular to the direction of the transmission axis of polarizer (LP) 20B by passing through λ/4 retardation film 20A. Then, linearly polarized light (b3) cannot pass through polarizer (LP) 20B and is absorbed thereby. The other circularly polarized light (c4) is converted to linearly polarized light (b4) parallel to the direction of the transmission axis of polarizer (LP) 20B by passing through λ/4 retardation film 20A. Then, linearly polarized light (b4) passes through polarizer (LP) 20B and is converted to linearly polarized light (b4), which is recognized as an image.

A reflective polarizing plate (not shown) that reflects linearly polarized light (b3) in a direction perpendicular to the direction of the transmission axis of polarizer (LP) 20B may be further disposed between polarizer (LP) 20B and λ/4 retardation film 20A. The reflective polarizing plate reflects linearly polarized light (b3) without causing the light to be absorbed at polarizer (LP) 20B, and can cause the light to be reflected again at light reflective electrode 12 (see FIGS. 1(A) and 1(B)) and converted to linearly polarized light (b4) that is parallel to the direction of the transmission axis of polarizer (LP) 20B. That is, by further disposing a reflective polarizing plate, the entirety of the light emitted by light emitting layers (c3 and c4) can be emitted to the outside.

Figure 4:
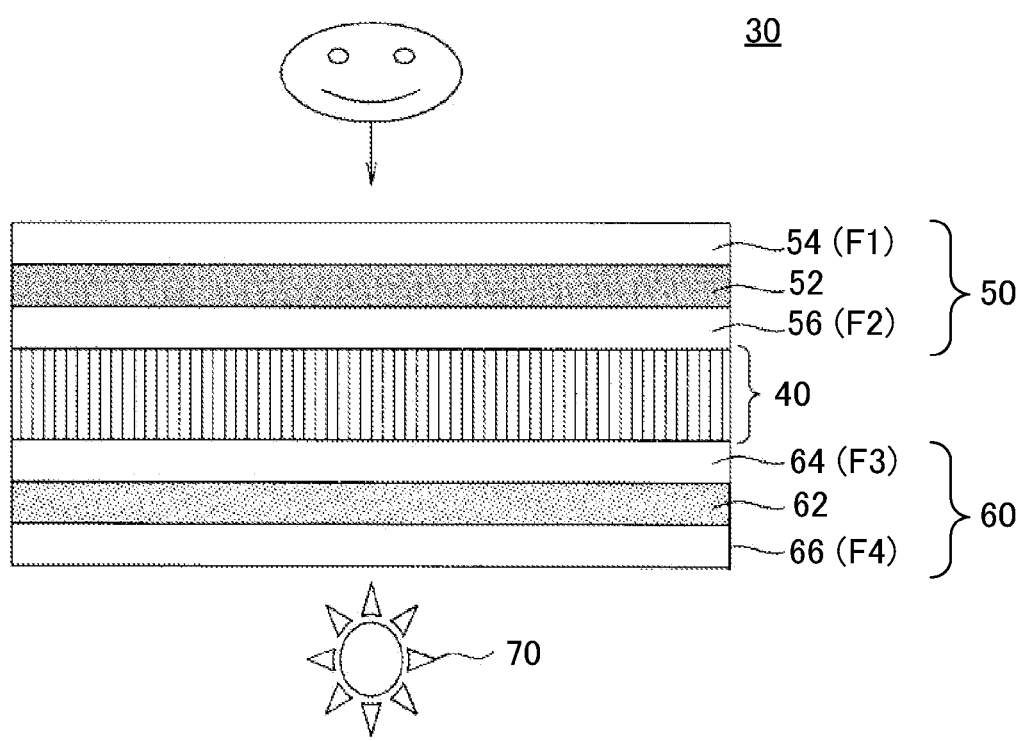
FIG. 4 is a schematic drawing illustrating an example of the configuration of a liquid crystal display device.

FIG. 4 is a schematic drawing illustrating an example of the configuration of a liquid crystal display device. As illustrated in FIG. 4, liquid crystal display device 30 includes liquid crystal cell 40, first polarizing plate 50 and second polarizing plate 60, between which the liquid crystal cell is interposed, and backlight 70.

There are no particular limitations on the display system of the liquid crystal cell 40, and examples include a TN (Twisted Nematic) system, a STN (Super Twisted Nematic) system, an IPS (In-Plane Switching) system, an OCB (Optically Compensated Birefringence) system, a VA (Vertical Alignment) system, (also including MVA; Multi-domain Vertical Alignment, and PVA; Patterned Vertical Alignment), and a HAN (Hybrid Aligned Nematic) system. In order to increase the contrast, a VA (MVA or PVA) system is preferred.

A liquid crystal cell of the VA system has a pair of transparent substrates, and a liquid crystal layer interposed therebetween.

Between the pair of transparent substrates, a pixel electrode for applying a voltage to the liquid crystal molecules is disposed on one of the transparent substrates. A counter electrode may be disposed on the one transparent substrate (where the pixel electrode is disposed), or may be disposed on the other transparent substrate.

The liquid crystal layer contains liquid crystal molecules having negative or positive dielectric anisotropy. The liquid crystal molecules are oriented such that when no voltage is applied (when no electric field is generated between the pixel electrode and the counter electrode), the major axes of the liquid crystal molecules are approximately perpendicular to the surface of the transparent substrate, due to the orientation regulating force of the aligned film provided on the surface of the liquid crystal layer side of the transparent substrate.

In a liquid crystal cell configured as such, an electric field is generated between the pixel electrode and the counter electrode by applying an image signal (voltage) to the pixel electrode. Thereby, the liquid crystal molecules that are initially oriented vertically to the surface of the transparent substrate are oriented such that the major axes thereof come in horizontal direction with respect to the substrate surface. As such, the liquid crystal layer is driven, and the transmittance and reflectance of the various sub-pixels are changed to implement image display.

First polarizing plate 50 has first polarizer 52 that is disposed on the visible side, and protective films 54(F1) and 56(F2), between which first polarizer 52 is interposed. Second polarizing plate 60 is disposed on the side of backlight 70, and has second polarizer 62, and protective film 64(F3) and protective film 66(F4), between which second polarizer 62 is interposed. One of protective films 56(F2) and 64(F3) may not be provided if necessary.

Any one of protective films 54(F1), 56(F2), 64(F3) and 66(F4) can be substituted with the optical film of the present invention.

EXAMPLES

Hereinafter, the present invention will be described in more detail with reference to Examples. The scope of the present invention should not be interpreted in a limited manner by these Examples.

1. Material of Film
1) Thermoplastic Resin
The resins used in Examples or Comparative Examples are presented in Table 1.

Resin (V): DIANAL BR-85 (manufactured by Mitsubishi Rayon Co., Ltd.)

Production of Pellets of Resin (VI)

Synthesis Example 1

In a reaction pot equipped with a stirring apparatus, a temperature sensor, a cooling tube, and a nitrogen inlet tube, 204 kg of methyl methacrylate (MMA), 51 kg of methyl 2-(hydroxymethyl)acrylate (MHMA), and 249 kg of toluene were introduced. Under nitrogen stream, the temperature was increased to 105° C., and the mixture as heated to reflux. Then, 281 g of tertiary-amyl peroxyisononanoate (manufactured by Atofina Yoshitomi, Ltd., trade name: LUPEROX 570) was added thereto as a polymerization initiator, and while a solution of 561 g of the polymerization in 5.4 kg of toluene was added dropwise over 2 hours, solution polymerization was carried out under reflux (about 105° C. to 110° C.). Thereafter, aging was carried out over 4 hours.

255 g of a stearyl phosphate/distearyl phosphate mixture (manufactured by Sakai Chemical Industry Co., Ltd., trade name: PHOSLEX A-18) was added to the polymer solution thus obtained, and a cyclization condensation reaction was carried out under reflux (about 90° C. to 110° C.) for 2 hours.

Subsequently, the polymer solution obtained by the cyclization condensation reaction was introduced to a vent type twin-screw extruder ($\phi$=42 mm, L/D=42) having one rear vent and four fore vents under the conditions of a barrel temperature of 250° C., a speed of rotation of 150 rpm, and a degree of pressure reduction of 13.3 hPa to 400 hPa (10 mmHg to 300 mmHg), at a processing rate of 15 kg/hour in terms of the amount of the resin. A cyclization condensation reaction and devolatilization were carried out in the extruder, and the polymer was extruded. The molten resin thus extruded was cooled in water and then cut, and thus pellets of a transparent heat resistant acrylic resin were obtained.

Subsequently, 90 parts by mass of the pellets of the heat resistant acrylic resin produced as described above, 10 parts by mass of an AS resin (STYLAC AS783 manufactured by Asahi Kasei Chemicals Corp.), and 0.04 part by mass of zinc acetate were introduced into a single-screw extruder with $\phi$50 mm and L/D 36 formed from a full-flight type screw having a mixing unit of a multiple flight structure, and melt kneading was carried out. Melt kneading was carried out at a set cylinder temperature of 270° C. and a processing rate of 50 kg/hour. Thereafter, the molten resin was extruded, cooled in water, and then cut, and thus pellets of resin (VI) were obtained.

The mass average molecular weight of the pellets of resin (VI) thus obtained was 110,000, and the proportion for lactone ring was 28.5%.

TABLE 1

|  | I | II | III | IV | V | VI |
|---|---|---|---|---|---|---|
| Resin | Cellulose ester | | | | (Meth) acrylic resin | |
| Degree of acetyl group substitution | 2.85 | 2.94 | 1.98 | 2.42 | — | — |
| Degree of propionyl group substitution | 0 | 0 | 0.7 | 0 | — | — |
| Total degree of acyl group substitution | 2.85 | 2.94 | 2.68 | 2.42 | — | — |
| Mw | 270,000 | 280,000 | 220,000 | 150,000 | 300,000 | 110,000 |

2) Compounds Used in Present Invention

TABLE 2

| Compound No. | R₁ | L₁ | $\begin{array}{c}W_a\ W_b\\ \diagdown\diagup\\ Q\\ \vert\\ (R_3)_m\end{array}$ | L₂ | R₂ | n |
|---|---|---|---|---|---|---|
| A-41 | C₂H₅──⟨cyclohexyl⟩──⟨cyclohexyl⟩──L₁ | R₁──C(=O)──O──Q | benzothiazole with L₁, L₂ on phenyl | Q──O──C(=O)──R₂ | L₂──⟨cyclohexyl⟩──⟨cyclohexyl⟩──C₂H₅ | 1 |
| A-46 | C₂H₅──⟨cyclohexyl⟩──⟨cyclohexyl⟩──L₁ | R₁──C(=O)──O──Q | benzothiazole with L₁, L₂ on phenyl | Q──O──C(=O)──R₂ | L₂──⟨cyclohexyl⟩──⟨cyclohexyl⟩──C₂H₅ | 1 |
| A-51 | C₅H₁₁──⟨cyclohexyl⟩──C(=O)──O──⟨cyclohexyl⟩──L₅ | R₁──C(=O)──O──Q | benzoxazinone with L₁, L₂ on phenyl | Q──O──C(=O)──R₂ | L₂──⟨cyclohexyl⟩──O──C(=O)──⟨cyclohexyl⟩──C₅H₁₁ | 1 |
| A-62 | C₂H₅──⟨cyclohexyl⟩──⟨cyclohexyl⟩──L₁ | R₁──C(=O)──O──Q | maleimide-phenyl with L₁, L₂ | Q──O──C(=O)──R₂ | L₂──⟨cyclohexyl⟩──⟨cyclohexyl⟩──C₂H₅ | 1 |
| A-65 | C₂H₅──⟨cyclohexyl⟩──⟨cyclohexyl⟩──L₁ | R₁──C(=O)──O──Q | furandione-phenyl with L₁, L₂ | Q──O──C(=O)──R₂ | L₂──⟨cyclohexyl⟩──⟨cyclohexyl⟩──C₂H₅ | 1 |

TABLE 3

| Compound No. | R₁ | L₁ | $\begin{array}{c}W_a\ W_b\\ \diagdown\diagup\\ Q\\ \vert\\ (R_3)_m\end{array}$ | L₂ | R₂ | n |
|---|---|---|---|---|---|---|
| A68 | C₂H₅──⟨cyclohexyl⟩──⟨cyclohexyl⟩──L₁ | R₁──C(=O)──O──Q | pyridinone-phenyl with L₁, L₂ | Q──O──C(=O)──R₂ | L₂──⟨cyclohexyl⟩──⟨cyclohexyl⟩──C₂H₅ | 1 |

TABLE 3-continued
| Compound No. | R₁ | L₁ | $\begin{array}{c} W_a \; W_b \\ -Q- \\ (R_3)_m \end{array}$ | L₂ | R₂ | n |
|---|---|---|---|---|---|---|
| A68 | 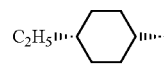 | 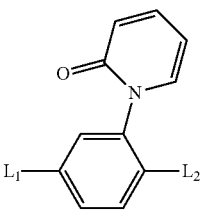 | 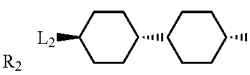 | 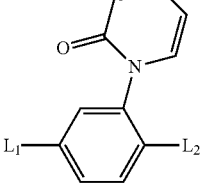 | 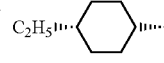 | 1 |
| A-69 | C₆H₁₃—L₁ | R₁—O—Q | 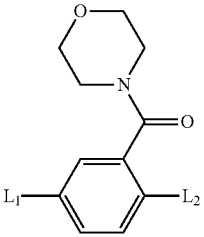 | Q—O—R₂ | L₂—C₆H₁₃ | 1 |
| A-74 | 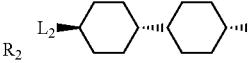 | 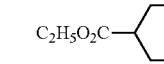 | 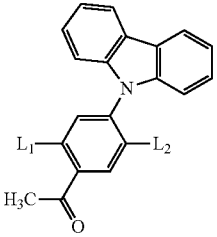 | 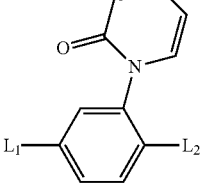 | 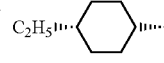 | 1 |
| A-79 | C₂H₅O₂C—⌬—L₁ | 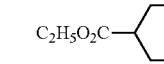 | 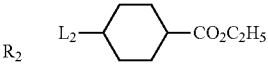 | Q—O—C(=O)—R₂ | L₂—⌬—CO₂C₂H₅ | 1 |
Comparative Compounds
TABLE 4
| Compound No. | Structure |
|---|---|
| Comparative Compound a | 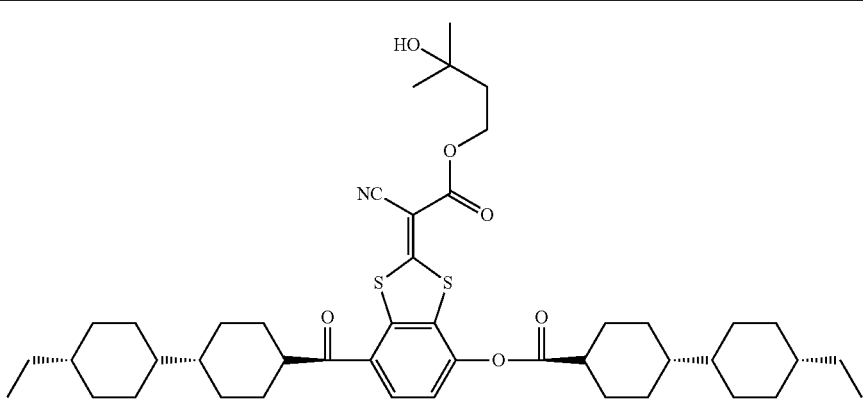 |

TABLE 4-continued
| Compound No. | Structure |
|---|---|
| Comparative Compound b | 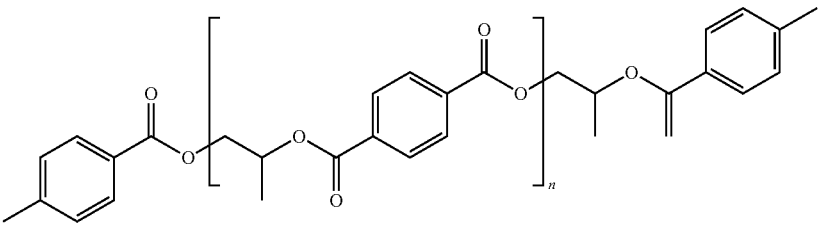 |
| Comparative Compound c | 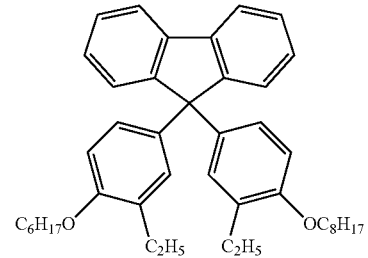 |
| Comparative Compound d | 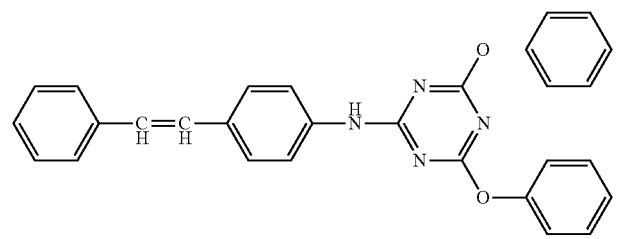 |
| Comparative Compound e | 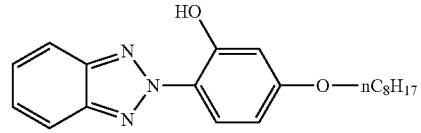 |
TABLE 5
| Compound No. | Structure |
|---|---|
| Comparative Compound f | 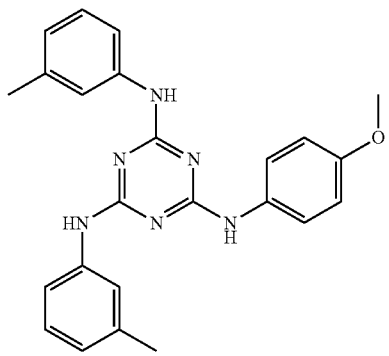 |
| Comparative Compound g | 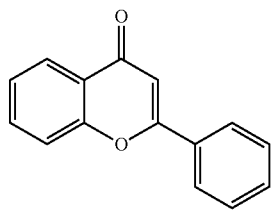 [SMILES: O=c1cc(-c2ccccc2)oc2ccccc12] |

TABLE 5-continued

| Compound No. | Structure |
|---|---|
| Comparative Compound h | C₅H₁₁—[biphenyl]—CN |
| Comparative Compound i | [bis(2-pyridyl ketone)-hydroxyphenyl diester with ethylene glycol linker] |
| Comparative Compound j | [carbazole-N-carbonyl-3,5-dimethyl-4-(n-octyloxy)benzoyl structure, OC₈H₁₇(n)] |

(Measurement of Solution Absorption Spectrum)

Each of the compounds of Tables 2 to 5 was dissolved in tetrahydrofuran (without stabilizer), and thus a solution at a concentration of $10^{-4}$ mol/L was obtained. The solution thus obtained was introduced into a quartz cell (a cell having a square cross-section which measured 10 mm on each side), and the absorbance of the solution in the wavelength region of 200 nm to 350 nm was measured using an ultraviolet-visible-infrared spectrophotometer (U-570, manufactured by JASCO Corp.).

The wavelength of the absorption maximum at longer wavelengths in the wavelength region of 200 nm to 350 nm of the solution absorption spectrum thus obtained was designated as λmax1, with the absorbance at λmax1 being designated as Abs1; and the wavelength of the absorption maximum at shorter wavelengths is designated as λmax2, with the absorbance at λmax2 being designated as Abs2. Then, (λmax1−λmax2) and the absorption ratio Abs1/Abs2 were measured.

(Aspect Ratio of Compounds)

The aspect ratios of the compounds of Tables 2 to 5 were calculated by the method described above.

(In-Plane Retardation Increase Sensitivity)

1) A sample film having a size of 50 mm×50 mm×thickness of 60 μm, containing a thermoplastic resin and a compound presented in Table 2, 3, 4 or 5 in an amount of 1% by weight relative to the thermoplastic resin, was produced, and retardation sensitivity A in the in-plane direction of the sample film was calculated by the method described above.

2) On the other hand, a blank film was produced in the same manner as in section 1) above, except that the compounds of Tables 2 to 5 were not incorporated, and retardation sensitivity B in the in-plane direction of the blank film was measured.

In-plane retardation increase sensitivity=(retardation sensitivity $A$ in the in-plane direction of sample film)−(retardation sensitivity $B$ in the in-plane direction of blank film)

2. Production of Optical Film

Comparative Example 1

Production of Optical Film 1

Preparation of Fine Particle Dispersion Liquid 1

The components described below were mixed with stirring for 50 minutes with a dissolver, and then the mixture was dispersed with a Manton Gaulin homogenizer. Thus, fine particle dispersion liquid 1 was obtained.

(Fine Particle Dispersion Liquid 1)

Fine particles (AEROSIL R972V, manufactured by Nippon Aerosil Co., Ltd.): 11 parts by mass Ethanol: 89 parts by mass Preparation of Fine Particle Additive Liquid 1

Fine particle dispersion liquid 1 thus obtained was slowly added with sufficient stirring to a dissolving tank containing methylene chloride. The solution thus obtained was dispersed with Attritor such that the particle size of secondary particles of the fine particles would be a predetermined size, and then the dispersion was filtered in FINEMET NF manufactured by Nippon Seisen Co., Ltd. Thus, fine particle additive liquid 1 was obtained.

(Fine Particle Additive Liquid 1)

Methylene chloride: 99 parts by mass

Fine particle dispersion liquid 1: 5 parts by mass (Preparation of Dope Solution)

Methylene chloride and ethanol were introduced into a pressurization dissolving tank, and resin (I), a sugar ester compound, Comparative Compound (i) and fine particle additive liquid 1 were introduced therein while being stirred. The solution thus obtained was heated, and was completely dissolved with stirring. The solution thus obtained was filtered using Azumi filter paper No. 244 manufactured by Azumi Filter Paper Co., Ltd., and thus a dope solution was obtained.

(Composition of Dope Solution)
Methylene chloride: 520 parts by mass
Ethanol: 45 parts by mass
Resin (I): 100 parts by mass
Sugar ester compound A described below: 5 parts by mass
Comparative Compound (i): 5 parts by mass
Fine particle additive liquid 1: 1 part by mass

[Chemical Formula 35]

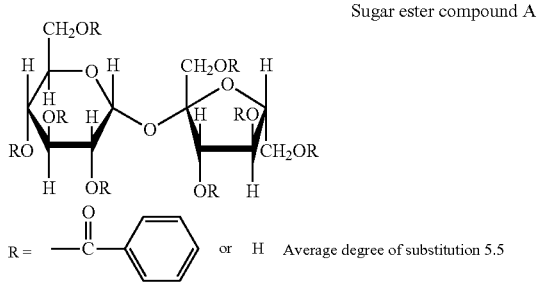

Sugar ester compound A

R = -C(=O)-Ph or H    Average degree of substitution 5.5

The dope solution thus obtained was uniformly cast on a stainless steel belt support using an endless belt casting apparatus. On the stainless steel belt support, the solvent in the dope film thus cast was evaporated until the amount of residual solvent reached 75%, and then a web thus obtained was detached from the stainless steel belt support. The web thus obtained by detachment was conveyed while gripping the web with clips of a tenter stretching apparatus. Subsequently, the film thus obtained was dried in a drying zone while conveying by using a number of rolls. Subsequently, the ends in the width direction of the film that were gripped with the tenter clips were removed by slitting with a razor cutter, and then the film was wound. Thus, a raw film was obtained.

The raw film thus obtained was wound off, and was stretched in an oblique direction at an actual stretch ratio of 110% at a temperature of (glass transition temperature of the raw film+20° C.). Thus, optical film 1 having a film thickness of 85 μm was obtained. The angle θ formed by the in-plane slow axis of optical film 1 thus obtained and the width direction of the film was 45°.

For the optical film thus obtained, $R_0(450)$, $R_0(550)$ and $R_0(650)$ were measured by the method described above, and the wavelength dispersibility was calculated from those values. Furthermore, the haze under the conditions of 23° C. and 55% RH was measured, and the Nz coefficient was calculated. The respective values are presented in Table 6.

3. Production of Circularly Polarizing Plate
Production of Polarizer

A polyvinyl alcohol film having a thickness of 120 μm was uniaxially stretched under the conditions of a stretching temperature of 110° C. and a stretch ratio of 5 times. The film thus obtained was immersed in an aqueous solution containing 0.075 g of iodine, 5 g of potassium iodide, and 100 g of water for 60 seconds, and then was immersed in an aqueous solution at 68° C. containing 6 g of potassium iodide, 7.5 g of boric acid, and 100 g of water. The film thus obtained was washed with water and dried, and thus a polarizer having a thickness of 20 μm was obtained.

Production of Polarizing Plate 1

The surface bonded with the polarizer of optical film 1 produced as described above was subjected to an alkaline saponification treatment. Similarly, Konica Minolta TAC film KC6UA (manufactured Konica Minolta Opto, Inc.) was prepared, and the surface thereof bonded to the polarizer was subjected to an alkaline saponification treatment. Then, on one of the surfaces of the polarizer, optical film 1 was bonded with a 5% aqueous solution of polyvinyl alcohol as an adhesive interposed therebetween; and on the other surface of the polarizer, Konica Minolta TAC film KC6UA (manufactured by Konica Minolta Opto, Inc.) was bonded with a 5% aqueous solution of polyvinyl alcohol interposed therebetween. Thus, circularly polarizing plate 1 was produced. Bonding of optical film 1 and the polarizer was carried out such that the angle formed by the transmission axis of the polarizer and the slow axis of optical film 1 would be 45°.

4. Production of Display Device

A light reflective electrode formed of chromium and having a thickness of 80 nm was formed on a glass substrate by sputtering; and a thin film of ITO having a thickness of 40 nm was formed as a positive electrode on this light reflective electrode. Subsequently, a hole transport layer formed from poly(3,4-ethylenedioxythiophene)-polystyrene sulfonate (PEDOT:PSS) and having a thickness of 80 nm was formed on this positive electrode by sputtering; and light emitting layers of RGB (red light emitting layer, green light emitting layer, and blue light emitting layer) were formed by patterning on the hole transport layer using a shadow mask. The thickness of each light emitting layer was set to 100 nm. The red light emitting layer was formed by co-depositing tris(8-hydroxyquinolinato)aluminum (Alq3) as a host and [4-(dicyanomethylene)-2-methyl-6-(p-dimethylaminostyryl)-4H-pyran] (DCM) as a light emitting compound (mass ratio 99:1); the green light emitting layer was formed by co-depositing Alq3 as a host and coumarin 6 as a light emitting compound (mass ratio 99:1); and the blue light emitting layer was formed by co-depositing Balq as a host and perylene as a light emitting compound (mass ratio 90:10).

[Chemical Formula 36]

BAlq

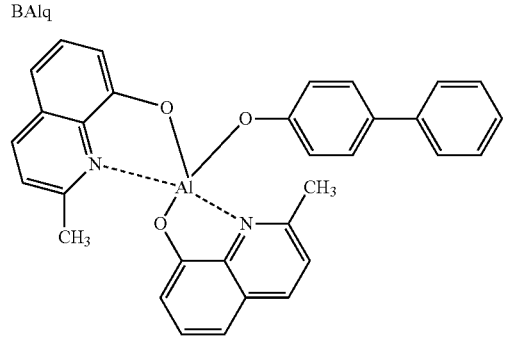

On the light emitting layers of RGB thus obtained, a thin film having a thickness of 4 nm and formed from calcium having a low work function was formed by a vacuum deposition method as a first negative electrode in which electrons can be efficiently injected; and on this first negative electrode, a thin film having a thickness of 2 nm and formed from aluminum was formed as a second negative electrode. Thus, an organic light emitting layer was obtained. The aluminum used as the second negative electrode plays a role of preventing calcium in the first negative electrode from being chemically degenerated when a transparent electrode is formed thereon by sputtering.

Subsequently, a transparent conductive film formed of ITO and having a thickness of 80 nm (the first negative electrode, the second negative electrode, and the transparent conductive film will be collectively referred to as a transparent electrode layer) was formed on the second negative electrode by sputtering. Furthermore, a thin film formed from silicon nitride and having a thickness of 200 nm was formed on the transparent conductive film by CVD to form an insulating film (transparent substrate).

Circularly polarizing plate 1 was bonded on the insulating film (transparent substrate) thus obtained using an adhesive, and thus organic electroluminescent display device 1 was produced. Bonding of circularly polarizing plate 1 was carried out such that optical film 1 came on the side of this insulating film.

Light leakage in the front direction of the display device thus obtained, and the color tone change in an oblique direction were evaluated by the following methods.

(Light Leakage in Front Direction)

The display device was allowed to display a black image for one hour at a commercially available desk stand (Mitsubishi Inverter BB Giraffe) installed at a position 60 cm away from the display screen of the display device, in a state in which light was irradiated to the display screen. The black image was displayed without light emission from the light emitting layer. Thereafter, the luminance was measured in a field of vision within a tilt angle of 0.2° with respect to the normal line of the display screen, using a luminance meter (manufactured by Konica Minolta, Inc.; CS-2000) installed at a position 1 m away from the display screen of the display device. Furthermore, an observer performed sensory observation of the blackness of the display screen or the difference in color tone, at a position 1 m away from the display screen of the display device. The evaluation of light leakage in the front direction was carried out based on the following criteria.

A: The luminance is less than 2 cd/m$^2$, and the image seems stringently black.

B: The luminance is from 2 cd/m$^2$ to 3 cd/m$^2$, and the image seems stringently black.

C: The luminance is larger than 3 cd/m$^2$, or the image does not seem black but seems stained.

(Color Tone Change in Oblique Direction)

The display device was caused to display a black image for one hour at a commercially available desk stand (Mitsubishi Inverter BB Giraffe) installed at a position 60 cm away from the display screen of the display device, in a state in which light was irradiated to the display screen, in a constant temperature constant humidity chamber at 23° C. and 55% RH. The black image was displayed without light emission from the light emitting layer. Thereafter, the level of black tone of the display screen of the display device when observed in the front direction, and the level of black tone of the display screen when observed in a 45° direction with respect to the normal line of the display screen were subjected to a sensory evaluation, and the difference was compared. The evaluation of color tone in an oblique direction was carried out based on the following criteria.

A: No change in black tone can be seen in the front direction and in an oblique direction.

B: A slight difference in black tone in the front direction and in an oblique direction is observed, but this is negligible.

C: A difference in the external light reflection in the front direction and in an oblique direction is sensed.

Comparative Examples 2 to 10, and Examples 1 to 3

Production of Optical Films 2 to 13

A raw film was produced in the same manner as in the case of optical film 1, except that Comparative Compound (i) was changed to one of the compounds as described in Table 6. The raw film was stretched in the same manner as in the case of optical film 1, in an oblique direction at an actual stretch ratio of 110% at (glass transition temperature of the raw film+20° C.). Thus, optical films 2 to 13 having a thickness of 85 μm were obtained. For all of the films, the angle θ formed by the in-plane slow axis of the film and the width direction of the film was 45°.

Production of Display Devices 2 to 13

Subsequently, circularly polarizing plates 2 to 13 and display devices 2 to 13 were produced in the same manner as in Comparative Example 1, except that optical film 1 was changed to optical films 2 to 13. Evaluations of the display device were then carried out.

TABLE 6

| | | Comparative Example 1 | Comparative Example 2 | Example 1 | Example 2 | Comparative Example 3 | Comparative Example 4 | Example 3 |
|---|---|---|---|---|---|---|---|---|
| Optical film No. | | 1 | 2 | 3 | 4 | 5 | 6 | 7 |
| Resin | | I | I | I | I | I | I | I |
| Compound | No. | Comparative Compound i | Comparative Compound c | A-74 | A-51 | Comparative Compound e | Comparative Compound d | A-46 |
| | λmax1 [nm] | 314 | 287 | 267 | 322 | 348 | 347 | 300 |
| | λmax2 [nm] | 302 | 260 | 221 | 238 | 226 | 260 | 231 |
| | (λmax1 − λmax2) [nm] | 12 | 27 | 46 | 84 | 122 | 87 | 69 |
| | Abs1/Abs2 | 1.77 | 0.04 | 0.11 | 19.9 | 28.71 | 97.33 | 0.77 |
| | Aspect ratio | 2.6 | 2.35 | 2.15 | 1.86 | 2.99 | 1.9 | 1.73 |
| | Amount of addition (parts by mass) | 5 | 5 | 5 | 5 | 5 | 5 | 5 |
| Film | In-plane retardation increase sensitivity | 0.1 | 0.08 | 0.19 | 0.2 | 0.03 | 0.07 | 0.13 |
| | Nz coefficient | 1.8 | 1.7 | 1 | 1 | 1.9 | 1.6 | 1 |
| | Film thickness (μm) | 85 | 85 | 85 | 85 | 85 | 85 | 85 |
| | Ro(550)[nm] | 78 | 62 | 140 | 155 | 23 | 55 | 110 |
| | Ro(450)/Ro(550) | 1.01 | 0.98 | 0.84 | 0.84 | 0.93 | 0.93 | 0.89 |
| | Ro(550)/Ro(650) | 1.03 | 0.99 | 0.92 | 0.91 | 0.97 | 0.96 | 0.92 |
| | Haze | 0.08 | 0.12 | 0.08 | 0.13 | 0.13 | 0.12 | 0.11 |
| Display Device No. | | 1 | 2 | 3 | 4 | 5 | 6 | 7 |
| Evaluation | Front direction light leakage | C | C | A | B | C | C | B |
| | Color tone in oblique direction | C | C | A | A | C | C | B |

TABLE 6-continued

|  |  | Comparative Example 5 | Comparative Example 6 | Comparative Example 7 | Comparative Example 8 | Comparative Example 9 | Comparative Example 10 |
|---|---|---|---|---|---|---|---|
| Optical film No. |  | 8 | 9 | 10 | 11 | 12 | 13 |
| Resin |  | I | I | I | I | I | I |
| Compound | No. | Comparative Compound g | Comparative Compound f | Comparative Compound h | Comparative Compound j | Comparative Compound b | Comparative Compound a |
|  | λmax1[nm] | 307 | 275 | 280 | 331 | 282 | 240 |
|  | λmax2[nm] | 237 | 226 | 219 | 277 | 240 | 234 |
|  | (λmax1 − λmax2) [nm] | 70 | 49 | 61 | 54 | 42 | 7 |
|  | Abs1/Abs2 | 1.03 | 3.46 | 1.62 | 1.2 | 0.06 | 1.09 |
|  | Aspect ratio | 1.64 | 1.24 | 2.48 | 2.12 | 4 or more | 1.66 |
|  | Amount of addition (parts by mass) | 5 | 5 | 5 | 5 | 5 | 5 |
| Film | In-plane retardation increase sensitivity | 0.05 | 0.12 | 0.05 | 0.02 | 0.08 | 0.11 |
|  | Nz coefficient | 1.8 | 2 | 1.6 | 1.2 | 1.4 | 1.6 |
|  | Film thickness (μm) | 85 | 85 | 85 | 85 | 85 | 85 |
|  | Ro(550)[nm] | 40 | 95 | 40 | 15 | 62 | 85 |
|  | Ro(450)/Ro(550) | 0.97 | 1.01 | 0.98 | 0.99 | 0.97 | 0.96 |
|  | Ro(550)/Ro(650) | 0.99 | 1.02 | 0.99 | 0.99 | 0.99 | 0.99 |
|  | Haze | 0.1 | 0.19 | 1.12 | 0.8 | 0.6 | 1.1 |
| Display Device No. |  | 8 | 9 | 10 | 11 | 12 | 13 |
| Evaluation | Front direction light leakage | C | C | C | C | C | C |
|  | Color tone in oblique direction | C | C | C | C | C | C |

It can be seen that the optical films of Examples 1 to 3 have all of the in-plane retardation value ($R_0(550)$), Nz coefficient, and wavelength dispersion characteristics ($R_0(450)/R_0(550)$ and $R_0(550)/R_0(650)$) regulated to predetermined ranges. It can also be seen that in the display devices including the optical films of Examples 1 to 3, both the light leakage in the front direction and the color tone change in an oblique direction at the time of displaying a black image can be suppressed.

On the other hand, it can be seen that in the optical films of Comparative Example 1 to 10, since the solution absorption spectrum and the aspect ratio of the compound, and the in-plane retardation increase sensitivity do not satisfy predetermined ranges, the in-plane retardation values deviate largely from λ/4, or the wavelength dispersion characteristics do not satisfy predetermined ranges. Furthermore, it can be seen that in the display devices including the optical films of Comparative Examples 1 to 10, the light leakage in the front direction at the time of displaying a black image or color tone change in an oblique direction cannot be suppressed.

Particularly, it can be seen that in Comparative Examples 1 to 2 and 5 to 10, since the optical films have low in-plane retardation values and do not have sufficient reverse wavelength dispersibility, the light leakage in the front direction at the time of displaying a black image on the display devices including the optical films is large, and the color tone change in an oblique direction are also large. In Comparative Examples 3 and 4, it can be seen that although the wavelength dispersion characteristics of the optical films are preferable, since the in-plane retardation values are too low, the light leakage in the front direction at the time of displaying a black image on the display devices and the color tone change in an oblique direction cannot be suppressed.

Example 4

Production of Optical Film 14

A raw film was produced in the same manner as in the case of optical film 1, except that Comparative compound i was changed to A-46. The raw film was stretched, in the same manner as in the case of optical film 1, in an oblique direction at an actual stretch ratio of 130% at (glass transition temperature of the raw film+20° C.), and thus optical film 14 having a film thickness of 80 μm was obtained. The angle θ formed by the in-plane slow axis and the width direction of the film was 45°.

Production of Display Device 14

Subsequently, circularly polarizing plate 14 and display device 14 were produced in the same manner as in Comparative Example 1, except that optical film 1 was changed to optical film 14. Evaluations of the display device were then carried out.

Examples 5 to 9

Production of Optical Films 15 to 19

Raw films were produced by the same method as that used for optical film 14, except that A-46 was changed to the compounds described in Table 7 in the amounts of addition described therein. Each of the raw films was stretched in the same manner as in the case of optical film 14, in an oblique direction at an actual stretch ratio of 130% at (glass transition temperature of the raw film+20° C.), and thus optical films 15 to 19 having a film thickness of 80 μm were obtained. For all of the films, the angle θ formed by the in-plane slow axis and the width direction of the film was 45°.

Production of Display Devices 15 to 19

Subsequently, circularly polarizing plates 15 to 19 and display devices 15 to 19 were produced in the same manner as in Example 4, except that optical film 14 was changed to optical films 15 to 19. Evaluations of the display devices were then carried out.

TABLE 7

|  |  | Example 4 | Example 5 | Example 6 | Example 7 | Example 8 | Example 9 |
|---|---|---|---|---|---|---|---|
| Optical film No. | | 14 | 15 | 16 | 17 | 18 | 19 |
| Resin | | I | I | I | I | I | I |
| Compound | No. | A-46 | A-69 | A-74 | A-68 | A-69 | A-41 |
|  | $\lambda max1$ [nm] | 300 | 304 | 267 | 305 | 304 | 301 |
|  | $\lambda max2$ [nm] | 231 | 227 | 221 | 237 | 227 | 233 |
|  | ($\lambda max1 - \lambda max2$) [nm] | 69 | 77 | 46 | 68 | 77 | 69 |
|  | Abs1/Abs2 | 0.77 | 0.57 | 0.11 | 3.72 | 0.57 | 5.1 |
|  | Aspect ratio | 1.73 | 2.32 | 2.15 | 2.13 | 2.32 | 2.05 |
|  | Amount of addition (parts by mass) | 5 | 4 | 4 | 4 | 5 | 4 |
| Film | In-plane retardation increase sensitivity | 0.13 | 0.18 | 0.19 | 0.21 | 0.18 | 0.24 |
|  | Nz coefficient | 1.0 | 1.0 | 1.0 | 1.0 | 1.0 | 1.0 |
|  | Film thickness (µm) | 80 | 80 | 80 | 80 | 80 | 80 |
|  | Ro(550) [nm] | 115 | 125 | 135 | 145 | 155 | 165 |
|  | Ro(450)/Ro(550) | 0.89 | 0.87 | 0.84 | 0.79 | 0.86 | 0.87 |
|  | Ro(550)/Ro(650) | 0.92 | 0.92 | 0.92 | 0.84 | 0.91 | 0.90 |
|  | Haze | 0.08 | 0.08 | 0.08 | 0.08 | 0.08 | 0.09 |
| Display device No. | | 14 | 15 | 16 | 17 | 18 | 19 |
| Evaluation | Front direction light leakage | B | B | A | A | B | B |
|  | Color tone in oblique direction | B | A | A | A | A | B |

In all of Examples 4 to 9, the in-plane retardation values of the optical films were in preferred ranges, and the optical films exhibited sufficient wavelength dispersibility. Therefore, light leakage in the front direction at the time of displaying a black image and the color tone change when viewed from an oblique direction were all favorably suppressed.

Example 10

Production of Optical Film 20

A dope solution was obtained in the same manner as in Comparative Example 1, except that the composition of the dope solution was changed as follows.
(Composition of Dope Solution)
Methylene chloride: 523 parts by mass
Ethanol: 45 parts by mass
Resin (II): 100 parts by mass
Sugar ester compound A: 5 parts by mass
A-62: 3 parts by mass
Fine particle additive liquid 1: 1 part by mass A raw film was produced by the same method as that used for optical film 1, except that the dope solution thus obtained was used. The raw film was stretched in the same manner as in the case of optical film 1, in an oblique direction at an actual stretch ratio of 110% at (glass transition temperature of the raw film+20° C.), and thus optical film 20 having a $R_0(550)$ value of 140 nm was obtained. The angle θ formed by the in-plane slow axis and the width direction of the film was 45°.

Production of Display Device 20

Circularly polarizing plate 20 and display device 20 were produced in the same manner as in Comparative Example 1, except that optical film 1 was changed to optical film 20. Evaluations of the display device were then carried out.

Example 11

Production of Optical Film 21

A raw film was produced by the same method as that used in Comparative Example 1, except that Comparative Compound (i) was changed to A-68, and that the amount of addition was changed to 4 parts by mass. The raw film was stretched in the conveyance direction at an actual stretch ratio of 110% at (glass transition temperature of the raw film+20° C.), and optical film 21 having a $R_0(550)$ value of 140 nm was obtained. The angle θ formed by the in-plane slow axis and the width direction of the film was 90°.

Production of Display Device 21

Subsequently, optical film 21 was cut into a piece such that the in-plane slow axis is oriented in a direction at an angle of 45° from the edge of the piece, and the surface bonded with the polarizer was subjected to an alkaline saponification treatment. Except for this, circularly polarizing plate 21 and display device 21 were produced in the same manner as in Comparative Example 1, and evaluations of the display device were carried out.

Example 12

Production of Optical Film 22

A dope solution was obtained by the same method as that used in Comparative Example 1, except that the composition of the dope solution was changed as follows.
(Composition of Dope Solution)
Methylene chloride: 260 parts by mass
Ethanol: 35 parts by mass
Resin (VI): 100 parts by mass
Compound A-68: 5 parts by mass A raw film was produced by the same method as that used for optical film 1, except that the dope solution thus obtained was used. The raw film was stretched in the same manner as in optical film 1, in an oblique direction at an actual stretch ratio of 110% at (glass transition temperature of the raw film+20° C.), and optical film 22 having a $R_0(550)$ value of 140 nm was obtained. The angle θ formed by the in-plane slow axis and the width direction of the film was 45°.

Production of Display Device 22

Subsequently, circularly polarizing plate 22 and display device 22 were produced in the same manner as in Comparative Example 1, except that optical film 1 was changed to optical film 22. Evaluations of the display device were then carried out.

Example 13

Production of Optical Film 23

A dope solution was obtained by the same method as in Comparative Example 1, except that the composition of the dope solution was changed as follows.
(Composition of Dope Solution)
Methylene chloride: 100 parts by mass
Ethanol: 19 parts by mass
Resin (III): 30 parts by mass
Resin (V): 70 parts by mass
Sugar ester compound A: 5 parts by mass
A-68: 10 parts by mass
Fine particle additive liquid 1: 1 part by mass A raw film was obtained by the same method as that used for optical film 1, except that the dope solution thus obtained was used. The raw film was stretched in the same manner as in the case of optical film 1, in an oblique direction at an actual stretch ratio of 110% at (glass transition temperature of the raw film+20° C.), and thus optical film 23 having a $R_0(550)$ value of 140 nm was obtained. The angle θ formed by the in-plane slow axis and the width direction of the film was 45°.

Production of Display Device 23

Subsequently, circularly polarizing plate 23 and display device 23 were produced in the same manner as in Comparative Example 1, except that optical film 1 was changed to optical film 23. Evaluations of the display device were then carried out.

Examples 14 and 17

Production of Optical Films 24 and 27

Raw films were produced by the same method as that used for optical film 1, except that the compounds added and the amounts of addition thereof were changed as described in Table 8. Each of these was stretched in the same manner as in the case of optical film 1, in an oblique direction at an actual stretch ratio of 110% at (glass transition temperature of the raw film+20° C.), and thus optical films 24 and 27 each having a $R_0(550)$ value of 140 nm were obtained. For all of the films, the angle θ formed by the in-plane slow axis and the width direction of the film was 45°.

Production of Display Devices 24 and 27

Circularly polarizing plates 24 and 27 and display devices 24 and 27 were produced in the same manner as in Comparative Example 1, except that optical film 1 was changed to optical films 24 and 27. Evaluations of the display devices were then carried out.

Example 15

Production of Optical Film 25

A dope solution was obtained by the same method as in Comparative Example 1, except that the composition of the dope solution was changed as follows.
(Composition of Dope Solution)
Methylene chloride: 384 parts by mass
Ethanol: 73 parts by mass
Resin (III): 100 parts by mass
Sugar ester compound A: 5 parts by mass
A-46: 3 parts by mass
Fine Particle Additive Liquid 1: 1 Part by Mass A raw film was produced by the same method as that used for optical film 1, except that the dope solution thus obtained was used. The raw film was stretched in the same manner in the case of optical film 1, in an oblique direction at an actual stretch ratio of 110% at (glass transition temperature of the raw film+20° C.), and optical film 25 having a $R_0(550)$ value of 140 nm was obtained. The angle θ formed by the in-plane slow axis and the width direction of the film was 45°.

Production of Display Device 25

Subsequently, circularly polarizing plate 25 and display device 25 were produced in the same manner as in Comparative Example 1, except that optical film 1 was changed to optical film 25. Evaluations of the display device were then carried out.

Example 16

Production of Optical Film 26

A dope solution was obtained by the same method as that used in Comparative Example 1, except that the composition of the dope solution was changed as follows.
(Composition of Dope Solution)
Methylene chloride: 467 parts by mass
Ethanol: 40 parts by mass
Resin (IV): 100 parts by mass
Sugar ester compound A: 5 parts by mass
A-68: 2 parts by mass
Fine particle additive liquid 1: 1 part by mass A raw film was produced by the same method as that used for optical film 1, except that the dope solution thus obtained was used. The raw film was stretched in the same manner as in the case of optical film 1, in an oblique direction at an actual stretch ratio of 110% at (glass transition temperature of the raw film+20° C.), and thus optical film 26 having a $R_0(550)$ value of 140 nm was obtained. The angle formed by the in-plane slow axis and the width direction of the film was 45°.

Production of Display Device 26

Subsequently, circularly polarizing plate 26 and display device 26 were produced in the same manner as in Comparative Example 1, except that optical film 1 was changed to optical film 26. Evaluations of the display device were then carried out.

Examples 18 and 19

Production of Optical Films 28 and 29

Raw films were produced by the same method as that used for optical film 25, except that the compounds added and the amounts of addition thereof were changed as described in Table 8. Each of the raw films was stretched in the same manner as in optical film 1, in an oblique direction at an actual stretch ratio of 110% at (glass transition temperature of the raw film+20° C.), and optical films 28 and 29 each having a $R_0(550)$ value of 140 nm were obtained. For all of the films, the angle θ formed by the in-plane slow axis and the width direction of the film was 45°.

Production of Display Devices 28 and 29

Subsequently, circularly polarizing plates 28 and 29 and display devices 28 and 29 were produced in the same manner as in Comparative Example 1, except that optical film 1 was changed to optical films 28 and 29. Evaluations of the display devices were then carried out.

TABLE 8

|  |  | Example 10 | Example 11 | Example 12 | Example 13 | Example 14 | Example 15 | Example 16 | Example 17 | Example 18 | Example 19 |
|---|---|---|---|---|---|---|---|---|---|---|---|
| Optical film No. |  | 20 | 21 | 22 | 23 | 24 | 25 | 26 | 27 | 28 | 29 |
| Resin |  | II | I | VI | III/V | I | III | IV | I | III | III |
| Compound | No. | A-62 | A-68 | A-68 | A-68 | A-62 | A-46 | A-68 | A-65 | A-65 | A-79 |
|  | $\lambda$max1[nm] | 341 | 305 | 305 | 305 | 341 | 300 | 305 | 340 | 340 | 298 |
|  | $\lambda$max2[nm] | 235 | 237 | 237 | 237 | 235 | 231 | 237 | 265 | 265 | 268 |
|  | ($\lambda$max1 − $\lambda$max2) [nm] | 106 | 68 | 68 | 68 | 106 | 69 | 68 | 75 | 75 | 30 |
|  | Abs1/Abs2 | 0.5 | 3.72 | 3.72 | 3.72 | 0.5 | 0.77 | 3.72 | 2.61 | 2.61 | 0.33 |
|  | Aspect ratio | 1.89 | 2.13 | 2.13 | 2.13 | 1.89 | 1.73 | 2.13 | 2.04 | 2.04 | 1.89 |
|  | Amount of addition (parts by mass) | 3 | 4 | 5 | 10 | 4 | 3 | 2 | 3 | 2 | 3 |
| Film | In-plane retardation increase sensitivity | 0.20 | 0.21 | 0.21 | 0.21 | 0.20 | 0.13 | 0.21 | 0.26 | 0.26 | 0.18 |
|  | Nz coefficient | 1.0 | 0.9 | 1.0 | 1.0 | 1.0 | 1.0 | 1.0 | 1.0 | 1.0 | 1.2 |
|  | Film thickness ($\mu$m) | 95 | 90 | 85 | 100 | 95 | 60 | 45 | 102 | 45 | 45 |
|  | Ro(550) [nm] | 140 | 140 | 140 | 140 | 140 | 140 | 140 | 140 | 140 | 140 |
|  | Ro(450)/Ro(550) | 0.72 | 0.79 | 0.81 | 0.83 | 0.85 | 0.90 | 0.96 | 0.79 | 0.88 | 0.89 |
|  | Ro(550)/Ro(650) | 0.83 | 0.84 | 0.9 | 0.88 | 0.92 | 0.93 | 0.97 | 0.90 | 0.92 | 0.94 |
|  | Haze | 0.09 | 0.08 | 0.09 | 0.15 | 0.09 | 0.08 | 0.09 | 0.08 | 0.07 | 0.09 |
| Display device No. |  | 20 | 21 | 22 | 23 | 24 | 25 | 26 | 27 | 28 | 29 |
| Evaluation | Front direction light leakage | B | A | A | A | A | B | B | A | A | A |
|  | Color tone in oblique direction | B | A | A | A | A | B | B | B | A | B |

In all of Examples 10 to 19, the optical films had sufficient in-plane retardation values, and exhibited favorable wavelength dispersibility. Therefore, the light leakage in the front direction at the time of displaying a black image, and the color tone change when viewed from an oblique direction were favorably suppressed.

The present application claims priority of Japanese Patent Application No. 2012-036837, filed on Feb. 22, 2012. The disclosure of the specification, drawings and abstract is incorporated herein by reference in its entirety.

INDUSTRIAL APPLICABILITY

According to the present invention, an optical film which has high retardation development properties in the in-plane direction and exhibits sufficient reverse wavelength dispersibility even at a small film thickness, can be provided. Furthermore, an image display device including the optical film has excellent black color reproducibility under external light, and has excellent visibility from an oblique direction.

REFERENCE SIGNS LIST

10 Organic EL display device
12 Light reflective electrode
14 Light emitting layer
16 Transparent electrode layer
18 Transparent substrate
20 Circularly polarizing plate
20A $\lambda$/4 retardation film
20B Polarizer (linearly polarizing film)
30 Liquid crystal display device
40 Liquid crystal cell
50 First polarizing plate
52 First polarizer
54 Protective film (F1)
56 Protective film (F2)
60 Second polarizing plate
62 Second polarizer
64 Protective film (F3)
66 Protective film (F4)
70 Backlight

The invention claimed is:

1. An optical film comprising a thermoplastic resin and at least one compound which satisfies all of the following requirements (1) to (5):

(1) the compound has at least two absorption maxima in a wavelength region of from 200 nm to 350 nm in a solution absorption spectrum;
(2) when a wavelength of a first absorption maximum of the two absorption maxima in the wavelength region of from 200 nm to 350 nm is designated as $\lambda$max1, and a wavelength of a second absorption maximum of the two absorption maxima at shorter wavelengths than the first absorption maximum is designated as $\lambda$max2, wherein $\lambda$max1−$\lambda$max2 is 20 nm or more;
(3) an aspect ratio of a molecule of the compound is 1.70 or more;
(4) the compound has a non-aromatic hydrocarbon ring, an aromatic heterocyclic ring, or a non-aromatic heterocyclic ring in the molecule; and
(5) for a sample film having a thickness of 60 $\mu$m and containing the thermoplastic resin and the compound at a proportion of 1% by mass with respect to the thermoplastic resin, when a retardation in an in-plane direction at a wavelength of 550 nm before stretching of the sample film is designated as $R_oA0(550)$, and a retardation in the in-plane direction at a wavelength of 550 nm after stretching at a temperature higher by 25° C. than a glass transition temperature of the sample film is designated as $R_oA1(550)$, so that a in-plane retardation sensitivity obtained by dividing $R_oA1(550)-R_oA0(550)$ by actual stretch ratio of the sample film is designated as A; and for a blank film having a thickness of 60 $\mu$m and formed from the thermoplastic resin, when a retardation in the in-plane direction at a wavelength of 550 nm before stretching of the blank film is designated as $R_oB0(550)$, and a retardation in the in-plane direction at a wavelength of 550 nm after stretching at a temperature higher by 25° C. than a glass transition temperature of the blank film is designated as $R_oB1(550)$, so that an in-plane retardation sensitivity obtained by dividing $R_oB1(550)-R_oB0(550)$ by actual stretch ratio of the blank film is designated as B, an in-plane retardation increase sensitivity defined by A−B is 0.1 or more, wherein when the retardations in the in-plane direction measured at wavelengths of 450 nm, 550 nm and 650 nm are designated as $R_0(450)$, $R_0(550)$ and $R_0(650)$, respectively, the following Formulas (a) to (c) are all satisfied:

$$110 \text{ nm} \leq R_0(550) \leq 170 \text{ nm}; \quad (a)$$

$$0.72 \leq R_0(450)/R_0(550) \leq 0.96; \text{ and} \quad (b)$$

$$0.83 \leq R_0(550)/R_0(650) \leq 0.97. \quad (c)$$

2. The optical film according to claim 1, wherein the thermoplastic resin includes a cellulose derivative.

3. The optical film according to claim 1, wherein the compound has at least one non-aromatic ring in the molecule.

4. The optical film according to claim 1, wherein a value of λmax1−λmax2 of the compound is 50 nm or more.

5. The optical film according to claim 1, wherein when a refractive index in an in-plane slow axis direction of the optical film is designated as nx, a refractive index in a direction perpendicular to the slow axis in the plane of the optical film is designated as ny, and a refractive index in a thickness direction (Rth) of the optical film is designated as nz, the relationship of the following Formula (d) is further satisfied:

$$0 \leq Nz = Rth(550)/R_0(550) + 0.5 \leq 1. \quad (d)$$

6. The optical film according to claim 1, wherein the compound is represented by the following Formula (A):

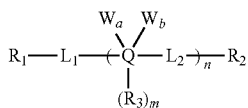

Formula (A)

wherein in Formula (A),
Q represents an aromatic hydrocarbon ring, a non-aromatic hydrocarbon ring, an aromatic heterocyclic ring, or a non-aromatic heterocyclic ring;
$W_a$ and $W_b$ each represent a hydrogen atom or a substituent, $W_a$ and $W_b$ each being bonded to an atom that constitutes the ring of Q, the atom to which $W_a$ is bonded being adjacent to the atom to which $W_b$ is bonded, $W_a$ and $W_b$ being different from each other, and $W_a$ and $W_b$ may be bonded to each other to form a ring;
$R_3$ represents a substituent;
m is an integer from 0 to 2;
when m is 2, $R_3$'s are identical or different;
n represents an integer from 1 to 10; when n is 2 or more, a plurality of Q's, $L_2$'s, $W_a$'s, $W_b$'s, $R_3$'s, and m's are identical or different from each other;
$L_1$ and $L_2$ each independently represent a single bond, or at least one divalent linking group selected from the group consisting of an alkylene group, an alkenylene group, an alkynylene group, —O—, —(C=O)—, —(C=O)—O—, —NR$_L$—, —S—, —(O=S=O)— and —(C=O)—NR$_L$—;
$R_L$ represents a hydrogen atom or a substituent; and
$R_1$ and $R_2$ each independently represent a substituent.

7. The optical film according to claim 6, wherein the compound represented by Formula (A) is a compound represented by the following Formula (B):

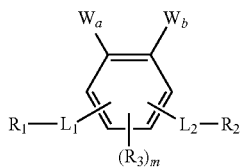

Formula (B)

wherein in Formula (B),
$W_a$ and $W_b$ each represent a hydrogen atom or a substituent, $W_a$ and $W_b$ being different from each other, and $W_a$ and $W_b$ may be bonded to each other to form a ring;
$R_3$ represents a substituent;
m is an integer from 0 to 2;
when m is 2, $R_3$'s are identical or different;
$L_1$ and $L_2$ each independently represent a single bond, or at least one divalent linking group selected from the group consisting of an alkylene group, an alkenylene group, an alkynylene group, —O—, —(C=O)—, —(C=O)—O—, —NR$_L$—, —S—, —(O=S=O)— and —(C=O)—NR$_L$—;
$R_L$ represents a hydrogen atom or a substituent; and
$R_1$ and $R_2$ each independently represent a substituent.

8. The optical film according to claim 7, wherein the compound represented by Formula (B) is a compound represented by the following Formula (1B):

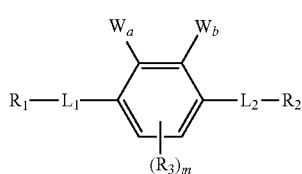

Formula (1B)

wherein in Formula (1B),
$W_a$ and $W_b$ each represent a hydrogen atom or a substituent, $W_a$ and $W_b$ being different from each other, and $W_a$ and $W_b$ may be bonded to each other and form a ring;
$R_3$ represents a substituent;
m is an integer from 0 to 2;
when m is 2, $R_3$'s may bee are identical or different;
$L_1$ and $L_2$ each independently represent a single bond, or at least one divalent linking group selected from the group consisting of an alkylene group, an alkenylene group, an alkynylene group, —O—, —(C=O)—, —(C=O)—O—, —NR$_L$—, —S—, —(O=S=O)— and —(C=O)—NR$_L$—;
$R_L$ represents a hydrogen atom or a substituent; and
$R_1$ and $R_2$ each independently represent a substituent.

9. The optical film according to claim 7, wherein the compound represented by Formula (B) is represented by the following Formula (2B):

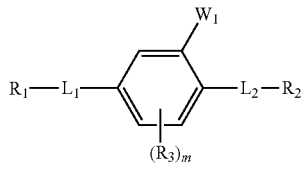

Formula (2B)

wherein in Formula (2B),
$W_1$ represents a cyclic group, and among the ring-constituting atoms of $W_1$, the atom that is bonded to the benzene ring is a carbon atom or a nitrogen atom;
$R_3$ represents a substituent;
m is an integer from 0 to 2;
when m is 2, $R_3$'s are identical or different;
$L_1$ and $L_2$ each independently represent a single bond, or at least one divalent linking group selected from the group consisting of an alkylene group, an alkenylene group, an alkynylene group, —O—, —(C=O)—, —(C=O)—O—, —NR$_L$—, —S—, —(O=S=O)— and —(C=O)—N$_L$—;
$R_L$ represents a hydrogen atom or a substituent; and
$R_1$ and $R_2$ each independently represent a substituent.

10. The optical film according to claim 1, wherein a thickness of the optical film is 10 μm to 100 μm.

11. The optical film according to claim 1, wherein a content of the compound is 1% to 15% by mass with respect to the thermoplastic resin.

12. The optical film according to claim 1, wherein an angle formed by an in-plane slow axis of the optical film and a width direction of the optical film is from 40° to 50°.

13. A circularly polarizing plate comprising the optical film according to claim 1.

14. An image display device comprising the optical film according to claim 1.

* * * * *